(12) United States Patent
Allbritton et al.

(10) Patent No.: US 12,410,391 B2
(45) Date of Patent: Sep. 9, 2025

(54) IN VITRO CELL CULTURE MUCUS SYSTEMS

(71) Applicant: The University of North Carolina at Chapel Hill, Chapel Hill, NC (US)

(72) Inventors: Nancy L. Allbritton, Seattle, WA (US); Yuli Wang, Lynnwood, WA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 807 days.

(21) Appl. No.: 17/284,766

(22) PCT Filed: Nov. 15, 2019

(86) PCT No.: PCT/US2019/061743
§ 371 (c)(1),
(2) Date: Apr. 12, 2021

(87) PCT Pub. No.: WO2020/102682
PCT Pub. Date: May 22, 2020

(65) Prior Publication Data
US 2021/0395661 A1     Dec. 23, 2021

Related U.S. Application Data

(60) Provisional application No. 62/768,259, filed on Nov. 16, 2018.

(51) Int. Cl.
*C12M 1/12* (2006.01)
*C12M 1/06* (2006.01)
*C12N 5/071* (2010.01)

(52) U.S. Cl.
CPC ............ *C12M 25/04* (2013.01); *C12M 27/02* (2013.01); *C12N 5/068* (2013.01)

(58) Field of Classification Search
CPC ........ C12M 25/04; C12M 27/02; C12N 5/068
See application file for complete search history.

(56) References Cited

U.S. PATENT DOCUMENTS

| | | |
|---|---|---|
| 8,946,305 B2 | 2/2015 | Liao et al. |
| 9,040,665 B2 | 5/2015 | Wnek et al. |
| 9,132,208 B2 | 9/2015 | Chen et al. |
| 9,200,676 B2 | 12/2015 | Yamaguchi |
| 9,205,172 B2 | 12/2015 | Leonard Neethling et al. |
| 9,211,362 B2 | 12/2015 | Hwang et al. |
| 9,272,004 B2 | 3/2016 | Nataraj et al. |
| 9,283,301 B1 | 3/2016 | Simionescu et al. |
| 11,193,110 B2 | 12/2021 | Allbritton et al. |
| 2003/0017142 A1 | 1/2003 | Toner et al. |
| 2005/0106717 A1 | 5/2005 | Wilson et al. |
| 2006/0019389 A1 | 1/2006 | Yayon et al. |
| 2006/0121609 A1 | 6/2006 | Yannas et al. |
| 2007/0134790 A1 | 6/2007 | Gould et al. |
| 2009/0253153 A1 | 10/2009 | Chu et al. |
| 2010/0047853 A1 | 2/2010 | Kuo |
| 2010/0075293 A1 | 3/2010 | Chang |
| 2012/0015003 A1 | 1/2012 | Gleeson et al. |
| 2012/0089238 A1 | 4/2012 | Kang et al. |
| 2014/0093478 A1 | 4/2014 | Turnbaugh et al. |
| 2017/0059555 A1 | 3/2017 | Lyer et al. |
| 2017/0191026 A1 | 7/2017 | Alexander |
| 2017/0306278 A1 | 10/2017 | Nguyen et al. |
| 2018/0002672 A1 | 1/2018 | Albritton et al. |
| 2019/0211296 A1 | 7/2019 | Albritton et al. |
| 2019/0382703 A1 | 12/2019 | Katayama |
| 2021/0087515 A1 | 3/2021 | Allbritton et al. |

FOREIGN PATENT DOCUMENTS

| | | |
|---|---|---|
| JP | 2008513159 A | 5/2008 |
| JP | 2009250977 A | 10/2009 |
| JP | 2011523355 A | 8/2011 |
| JP | 2012500371 | 1/2012 |
| JP | 2013510179 A | 3/2013 |
| JP | 2014514942 A | 6/2014 |
| JP | 2019518443 A | 7/2019 |
| JP | 6920203 B2 | 7/2021 |
| JP | 7042252 | 3/2022 |
| WO | WO/2005/072419 | 8/2005 |

(Continued)

OTHER PUBLICATIONS

Bhat, PG, Flanagan, DR, Donovan, MD, The limiting role of mucus in drug absorption: drug permeation through mucus solution. International journal of pharmaceutics. Dec. 29, 1995; 126(1-2):179-187. (Year: 1995).*

Hokari, R., et al., "Vasoactive intestinal peptide upregulates MUC2 intestinal mucin via CREB/ATF1," Am J Physiol Gastrointest Liver Physiol 289(5): G949-859. doi: 10.1152/ajpgi.00142.2005. (Year: 2005).*

Japanese Office Action for Application No. 2021517604 dated Jan. 31, 2024.

Canadian Office Action for Application No. 3009153 dated Mar. 13, 2024.

Gunawardene et al., "Classification and functions of enteroendocrine cells of the lower gastrointestinal tract: Classification and functions of colorectal enteroendocrine cells," International Review of Experimental Pathology, vol. 92, No. 4: 219-231 (Aug. 2011).

(Continued)

*Primary Examiner* — Tracy Vivlemore
*Assistant Examiner* — Eric J Rogers
(74) *Attorney, Agent, or Firm* — KDW FIRM PLLC

(57) ABSTRACT

This presently disclosed subject matter relates to an in vitro cell culture comprising a cell monolayer comprising mucus producing cells and a mucus layer, and methods of making and using the same. The methods including culturing mucus producing cells on a cell support structure under conditions to establish a mucus layer on the luminal side of the cell monolayer, thereby producing a live cell construct comprising a cell monolayer comprising mucus producing cells and a mucus layer. The mucus layer can be substantially impenetrable to micro-objects, and have a thickness of about 1 micron to about 1 cm.

14 Claims, 15 Drawing Sheets

(56) References Cited

FOREIGN PATENT DOCUMENTS

| WO | 2005104755 A2 | 11/2005 | |
|---|---|---|---|
| WO | WO/2009/132196 | 10/2009 | |
| WO | WO/2012/136701 | 10/2012 | |
| WO | WO 2014/021778 A1 | 2/2014 | |
| WO | WO/2014/186430 | 11/2014 | |
| WO | WO 2015/020614 A1 | 2/2015 | |
| WO | WO/2016/123474 | 8/2016 | |
| WO | WO 2017/131839 A2 | 8/2017 | |
| WO | WO/2018/022548 A1 | 2/2018 | |
| WO | WO 2018/052953 A1 | 3/2018 | |
| WO | WO-2018175861 A1 * | 9/2018 | ........... C12N 5/0062 |
| WO | WO 2018/185321 A1 | 10/2018 | |
| WO | 2018225835 A1 | 12/2018 | |
| WO | WO 2019/141824 A1 | 7/2019 | |
| WO | WO2019/222333 | 11/2019 | |
| WO | WO 2019/227012 | 11/2019 | |

OTHER PUBLICATIONS

Extended European Search Report for EP Application No. 21779789. 3, dated Jun. 10, 2024, 13 pages.
Canadian Office Action for Application No. 3093581 dated Aug. 23, 2023.
Canadian Office Action for Application No. 3093585 dated Aug. 28, 2023.
Canadian Office Action for Application No. 3112220 dated Sep. 1, 2023.
Canadian Office Action for Application No. 3170294 dated Sep. 11, 2023.
Japanese Office Action for Application No. 2021517604 dated Aug. 21, 2023.
Japanese Decision to Grant for Application No. 2020560193 dated Sep. 19, 2023.
European Office Action for Application No. 16744178 dated Oct. 10, 2023.
Non-Final Office Action for U.S. Appl. No. 18/371,636 dated Nov. 6, 2023.
Advisory Action and Interview Summary corresponding to U.S. Appl. No. 15/545,456 dated Apr. 10, 2019.
Advisory Action corresponding to U.S. Appl. No. 16/316,139 dated Apr. 4, 2022.
A. DeWard, J. Cramer, and E. Lagasse, Cellular heterogeneity in the mouse esophagus implicates the 30 presence of a nonquiescent epithelial stem cell population, Cell. Rep. 9(2), 701-711 (Oct. 23, 2014).
A. Gracz et al., CD24 and CD44 Mark Human Intestinal Epithelial Cell Populations with Characteristics of Active and Facultative Stem Cells, Stem Cells 31(9), 2024-30 (2013).
A. L. Paguirigan and D. J. Beebe, "Protocol for the fabrication of enzymatically crosslinked gelatin microchannels for microfluidic cell culture" Nat Protoc, 2007, 2, 1782-1788.
Alipour et al. Measurement of Vocal Folds Elastic Properties for Continuum Modeling. Journal of Voice (2012), 26(6), 816.e21-816. e29. (Year: 2012).
A. Quaroni. Short-term primary culture of epithelial cells from human colon. Gastroenterology, 1989, 96, 535-536.
Bartsch et al. "Establishment of a Long-Term Culture System for Rat Colon Epithelial Cells," In Vitro Cell. Dev. Biol.—Animal, 2004, vol. 40, pp. 278-284 (Year: 2004).
Belchior. Gustavo Gross et al. Stem cells and biopharmaceuticals: Vital roles in the growth of tissue-engineered small intestine, Seminars in. Pediatric Surgery, 23(3):141-149 (2014).
Bishop et al. Regulation of Caco-2 cell proliferation by basolateral membrane epidermal growth factor receptors. Am J. Physiol (1994), v267(5 Pt. 1), G892-900. (Year: 1994).
Boccellato et al., "Polarised epithelial monolayers of the gastric mucosa reveal insights into mucosal homeostasis and defence against infection," Gut, vol. 68, pp. 400-413 (2019).
Bo Liu et al. Chemistry of Periodate-Mediated Cross-Linking of 3.4-Dihydroxylphenylalanine (DOPA)-Containing Molecules to Proteins, J Am Chem Soc. 2006; 29:15228-15235, p. 8.
C. Booth, S. Patel, G. R. Bennion and C. S. Patten. The isolation and culture of adult mouse colonic epithelium. Epithelial Cell Biol., 1995, 4, 76-86.
C. Kosinski, et al., Gene expression patterns of human colon tops and basal crypts and BMP antagonists as intestinal stem cell niche factors, Proc. Natl. Acad. Sci. U S. A., 2007, 104, 15418-15423.
C. Moon, K. L. VanDussen, H. Miyoshi and T. S. Stappenbeck. Development of a primary mouse intestinal epithelial cell monolayer culture system to evaluate factors that modulate IgA transcytosis. Mucosal Immunol, 2014, 7, 818-828.
C. R. Yang, "Enhance physiocochemical properties of collagen by using EDC/NHS-crosslinking", Bull. Mat. Sci, 2012, 35, 913-918.
Canadian Office Action Corresponding to Canadian Application No. 3,009,153 dated Feb. 2, 2022.
Cell Culture Inserts, 0.4um, Falcon®. MG Scientific, internet article (2014). (Year: 2014).
Corrected Notice of Allowance corresponding to U.S. Appl. No. 15/545,456 dated Aug. 2, 2021.
Costello et al., "Synthetic Small Intestinal Scaffolds for Improved Studies of Intestinal Differentiation," Biotechnology and Bioengineering, vol. 111, No. 6, Jun. 2014. pp. 1222-1232.
Cummings et al. "Properties of engineered vascular constructs made from collagen, fibrin, and collagen-fibrin mixtures," Biomaterials 25, 3699-3706 (2003).
D.R. Donohoe, N. Garge, X. X. Zhang, W. Sun, T. M. O'Connell, M. K. Bunger and S. J. Bultman, Cell Metabolism, 2011, 13, 517-526.
Donohoe et al., "The Warburg Effect Dictates the Mechanism of Butyrate-Mediated Histone Acetylation and Cell Proliferation," Molecular Cell, vol. 48 pp. 612-626 (2012).
Deveney et al. Establishment of Human Colonic Epithelial Cells in Long-Term Culture. Journal of Surgical Research (1996), 64, 161.
Fuchs et al. "A matter of life and death: self-renewal in stem cells," Embo Reports, vol. 14, No. 1, pp. 39-48 (2013).
E. J. Formeister, A. L. Sionas, D. K. Lorance, C. L. Barkley, G. H. Lee and S. T. Magness, Distinct SOX9 levels differentially mark stem/progenitor populations and enteroendocrine cells of the small intestine epithelium, Am. J Physiol.-Gastroint. Liver Physiol., 2009, 296, G 1108-G1118.
Song et al. "Collagen scaffolds derived from a marine source and their biocompatibility," Biomaterials, 27, 2951-2961 (2006).
Elamin et al., "Effects of Ethanol and Acetaldehyde on Tight Junction Integrity: In Vitro Study in a Three Dimensional Intestinal Epithelial Cell Culture Model." PLoS One, vol. 7, Article ID e35008 (2012).
Extended European Search Report corresponding to European Application No. 16744178.1, dated Jul. 2, 2018, 7 pages.
Extended European Search Report corresponding to European Patent Application No. 17835084.9 dated Mar. 5, 2020.
Extended European Search Report corresponding to European Application No. 19806626.8-1132 dated Feb. 4, 2022.
Extended European Search Report corresponding to European Application No. 19804471.1-1132 dated Feb. 28, 2022.
Extended European Search Report corresponding to European Application No. 19884975.4 dated Jul. 22, 2022.
F. Wang et al., Isolation and Characterization of Intestinal Stem Cells Based on Surface Marker Combinations and Colony-Formation Assay Gastroenterology 145(2), 383-95 (2013a).
Ferruzza et al. A protocol for differentiation of human intestinal Caco-2 cells in asymmetricserum-containing medium. Toxicology in Vitro (2012), v26, p. 1252-1255. (Year: 2012).
Frantz et al. The extracellular matrix at a glance. Journal of Cell Science (2010), 123, 4195-4200. (Year: 2010).
Gaudier et al., "Butyrate specifically modulates MUC gene expression in intestinal epithelial goblet cells deprived of glucose," Am J. Physiol Gastrointest Liver Physiol., vol. 287: G1168-G1174 (2004).
G. L. Eastwood and J. S. Trier. Organ culture of human rectal mucosa. Gastroenterology, 1973, 64(3), 375-382.

(56) References Cited

OTHER PUBLICATIONS

Gracz et al., "Identification, Isolation, and Culture of Intestinal Epithelial Stem Cells from Murine Intestine," Methods Mol Biol.,;vol. 879, pp. 89-107, 23 page author manuscript. (Year: 2012).
Gonzalez S et al. A 3D Culture System Enhances the Ability of Human Bone Marrow Stromal Cells to Support the Growth of Limbal Stem/Progenitor Cells, Stem Cell Res. 2016, 16(2):358-364, p. 2,3.
H. Autrup, L. A. Barrett, F. E. Jackson, M. L. Jesudason, G. Stoner, P. Phelps, B. F. Trump and C. C. Harris. Explant culture of human colon. Gastroenterology, 1978, 74, 1248-1257.
Sundararaghavan et al. "Genipin-induced changes in collagen gels: Correlation of mechanical properties to fluorescence," Journal of Biomedical Materials Research Part A, 87A, 308-320 (2008).
Yoo et al. "Effects of Schisandra Lignans on P-Glycoprotein-Mediated Drug Efflux in Human Intestinal Caco-2 Cells," Planta Med., 73, 444-450 (2007).
H. J. Kim, D. Huh, G. Hamilton and D. E. Ingber. Human gut-on-a-chip inhabited by microbial flora that experiences intestinal peristalsis-like motions and flow. Lab Chip, 2012, 12, 2165-2174.
Hai-Long Li et al. The Effect of Amino Density on the Attachment, Migration, and Differentiation of Rat Neural Stem Cells In Vitro, Mol Cells. 2013; 35:436-443. pp. 436, 437, 441.
Hass et al. Lack of Butyrate Is Associated With Induction of Bax and Subsequent Apoptosis in the Proximal Colon of Guinea Pig. Gastroenterology (1997), 112:875-881. (Year: 1997).
International Preliminary Report on Patentability corresponding to International Application No. PCT/US2016/015631 dated Aug. 1, 2017.
International Preliminary Report on Patentability corresponding to International Application No. PCT/US2017/043601 dated Jan. 29, 2019.
International Preliminary Report on Patentability corresponding to International Application No. PCT/US2019/032393 dated Nov. 17, 2020.
International Preliminary Report on Patentability corresponding to International Application No. PCT/US2019/033955 dated Dec. 1, 2020.
International Preliminary Report on Patentability corresponding to International Application No. PCT/US2019/061743 dated May 18, 2021.
International Search Report corresponding to International Application No. PCT/US2016/015631 dated May 26, 2016.
International Search Report corresponding to International Application No. PCT/US2017/043601 dated Nov. 16, 2017.
International Search Report corresponding to International Application No. PCT/US2019/032393 dated Jul. 23, 2019.
International Search Report corresponding to International Application No. PCT/US2019/033955 dated Aug. 15, 2019.
International Search Report corresponding to International Application No. PCT/US2019/061743 dated Feb. 11, 2020.
Interview Summary corresponding to U.S. Appl. No. 15/545,456 dated Mar. 15, 2019.
J. B. Seidelin, T. Horn and 0. H. Nielsen. Simple and efficient method for isolation and cultivation of endoscopically obtained human colonocytes. Am. J. Physiol.-Gastroint. Liver Physiol., 2003, 285, G1122-G1128.
J. H. Sung, J. J. Yu, D. Luo, M. L. Shuler and J. C. March. Microscale 3-D hydrogel scaffold for biomimetic gastrointestinal (GI) tract model. Lab Chip, 2011, 11, 389-392.
J. H. Sung, M. B. Esch, J. M. Prat, C. J. Long, A. Smith, J. J. Hickman and M. L. Shuler, Microfabricated mammalian organ systems and their integration into models of whole animals and humans. Lab Chip, 2013, 13(7), 1201-1212.
Orban et al. "Crosslinking of collagen gels by transglutaminase," Journal of Biomedical Materials Research Part A, 68A, 756-762 (2004).
J. Mills and R. Shivdasani, Gastric epithelial stem cells, Gastroenterology 140(2), 412-424 (Feb. 2011).

J. R. Davie, "Inhibition of Histone Deacetylase Activity by Butyrate", Journal of Nutrition, 2003, 133, 2485S-2493S.
Jones, S. P. et al., "Inhibition of Histone Deacetylase Activity by Butyrate", Ecotoxicology 23, 802-808 (2014).
VanDussen et al. "Development of an enhanced human gastrointestinal epithelial culture system to facilitate patient-based assays," Gut, vol. 64, pp. 911-920 (2015).
Kaminsky et al. "Small Intestinal Cytochromes P450," Critical Reviews in Toxicology 21, 407-422 (1992).
Kharkar et al. (2013), "Designing degradable hydrogels for orthogonal control of cell microenvironments," Chem. Soc. Rev., vol. 42, pp. 7335-7372. (Year: 2013).
Damink et al. "Glutaraldehyde as a crosslinking agent for collagen-based biomaterials," Journal of Materials Science: Materials in Medicine, 6, 460-472 (1995).
Lancaster, M. A. et al. " Organogenesis in a dish: Modeling development and disease using organoid technologies", Science, 345(6194):283 (2014).
Levenberg S, et al. Differentiation of human embryonic stem cells on three-dimensional polymer scaffolds, PNAS. 2003, 100(22): 12741-12746, p. 12741.
M. A. Cayo, A. K. Cayo, S. M. Jarjour and H. Chen, "Sodium butyrate activates Notch1 signaling, reduces tumor markers, and induces cell cycle arrest and apoptosis in pheochromocytoma", American Journal of Translational Research, 2009, 1, 178-183.
M. Brittan and N. A. Wright, "Stem Cell in Gastrointestinal Structure and Neoplastic Development", Gut, 2004, 53, 899-910.
M. Hovakimyan, R. F. Guthoff and O. Stachs, "Collagen Cross-Linking: Current Status and Future Directions", Journal of Ophthalmology, 2012, 2012, Article ID 406850.
M. Stelzner, M. Helmrath, J. C. Y. Dunn, S. J. Henning, C. W. Houchen, C. Kuo, J. Lynch, L. H. Li, S. T. Magness, M. G. Martin, M. H. Wong, J. Yu and N. I. H. I. S. C. Consortiu, Am. J Physiol.-Gastroint. Liver Physiol., 2012, 302, G1359-G1363.
Maenosono et al. "A Transparent Polyimide Film as a Biological Cell Culture Sheet with Microstructures,". Journal of Biomaterials and Nanobiotechnology, vol. 5, pp. 17-23.(Year: 2014).
Maina JN. Structure, function and evolution of the gas exchangers: comparative perspectives, J Anat. 2002, 201:281-304, p. 300.
Martignoni et al., Abstract of "An in vivo and in vitro comparison of CYP induction in rat liver and intestine using slices and quantitative RT-PCR," Chemico-Biological Interactions, vol. 151, Iss. 1, pp. 1-11 (2004), 19 pages.
Martignoni "Species and strain differences in drug metabolism in liver and intestine," University of Groningen/UMCG, 1-136 (2006).
Matsuzawa A et al. Construction of three-dimensional liver tissue models by cell accumulation technique and maintaining their metabolic functions for long-term culture without medium change, J Biomed Mater Res Part A. 2014, p. 1, Apr. 2015:103(4):1554-64.
Muñoz-Pinto et al. Lamina Propria Cellularity and Collagen Composition: an Integrated Assessment of Structure in Humans. Annals of Otology, Rhinology, and Laryngology (2009), 118(4), 299-306. (Year: 2009).
Barker, M. van de Wetering and H. Clevers, "The intestinal stem cell", Genes & Development, 2008, 22, 1856-1864.
Vrana et al. "EDC/NHS cross-linked collagen foams as scaffolds for artificial corneal stroma," Journal of Biomaterials Science-Polymer Edition, vol. 18, No. 12, pp. 1527-1545 (2007).
N. Seyedhassantehrani, Y. Li and L. Yao, Dynamic behaviours of astrocytes in chemically modified fibrin and collagen hydrogels Integrative Biology, 2016.
Notice of Allowance corresponding to U.S. Appl. No. 15/545,456 dated Jul. 21, 2021.
Notice of Publication corresponding to European Patent Application No. 17835084.9-1120 dated May 8, 2019.
Notice of Publication corresponding to European Patent Application No. 19804471.1 dated Feb. 24, 2021.
Notice of Publication corresponding to European Patent Application No. 19806626.8-1111 dated Mar. 17, 2021.
Notice of Publication corresponding to European Patent Application No. 19884975.4-1132 dated Aug. 25, 2021.
Notice of Allowance corresponding to Japanese Patent Application No. 2019-504019 dated Mar. 8, 2022.

(56) References Cited

OTHER PUBLICATIONS

Office Action (Restriction Requirement) corresponding to U.S. Appl. No. 15/545,456 dated Jul. 5, 2018.
Office Action corresponding to U.S. Appl. No. 15/545,456 dated Aug. 28, 2018.
Office Action corresponding to European Patent Application No. 16744178.1 dated Nov. 11, 2020.
Office Action corresponding to Japanese Patent Application No. 2017540628 dated Nov. 4, 2020.
Office Action corresponding to Japanese Patent Application No. 2017540628 dated Jan. 7, 2020.
Office Action corresponding to Japanese Patent Application No. 2019504019 dated Feb. 28, 2022.
Office Action corresponding to U.S. Appl. No. 15/545,456 dated Jan. 29, 2019.
Office Action corresponding to U.S. Appl. No. 15/545,456 dated Dec. 16, 2019.
Office Action corresponding to U.S. Appl. No. 15/545,456 dated Mar. 13, 2020.
Office Action corresponding to U.S. Appl. No. 15/545,456 dated Oct. 19, 2020.
Office Action (Restriction Requirement) corresponding to U.S. Appl. No. 16/316,139 dated Feb. 4, 2021.
Office Action corresponding to U.S. Appl. No. 16/316,139 dated Apr. 28, 2021.
Office Action corresponding to U.S. Appl. No. 16/316,139 dated Jan. 26, 2022.
Office Action corresponding to U.S. Appl. No. 16/316,139 dated Jun. 14, 2022.
P. Jung, T. Sato, A. Merlos-Suarez, F. M. Barriga, M. Iglesias, D. Rossell, H. Auer, M. Gallardo, M. A. Blasco, E. Sancho, H. Clevers and E. Batlle. Isolation and in vitro expansion of human colic stem cells. Nature Medicine, 2011, 17, 1225-1227.
Shah et al. "Role of Caco-2 cell monolayers in prediction of intestinal drug absorption," Biotechnol. Prog. 22: 186-198 (2006).
Szpak, "Fish bone chemistry and ultrastructure: implications for taphonomy and stable isotope analysis," J. Archaeol. Sci, 38, 3358-3372 (2011).
Paine et al. "Cytochrome P-450 1A1 Expression in Human Small Bowel: Interindividual Variation and Inhibition by Ketoconazole," Drug Metabolism and Disposition, vol. 27, No. 3, pp. 360-364 (1999).
Park YB et al. Alterations of proliferative and differentiation potentials of human embryonic stem cells during long-term culture, Exp Mol Med. 2008, 40(1):98-108, p. 1.
Pedron S. et al. Microfluidic approaches for the fabrication of gradient crosslinked networks based on poly(ethylene glycol) and hyperbranched polymers for manipulation of cell interactions, J Biomed Mat Res. 2011; 96(1):196-203, p. 197.
Petersen et al. Generation of L Cells in Mouse and Human Small Intestine Organoids. Diabetes, 63(2), pp. 410-420.
Q. Ramadan, H. Jafarpoorchekab, C. B. Huang, P. Silacci, S. Carrara, G. Koklu, J. Ghaye, J. Ramsden, C. Ruffert, G. Vergeres and M. A. M. Gijs. NutriChip: nutrition analysis meets microfliudics. Lab Chip, 2013, 13, 196-203.
R. H. Whitehead, A. Brown and P. S. Bhathal. A method for the isolation and culture of human colonic crypts in collagen gels. In Vitro Cellular & Developmental Biology, 1987, vol. 23, No. 6, pp. 436-442.
Ramanujan et al. Diffusion and Convection in Collagen Gels: Implications for Transport in the Tumor Interstitium. Biophysical Journal (2002), 83, 1650-1660. (Year: 2002).
Roeder et al. "Compliance, elastic modulus, and burst pressure of small-intestine submucosa (SIS), small-diameter vascular grafts," J Biomed Mater Res. 47, 65-70 (1999).
Rodriguez-Serrano et al., "Differentiation of Intestinal Epithelial Cells Mediated by Cell Confluence and/or Exogenous Nucleoside Supplementation." Cell Tissues Organs, vol. 191, pp. 478-488 (2010).

Rosa ACP et al. Interaction of *Escherichia coli* strains of non-EPEC serogroups that carry eae and lack the EAF and stx gene sequences with undifferentiated and differentiated intestinal human Caco-2 cells, FEMS Microbiology Letters. 2001, 200: 117-122, p. 118.
S. Umar, Intestinal Stem Cells, Curr. Gastroenterol Rep. 12(5), 340-348 (Oct. 2010).
S. Yui, T. Nakamura, T. Sato, Y. Nemoto, T. Mizutani, X. Zheng, S. Ichinose, T. Nagaishi, R. Okamoto, K. Tsuchiya, H. Clevers and M. Watanabe. Functional engraftment of colon epithelium expanded in vitro from a single adult Lgr5+ stem cell. Nature Medicine, 2012, 18, 618-623.
Seo JB et al. Epithelial monolayer culture system for real-time single-cell analyses, Phys Rep. 2014, 2(4):e12002, p. 1-3.
Simon AK et al. Polymer-Based Mesh as Supports for Multi-layered 3D Cell Culture and Assays, Biomaterials. 2014; 35(1):1-21, abstract.
Soofi, S.S. et al., "The elastic modulus of Matrigel™ as determined by atomic force microscopy" Journal of Structural Biology 167, 216-219 (2009).
Speer et al., "Molecular transport through primary human small intestinal monolayers by culture on a collagen scaffold with a gradient of chemical cross-linking", Journal of Biological Engineering (Apr. 27, 2019).
Spence, Jason el al. "Directed differentiation of human pluripotent stem cells into intestinal tissue in vitro", Nature, 470(7332):105-109 (2011).
Szymanski P et al. Adaptation of High-Throughput Screening in Drug Discovery—Toxicological Screening Tests, Int J Mol Sci. 2012, 13:427-452, abstract.
Sträter et al. Rapid Onset of Apoptosis In Vitro Follows Disruption of beta 1-Integrin/Matrix Interactions in Human Colonic Crypt Cells. Gastroenterology (1996), 110, 1776-1784. (Year: 1996).
T. Sato, D. E. Stange, M. Ferrante, R. G. Vries, J. H. Van Es, S. Van den Brink, W. J. Van Houdt, A. Pronk, J. Van Gorp, P. D. Siersema and H. Clevers. Long-term expansion of epithelial organoids from human colon, adenoma, adenocarcinoma, and Barrett's epitheiuum. Gastroenterology, 2011, 141, 1762-1772.
Sato, et. al. "Paneth Cells constitute the niche for Lgr5 stem cells in intestinal crypts," Nature, 469(7330), pp. 415-418 (2011).
T. Sato, R. G. Vries, H. J. Snippert, M. van de Wetering, N. Barker, D. E. Stange, J. H. van Es, A. Abo, P. Kujala, P. J. Peters and H. Clevers. Single Lgr5 stem cells build crypt-villus structures in vitro without a mesenchymal niche. Nature, 2009, 459, 262-U147.
T. Yen and N. Wright, The gastrointestinal tract stem cell niche, Stem Cell Rev. 2(3), 203-212 (2006).
Tang et al. Utilization of a Human Intestinal Epithelial Cell Culture System (Caco-2) for Evaluating Cytoprotective Agents. Pharm Res (1993), v10(11), p. 1620-1626. (Year: 1993).
Transwell® permeable supports (2007), 8 pages. (Year: 2007).
Wang et al., "Formation of Human Colonic Crypt Array by Application of Chemical Gradients Across a Shaped Epithelial Monolayer", Cellular and Molecular Gastroenterology and Hepatology. vol. 5, No. 2, pp. 113-130 (2018).
Wang et al. Influence of micro-well biomimetic topography on intestinal epithelial Caco-2 cell phenotype. Biomaterials (2009), v30, p. 6825-6834. (Year: 2009).
Wang et al., "Synergic effects of crypt-like topography and ECM proteins on intestinal cell behavior in collagen based membranes," Biomaterials, vol. 31, Iss. 29, pp. 7586-7598 (2010).
Wang, Yuli et al. "A microengineered collagen scaffold for generating a polarized crypt-vilus architecture of human small intestinal epithelium", Biomaterials, 128:44-45 (2017).
Wang et al., "Building a Thick Mucus Hydrogel Layer to Improve the Physiological Relevance of In Vitro Primary Colonic Epithelial Models," Cellular and Molecular Gastroenterology and Hepatology, Jul. 26, 2019 (Jul. 26, 2019), vol. 8, Iss. 4, pp. 653-655.
Watson, Carey et al. "An in vivo model of human small intestine using pluripotent stem cells", Nature Medicine, 20(11)1310-1314 (2014).
Written Opinion and International Search Report corresponding to International Application No. PCT/US2016/015631 dated May 26, 2016.

(56) References Cited

OTHER PUBLICATIONS

Written Opinion and International Search Report corresponding to International Application No. PCT/US2017/043601 dated Nov. 16, 2017.
Written Opinion of the International Searching Authority corresponding to International Application No. PCT/US2019/032393 dated Jul. 23, 2019.
Written Opinion of the International Searching Authority corresponding to International Application No. PCT/US2019/033955 dated Aug. 15, 2019.
Written Opinion of the International Searching Authority corresponding to International Application No. PCT/US2019/061743 dated Feb. 11, 2020.
Yeste et al., "Engineering and monitoring cellular barrier models," Journal of Biological Engineering, Sep. 12, 2018 (Sep. 12, 2018), vol. 12, No. 18, pp. 1-19.
X. Yin, H. F. Farin, J. H. van Es, H. Clevers, R. Langer and J. M. Karp. Niche-independent high-purity cultures of Lgr5+ intestinal stem cells and their progeny. Nature Methods, 2014, 11, 106-112.
Di et al. "Collagen stabilization and modification using a polyepoxide, triglycidyl isocyanurate," Polymer Degradation and Stability, 94, 1684-1692 (2009).
Y. L. Wang, A. A. Ahmad, C. E. Sims, S. T. Magness and N. L. Allbritton. In vitro generation of colonic epithelium from primary cells guided by microstructures. Lab Chip, 2014, 14, 1622-1631.
Y. W. Liu, L. H. Gan, D. J. Carlsson, P. Fagerholm, N. Lagali, M. A. Watsky, R. Munger, W. G. Hodge, D. Priest and M. Griffith, "A Simple, Cross-linked Collagen Tissue Substitute for Corneal Implantation", Invest. Ophthalmol Invest. Ophthalmol. Vis. Sci., 2006, 47, 1869-1875.
Anonye, B. O. et al. Probing host-anaerobe interactions in innovative human gut cellular models. bioRxiv, doi:10.1101/269035, 43 pages (2018).
Anonye et al. Probing Clostridium difficule infection in innovative human gut cellular models, bioRxiv, 269035, 28 pages (2018).
Bertout, J. A., Patel, S. A. & Simon, M. C. The impact of O2 availability on human cancer. Nature reviews. Cancer 8, 967, 22 pages (2008).
Blouin, J. M. et al. Butyrate elicits a metabolic switch in human colon cancer cells by targeting the pyruvate dehydrogenase complex. International journal of cancer 128, 2591-2601 (2011).
Boccellato et al. "Polarised epithelial monolayers of the gastric mucosa reveal insights into mucosa! homeostasis and defence against infection," Gut, Feb. 7, 2018 (Feb. 7, 2018), vol. 68, pp. 400-413.
Brennan, M. D., Rexius-Hall, M. L. & Eddington, D. T. A 3D-printed oxygen control insert for a 24-well plate. PloS one 10, e0137631, 9 pages (2015).
Buchwald, P. FEM-based oxygen consumption and cell viability models for avascular pancreatic islets. Theoretical Biology and Medical Modelling 6, 5, 13 pages (2009).
Byrne, M. B., Leslie, M. T., Gaskins, H. R. & Kenis, P. J. "Methods to study the tumor microenvironment under controlled oxygen conditions," Author manuscript, 19 pages, published in final edited form as: Trends in biotechnology 32, 556-563 (2014).
Cani, P. D. "Gut microbiota—at the intersection of everything?" Abstract of Nature Reviews Gastroenterology & Hepatology 14, 321-322 (2017) [6 pages].
Chen, Y. et al. "Robust bioengineered 3D functional human intestinal epithelium," Scientific reports 5, 13708, 11 pages (2015).
Chen, Y.-A. et al. "Generation of oxygen gradients in microfluidic devices for cell culture using spatially confined chemical reactions," Abstract of Lab on a Chip 11, 3626-3633, 6 pages (2011).
Colgan, S. P. & Taylor, C. T. "Hypoxia: an alarm signal during intestinal inflammation," Author Manuscript, published in final edited form as: Nature Reviews Gastroenterology and Hepatology 7, 281-287 (2010) [16 pages].
Colgan, S.P., Dzus, A.L. & Parkos, C.A. "Epithelial exposure to hypoxia modulates neutrophil transepithelial migration," Journal of Experimental Medicine 184, 1003-1015 (1996).

Eveillard, M. et al. "Identification and characterization of adhesive factors of Clostridium difficile involved in adhesion to human colonic enterocyte-like Caco-2 and mucus-secreting HT29 cells in culture," Molecular microbiology 7, pp. 371-381 (1993).
Gersemann, M. et al. "Differences in goblet cell differentiation between Crohn's disease and ulcerative colitis," Abstract of Differentiation 77, pp. 84-94 (2009)[3 pages].
Gibson et al. "Isolation of Colonic Crypts That Maintain Structural and Metabolic Viability In Vitro," Gastroenterology, 1989, vol. 96, pp. 283-291 (Year: 1989).
Gross, M. W., Karbach, U., Groebe, K., Franko, A. J. & Mueller-Klieser, W. "Calibration of misonidazole labeling by simultaneous measurement of oxygen tension and labeling density in multicellular spheroids," International journal of cancer 61, 567-573 (1995).
Huang, Y., Zitta, K., Bein, B., Steinfath, M. & Albrecht, M. An insert-based enzymatic cell culture system to rapidly and reversibly induce hypoxia: investigations of hypoxia-induced cell damage, protein expression and phosphorylation in neuronal IMR-32 cells. Disease models & mechanisms 6, 1507-1514 (2013).
Hubbi, M.E. & Semenza, G.L. Regulation of cell proliferation by hypoxia-inducible factors. American Journal of Physiology-Cell Physiology 309, C775-C782 (2015).
Ivanovic, Z. Hypoxia or in situ normoxia: The stem cell paradigm. Journal of cellular physiology 219, 271-275 (2009).
JanssenDuijghuijsen, L.M. et al. Mitochondrial ATP Depletion Disrupts Caco-2 Monolayer Integrity and Internalizes Claudin 7. Frontiers in Physiology 8 (2017).
Janvilisri, T., Scaria, J. & Chang, Y.-F. Transcriptional profiling of Clostridium difficile and Caco-2 cells during infection. The Journal of infectious diseases 202, 282-290 (2010).
Kaidi, A., Williams, A.C. & Paraskeva, C. Interaction between β-catenin and HIF-1 promotes cellular adaptation to hypoxia. Nature cell biology 9, 210-217 (2007).
Kaiko, G. E. & Stappenbeck, T. S. Host-microbe interactions shaping the gastrointestinal environment. Trends in immunology 35, 538-548 (2014).
Kelly, C.J. et al. Fundamental role for HIF-1α in constitutive expression of human β defensin-1. Mucosal Immunology 6, 1110 (2013).
Kim, H. J., Li, H., Collins, J. J. & Ingber, D. E. Contributions of microbiome and mechanical deformation to intestinal bacterial overgrowth and inflammation in a human gut-on-a-chip. Proceedings of the National Academy of Sciences 113, E7-E15 (2016).
Kim, Y.-G. et al. Neonatal acquisition of Clostridia species protects against colonization by bacterial pathogens. Science 356, 315-319, doi: 10.1126/science.aag2029 (2017).
Koh, M. Y. & Powis, G. Passing the baton: the HIF switch. Trends in biochemical sciences 37, 364-372 (2012).
Lamberti, A., Marasso, S. L. & Cocuzza, M. PDMS membranes with tunable gas permeability for microfluidic applications. Rsc Advances 4, 61415-61419 (2014).
LeBlanc, J. G. et al. Bacteria as vitamin suppliers to their host: a gut microbiota perspective. Current opinion in biotechnology 24, 160-168 (2013).
Leffler, D.A. & Lamont, J.T. Clostridium difficile Infection. New England Journal of Medicine 372, 1539-1548 (2015).
Lynch, S.V. & Pedersen, O. The Human Intestinal Microbiome in Health and Disease. N Engl J Med 375, 2369-2379 (2016).
Markov, D. A., Lillie, E. M., Garbett, S. P. & McCawley, L. J. Variation in diffusion of gases through PDMS due to plasma surface treatment and storage conditions. Biomedical microdevices 16, 91-96 (2014).
Marzorati, M. et al. The HMI™ module: a new tool to study the Host-Microbiota Interaction in the human gastrointestinal tract in vitro. BMC microbiology 14, 133 (2014).
Nagpal, R., Yadav, H. & Marotta, F. Gut microbiota: the next-gen frontier in preventive and therapeutic medicine? Frontiers in medicine 1 (2014).
Oppegard, S. C. & Eddington, D. T. A microfabricated platform for establishing oxygen gradients in 3-D constructs. Biomedical microdevices 15, 407-414 (2013).

(56) References Cited

OTHER PUBLICATIONS

Oppegard, S. C., Blake, A. J., Williams, J. C. & Eddington, D. T. Precise control over the oxygen conditions within the Boyden chamber using a microfabricated insert. Lab on a chip 10, 2366-2373 (2010).
Oppegard, S. C., Nam, K.-H., Carr, J. R., Skaalure, S. C. & Eddington, D. T. Modulating temporal and spatial oxygenation over adherent cellular cultures. PloS one 4, e6891 (2009).
Peery, A.F. et al. Burden of gastrointestinal disease in the United States: 2012 update. Gastroenterology 143, 1179-1187. e1173 (2012).
Quaroni et al. "Epithelioid Cell Cultures From Rat Small Intestine," J. Cell Biology, 1979, vol. 80, pp. 248-265 (Year: 1979).
Ex Parte Quayle Action and Interview Summary corresponding to U.S. Appl. No. 15/545,456 dated Mar. 16, 2021.
Rexius-Hall, M. L., Mauleon, G., Malik, A. B., Rehman, J. & Eddington, D. T. Microfluidic platform generates oxygen landscapes for localized hypoxic activation. Lab on a chip 14, 4688-4695 (2014).
Sampson, T. R. et al. Gut microbiota regulate motor deficits and neuroinflammation in a model of Parkinson's disease. Cell 167, 1469-1480. e1412 (2016).
Schneeberger, K., Roth, S., Nieuwenhuis, E.E. & Middendorp, S. Intestinal epithelial cell polarity defects in disease: lessons from microvillus inclusion disease. Disease models & mechanisms 11, dmm031088 (2018).
Schuijers, J. & Clevers, H. Adult mammalian stem cells: the role of Wnt, Lgr5 and R-spondins. The EMBO journal 31, 2685-2696 (2012).
Shah, P. et al. A microfluidics-based in vitro model of the gastro-intestinal human-microbe interface. Nature communications 7 (2016).
Shimamura, S. et al. Relationship Between Oxygen Sensitivity and Oxygen Metabolism of Bifidobacterium Species. Journal of Dairy Science 75, 3296-3306 (1992).
Simon, M. C. & Keith, B. The role of oxygen availability in embryonic development and stem cell function. Nature reviews. Molecular cell biology 9, 285 (2008).
Skolimowski, M. et al. Microfluidic dissolved oxygen gradient generator biochip as a useful tool in bacterial biofilm studies. Lab on a Chip 10, 2162-2169 (2010).
Sommer, F., Anderson, J.M., Bharti, R., Raes, J. & Rosenstiel, P. The resilience of the intestinal microbiota influences health and disease. Nat Rev Microbiol 15, 630-638 (2017).
Tsujii, M. et al. Colonic mucosal hemodynamics and tissue oxygenation in patients with ulcerative colitis: Investigation by organ reflectance spectrophotometry. Journal of Gastroenterology 30, 183-188 (1995).
Uchida, H., Sato, A., Miyayama, A. & Tsukada, K. Generation of an oxygen gradient in a microfluidic device and cellular analysis in hypoxia. Advanced Biomedical Engineering 2, 143-149 (2013).
Ulluwishewa, D. et al. Live Faecalibacterium prausnitzii in an apical anaerobic model of the intestinal epithelial barrier. Cellular microbiology 17, 226-240 (2015).
Varia, M.A. et al. Pimonidazole: a novel hypoxia marker for complementary study of tumor hypoxia and cell proliferation in cervical carcinoma. Gynecologic oncology 71, 270-277 (1998).
Wagner, B.A., Venkataraman, S. & Buettner, G.R. The rate of oxygen utilization by cells. Free radical biology & medicine 51, 700-712 (2011).
Waligora, A.J., Barc, M.C., Bourlioux, P., Collignon, A. & Karjalainen, T. Clostridium difficile cell attachment is modified by environmental factors. Applied and environmental microbiology 65, 4234-4238 (1999).
Walsh III, D. I. et al. Emulation of Colonic Oxygen Gradients in a Microdevice. SLAS Technology: Translating Life Sciences Innovation, 2472630317743425 (2017).
Wang, Y. et al. Bioengineered Systems and Designer Matrices That Recapitulate the Intestinal Stem Cell Niche. Cell Mol Gastroenterol Hepatol 5, 440-453 e441 (2018).

Wang, Y. et al. Self-renewing monolayer of primary colonic or rectal epithelial cells. Cellular and Molecular Gastroenterology and Hepatology (2017).
Wang et al. "Capture and 3D culture of colonic crypts and colonoids in a microarray platform," Lab Chip, The Royal Society of Chemistry, vol. 13, pp. 4625-4634 (2013b).
Ward, J. B., Keely, S. J. & Keely, S. J. "Oxygen in the regulation of intestinal epithelial transport," The Journal of physiology 592, pp. 2473-2489 (2014).
Wiegand, P.N. et al. Clinical and economic burden of Clostridium difficile infection in Europe: a systematic review of healthcare-facility-acquired infection. Journal of Hospital Infection 81, 1-14 (2012).
Zeitouni, N. E., Chotikatum, S., von Köckritz-Blickwede, M. & Naim, H. Y. The impact of hypoxia on intestinal epithelial cell functions: consequences for invasion by bacterial pathogens. Molecular and cellular pediatrics 3, 14 (2016).
Zheng, L., Kelly, C. J. & Colgan, S. P. "Physiologic hypoxia and oxygen homeostasis in the healthy intestine. A review in the theme: cellular responses to hypoxia," American Journal of Physiol Cell Physiol 309, pp. C350-C360 (2015).
Zhou, W. et al. Multifunctional bioreactor system for human intestine tissues. ACS biomaterials science & engineering 4, 231-239 (2017).
Barkla et al. "The fate of epithelial cells in the human large intestine." Pathology vol. 31, pp. 230-238, (1999).
Bartfeld, "Modeling infectious diseases and host-microbe interactions in gastrointestinal organoids." Developmental biology, vol. 420, pp. 262-270, (2016).
Basak et al., "Induced quiescence of Lgr5+ stem cells in intestinal organoids enables differentiation of hormone-producing enteroendocrine cells." Cell Stem Cell, vol. 20, pp. 177-190 e4, (2017).
Dekkers et al., "A functional CFTR assay using primary cystic fibrosis intestinal organoids." Nature medicine, vol. 19, pp. 939, (2013).
Finkbeiner et al., "Stem cell-derived human intestinal organoids as an infection model for rotaviruses." MBio vol. 3, e00159-12, (2012).
Gamet et al., "Effects of short-chain fatty acids on growth and differentiation of the human colon-cancer cell line HT29." International Journal of Cancer vol. 52, pp. 286-289, (1992).
Gattazzo et al., "Extracellular matrix: a dynamic microenvironment for stem cell niche." Biochimica et Biophysica Acta (BBA)-General Subjects, vol. 1840, pp. 2506-2519, (2014).
Hall et al., "Human genetic variation and the gut microbiome in disease." Nature Reviews Genetics vol. 18, pp. 690, (2017).
In et al., "Enterohemorrhagic *Escherichia coli* reduces mucus and intermicrovillar bridges in human stem cell-derived colonoids." Cellular and molecular gastroenterology and hepatology vol. 2, pp. 48-62 e3, (2016).
Ito et al., "Metabolism and the control of cell fate decisions and stem cell renewal." Annual review of cell and developmental biology. vol. 32, pp. 399-409, (2016).
Kaiko et al., "The colonic crypt protects stem cells from microbiota-derived metabolites." Cell vol. 165, pp. 1708-1720, (2016).
Karve et al., "Intestinal organoids model human responses to infection by commensal and Shiga toxin producing *Escherichia coli*." PloS one vol. 12, e0178966, (2017).
Kozuka et al., "Development and Characterization of a Human and Mouse Intestinal Epithelial Cell Monolayer Platform." Stem cell reports vol. 9, pp. 1976-1990, (2017).
Li et al., "Role of mechanical factors in fate decisions of stem cells." Regenerative medicine vol. 6, pp. 229-240, (2011).
Semrau et al., "Studying lineage decision-making in vitro; emerging concepts and novel tools." Annual review of cell and developmental biology vol. 31, pp. 317-345, (2016).
Shreiner et al., "The gut microbiome in health and in disease." Current opinion in gastroenterology vol. 31, pp. 69, (2015).
Terryn et al., "Recent advances in lineage differentiation from stem cells: hurdles and opportunities?" F1000Resarch vol. 7, (2018).
Tong et al., "Towards a defined ECM and small molecule based monolayer culture system for the expansion of mouse and human intestinal stem cells." Biomaterials vol. 154, pp. 60-73, (2018).

(56) References Cited

OTHER PUBLICATIONS

Tremlett et al., "The gut microbiome in human neurological disease: a review." Annals of Neurology, (2017).
Tsubouchi, "Kinetic analysis of epithelial cell migration in the mouse descending colon." Developmental Dynamics, vol. 161, pp. 239-246, (1981).
Van Es et al., "DII1+ secretory progenitor cells revert to stem cells upon crypt damage." Nature cell biology vol. 14, pp. 1099, (2012).
Wang et al., "In vitro Generation of Mouse Colon Crypts." ACS biomaterials science & engineering vol. 3, pp. 2502-2513, (2017).
Whitehead et al., "Effects of short-chain fatty acids on a new human colon carcinoma cell line (LIM1215)." Gut, vol. 27, pp. 1457-1463, (1986).
Young, "The role of the microbiome in human health and disease: an introduction for clinicians." BMJ vol. 356, j831, (2017).
Xu et al., "Butyrate induces apoptosis by activating PDC and inhibiting complex I through SIRT3 inactivation." Signal Transduction and Targeted Therapy, vol. 2, pp. e16035, (2017).
Fung et al., "Butyrate-Induced Apoptosis in HCT116 Colorectal Cancer Cells Includes Induction of a Cell Stress Response." Journal of Proteome Research, vol. 10, pp. 1860-1869 (2011).
Ruemmele et al., "Butyrate induced Caco-2 cell apoptosis is mediated via the mitochondrial pathway." Gut, vol. 52, pp. 94-100, (2003).
Koh et al., "From Dietary Fiber to Host Physiology: Short-Chain Fatty Acids as Key Bacterial Metabolites." Cell, vol. 165, pp. 1332-1345, (2016).
Barker, "Adult intestinal stem cells: critical drivers of epithelial homeostasis and regeneration." Nature Reviews Molecular Cell Biology, vol. 15, pp. 19-33 (2014).
Sternini et al., "Enteroendocrine cells: a site of 'taste' in gastrointestinal chemosensing." Current Opinion in Endocrinology, Diabetes, and Obesity, vol. 15, pp. 73, (2008).
Birchenough et al., "A sentinel goblet cell guards the colonic crypt by triggering Nlrp6-dependent Muc2 secretion." Science, vol. 352, pp. 1535-1542, (2016).
Valenta et al., "The many faces and functions of B-catenin." The EMBO Journal, vol. 31, pp. 2714-2736, (2012).
Provenzano and Keely, "Mechanical signaling through the cytoskeleton regulates cell proliferation by coordinated focal adhesion and Rho GTPase signaling", J. Cell Sci, vol. 124, pp. 1195-1205, (2011).
Yim and Sheetz, "Force-dependent cell signaling in stem cell differentiation." Stem Cell Research & Therapy, vol. 3, pp. 41, (2012).
Lü et al., "Differential regulation of morphology and stemness of mouse embryonic stem cells by substrate stiffness and topography," Biomaterials, vol. 35, pp. 3945-3955, (2014).
Chowdhury et al., "Soft Substrates Promote Homogeneous Self-Renewal of Embryonic Stem Cells via Downregulating Cell-Matrix Tractions." PloS one, vol. 5, e15655, (2010).
Janshoff et al., "Cell Adhesion to Ordered Pores: Consequences for Cellular Elasticity." Journal of Adhesion Science and Technology, vol. 24, pp. 2287-2300, (2010).
Rother et al., "Cytoskeleton remodelling of confluent epithelial cells cultured on porous substrates." Journal of the Royal Society Interface, vol. 12, 20141057, (2015).
Hayman et al., "Growth of human stem cell-derived neurons on solid three-dimensional polymers." Journal of Biochemical and Biophysical Methods, vol. 62, pp. 231-240, (2005).
Peyton et al., "Marrow-Derived Stem Cell Motility in 3D Synthetic Scaffold Is Governed by Geometry Along With Adhesivity and Stiffness." Biotechnology and Bioengineering, vol. 108, pp. 1181-1193, (2011).
Ahmad et al., "Optimizing Wnt-3a and R-spondin1 concentrations for stem cell renewal and differentiation in intestinal organoids using a gradient-forming microdevice." RSC Advances, vol. 5, pp. 74881-74891 (2015).
Franck et al., "Three-Dimensional Traction Force Microscopy: A New Tool for Quantifying Cell-Matrix Interactions." PloS one, vol. 6, e17833, (2011).
Qu et al., "Maturation State and Matrix Microstructure Regulate Interstitial Cell Migration in Dense Connective Tissues." Scientific Reports, vol. 8, 3295, (2018).
Vallo et al., "Elastic Modulus and Yield Stress of Epoxy Networks in the Glassy State." Polymer Gels and Networks, vol. 1, pp. 257-266, (1993).
Engelberg and Tesoro, "Mechanical and Thermal Properties of Epoxy Resins With Reversible Crosslinks," Polymer Engineering & Science, vol. 30, pp. 303-307, (1990).
Faul et al., "G*Power 3: A flexible statistical power analysis program for the social, behavioral, and biomedical sciences," Behavior Research Methods, vol. 39, pp. 175-191, (2007).
Schindelin et al., "Fiji—an Open Source platform for biological image analysis." Nature Methods, vol. 9, pp. 676, (2012).
Pai et al., "Photoresist with Low Fluorescence for Bioanalytical Applications," Analytical Chemistry, vol. 79, pp. 8774-8780, (2007).
Allen et al., "Adherent and soluble Mucus in the Stomach and Duodenum." Digestive Diseases and Sciences vol. 30, 55S-62S, (1985).
Pelaseyed et al., "The mucus and mucins of the goblet cells and enterocytes provide the first defense line of the gastrointestinal tract and interact with the immune system." Immunological reviews vol. 260, pp. 8-20, (2014).
Murgia et al., "The role of mucus on drug transport and its potential to affect therapeutic outcomes." Adv Drug Deliv Rev vol. 124, pp. 82-97, (2018).
Lehr et al., "An estimate of turnover time of intestinal mucus gel layer in the rat in situ loop." International Journal of Pharmaceutics vol. 70 pp. 235-240, (1991).
Wei et al., "Fatty Acid Synthase Modulates Intestinal Barrier Function through Palmitoylation of Mucin 2." Cell Host & Microbe vol. 11, pp. 140-152, (2012).
Johansson et al., "The inner of the two Muc2 mucin-dependent mucus layers in colon is devoid of bacteria." Proceedings of the National Academy of Sciences of the United States of America, vol. 105, pp. 15064-15069, (2008).
Hansson, "Role of mucus layers in gut infection and inflammation." Current Opinion in Microbiology vol. 15, pp. 57-62, (2012).
Carlson et al., "Engineering the Mucus Barrier." Annual Review of Biomedical Engineering vol. 20, pp. 197-220, (2018).
Werlang et al., "Engineering mucus to study and influence the microbiome." Nature Reviews Materials vol. 4, pp. 134-145, (2019).
Rogier et al., "Secretory IgA is Concentrated in the Outer Layer of Colonic Mucus along with Gut Bacteria." Pathogens vol. 3, pp. 390-403, (2014).
Gunasekara et al., "A Monolayer of Primary Colonic Epithelium Generated on a Scaffold with a Gradient of Stiffness for Drug Transport Studies." Analytical Chemistry vol. 90, pp. 13331-13340, (2018).
Quigley, "Gut bacteria in health and disease." Gastroenterology & hepatology vol. 9, pp. 560-569, (2013).
Gagnon et al., "Comparison of the Caco-2, HT-29 and the mucus-secreting HT29-MTX intestinal cell models to investigate Salmonella adhesion and invasion," Journal of Microbiological Methods, vol. 94, pp. 274-279 (2013).
Lesuffleur et al., "Growth adaptation to methotrexate of HT-29 human colon carcinoma cells is associated with their ability to differentiate into columnar absorptive and mucus-secreting cells." Cancer Research vol. 50, pp. 6334-6343, (1990).
Nusrat et al., "Clostridium difficile Toxins Disrupt Epithelial Barrier Function by Altering Membrane Microdomain Localization of Tight Junction Proteins." Infection and Immunity vol. 69, pp. 1329-1336, (2001).
Date et al., "Mini-Gut Organoids: Reconstitution of Stem Cell Niche." Annual Review of Cell and Developmental Biology vol. 31, pp. 269-289, (2015).
Sato et al., "Long-term Expansion of Epithelial Organoids From Human Colon, Adenoma, Adenocarcinoma, and Barrett's Epithelium." Gastroenterology vol. 141, pp. 1762-1772, (2011).

(56) References Cited

OTHER PUBLICATIONS

Fatehullah et al., "Cell and tissue polarity in the intestinal tract during tumourigenesis: cells still know the right way up, but tissue organization is lost." Philosophical Transactions of the Royal Society B-Biological Sciences vol. 368, 20130014, (2013).
Noel et al., "A primary human macrophage-enteroid co-culture model to investigate mucosal gut physiology and host pathogen interactions." Scientific Reports vol. 7, pp. 45270, (2017).
Puzan et al., "Enteric Nervous System Regulation of Intestinal Stem Cell Differentiation and Epithelial Monolayer Function." Scientific Reports vol. 8, pp. 6313, (2018).
Wang et al., "Analysis of Interleukin 8 Secretion by a Stem-Cell-Derived Human-Intestinal-Epithelial-Monolayer Platform." Analytical Chemistry vol. 90, pp. 11523-11530, (2018).
Whitcutt et al., "A biphasic chamber system for maintaining polarity of differentiation of cultured respiratory tract epithelial cells." In Vitro Cellular & Developmental Biology, vol. 24, pp. 420-428, (1988).
Gray et al., "Mucociliary differentiation of serially passaged normal human tracheobronchial epithelial cells," American Journal of Respiratory Cell and Molecular Biology, vol. 14, pp. 104-112 (1996).
Raredon et al., "A Rotating Bioreactor for Scalable Culture and Differentiation of Respiratory Epithelium." Cell Medicine vol. 7, pp. 109-121, (2012).
O'Boyle et al., "Temporal dynamics of ovine airway epithelial cell differentiation at an air-liquid interface." Plos One vol. 12, e0181583, (2017).
Ootani et al., "An air-liquid interface promotes the differentiation of gastric surface mucous cells (GSM06) in culture." Biochemical and Biophysical Research Communications vol. 271, pp. 741-746, (2000).
Yokoyama et al., "Differentiation of gastric surface mucous cells (GSM06) induced by air-liquid interface is regulated partly through mitogen-activated protein kinase pathway." Journal of Gastroenterology and Hepatology, vol. 22, pp. 2310-2315, (2007).
Navabi et al., "Gastrointestinal Cell Lines Form Polarized Epithelia with an Adherent Mucus Layer when Cultured in Semi-Wet Interfaces with Mechanical Stimulation." Plos One vol. 8, e68761, (2013).
Elkins et al., "Mechanisms and applications of hypertonic saline." Journal of the Royal Society of Medicine, vol. 104, pp. S2-S5, (2011).
Tu et al., "Effect of osmotic response element binding protein on mucus secretion with hypertonicity in human airway epithelial cells," Zhonghua Yi Xue Za Zhi, vol. 91, pp. 549-553, (2011) [English Abstract].
Lüdeking et al., "Osmotic changes and ethanol modify TFF gene expression in gastrointestinal cell lines." Febs Letters vol. 439, pp. 180-184, (1998).
Shields et al., "Absorption and secretion of water and electrolytes by the intact colon in a patient with primary aldosteronism." British Medical Journal vol. 1, pp. 93-96, (1968).
Wapnir et al., "Regulation mechanisms of intestinal secretion: implications in nutrient absorption." The Journal of Nutritional Biochemistry vol. 13, pp. 190-199, (2002).
Koch et al., "Plasma vasoactive intestinal polypeptide concentration determination in patients with diarrhea." Gastroenterology vol. 100, pp. 99-106, (1991).
Schwartz et al., "Vasoactive intestinal peptide stimulation of adenylate cyclase and active electrolyte secretion in intestinal mucosa." Journal of Clinical Investigation vol. 54, pp. 536-544, (1974).
Wu et al., "Vasoactive Intestinal Polypeptide Promotes Intestinal Barrier Homeostasis and Protection Against Colitis in Mice." Plos One vol. 10, e0125225, (2015).
Johansson et al., "Bacteria penetrate the normally impenetrable inner colon mucus layer in both murine colitis models and patients with ulcerative colitis." Gut, vol. 63, pp. 281-291, (2014).
Lin et al., "Air-liquid interface (ALI) culture of human bronchial epithelial cell monolayers as an in vitro model for airway drug transport studies." Journal of Pharmaceutical Sciences vol. 96, pp. 341-350, (2007).
Bernstam et al., "Keratinocytes grown at the air-liquid interface." In Vitro Cellular & Developmental Biology vol. 22, pp. 695-705, (1986).
Ootani et al., "Sustained in vitro intestinal epithelial culture within a Wnt-dependent stem cell niche." Nature Medicine vol. 15, pp. 1-U140, (2009).
Voth et al., "Clostridium difficile toxins: mechanism of action and role in disease." Clinical microbiology reviews vol. 18, pp. 247-263, (2005).
He et al., "Clostridium difficile toxin A triggers human colonocyte IL-8 release via mitochondrial oxygen radical generation." Gastroenterology, vol. 122, pp. 1048-1057, (2002).
Mahida et al., "Effect of Clostridium difficile toxin A on human intestinal epithelial cells: induction of interleukin 8 production and apoptosis after cell detachment." Gut vol. 38, pp. 337-347, (1996).
Haller et al., "Non-pathogenic bacteria elicit a differential cytokine response by intestinal epithelial cell/leucocyte co-cultures." Gut vol. 47, pp. 79-87, (2000).
Parlesak et al., "Modulation of Cytokine Release by Differentiated CACO-2 Cells in a Compartmentalized Coculture Model with Mononuclear Leucocytes and Nonpathogenic Bacteria." Scandinavian Journal of Immunology vol. 60, pp. 477-485, (2004).
English Translation of Notice of Allowance corresponding to JP Patent Application No. JP 2017-540628 dated Jun. 29, 2021.
English Translation of First Office Action corresponding to JP Patent Application No. JP 2019-504019 dated May 25, 2021.
Canadian Office Action for Application No. 3052250 dated May 12, 2023.
Japanese Office Action for Application No. 2022560193 dated Apr. 25, 2023.
Japanese Office Action for Application No. 2020565308 dated Apr. 18, 2023.
Crank et al., "The Mathematics of Diffusion," Clarendon Press: 421 pages (1979).
Crosnier et al., "Organizing cell renewal in the intestine: stem cells, signals and combinatorial control," Nature Reviews Genetics, vol. 7: 349-359 (2006).
Flier et al., "Stem Cells, Self-Renewal, and Differentiation in the Intestinal Epithelium," Annual Review of Physiology, vol. 71: 241-260 (2009)—Abstract.
Galland, "The gut microbiome and the brain," Journal of Medicinal Food, vol. 17: 1261-1272 (2014).
Goldszmid et al., "The price of immunity," Nature Immunology, vol. 13: 932-938 (2012).
Leonel et al., "Butyrate: Implications for intestinal function," Current Opinion in Clinical nutrition & Metabolic Care, vol. 15: 474-479 (2012).
Ren et al., "Short-Chain Fatty Acids Induce Intestinal Epithelial Heat Shock Protein 25 Expression in Rats and IEC 18 Cells," Gastroenterology, vol. 121: 631-639 (2001).
Takano et al., "Microfluidic cell culture system with on-chip hypoxic conditioning," In: Engineering in Medicine and Biology Society (EMBC), 35th Annual International Conference of the IEEE EMBS: 4474-4477 (2013).
Japanese Office Action in JP Application No. 2022-559825, dated Apr. 1, 2025, 4 pages.
Canadian Office Action in CA Application No. 3093585, dated Apr. 25, 2025, 6 pages.
Japanese Office Action in JP Application No. 2024-033959 dated Jun. 10, 2025, 3 pages.

\* cited by examiner

IN VITRO CELL CULTURE MUCUS SYSTEMS

CROSS REFERENCE TO RELATED APPLICATIONS

This application claims priority to International Patent Application No. PCT/US2019/061743, filed Nov. 15, 2019, which claims the benefit of and priority to U.S. Provisional Patent Application Ser. No. 62/768,259, filed Nov. 16, 2018, the disclosures of each of which are incorporated herein by reference in its entirety their entireties.

STATEMENT OF GOVERNMENT SUPPORT

This invention was made with government support under grant number DK109559 awarded by National institutes of Health. The government has certain rights to this invention.

TECHNICAL FIELD

The present disclosure relates to an in vitro cell culture comprising a cell monolayer comprising mucus producing cells and a mucus layer, and methods of making and using the same.

BACKGROUND

The luminal surfaces of the small and large intestine are protected by a thick blanket of mucus. The small intestine produces a 50 to 450 µm single layer of mucus, while the large intestinal mucus coating is composed of two structurally distinct layers.[1] The 400 to 800 µm outer mucosal layer is loosely packed, providing a hospitable environment for bacteria to inhabit, while the 100 to 300 µm inner mucosal layer remains impenetrable to bacteria and firmly attached to the epithelium.[2,3] In both organs, mucus is continuously generated and secreted by goblet cells lining the intestinal epithelium. The mucus layer above the cells is estimated to be replaced on the order of a few hours.[4] Mucin 2 (Muc2) is the most abundant gel-forming component of intestinal mucus.[5] A mucus layer is essential to sustain the homeostasis of the colonic mucosa in vivo. The main functions of the mucus layer are to serve as a barrier to protect the underlying epithelium from pathogen invasion, as well as to keep the lining of the colon lubricated and moist due to the high concentration of water (about 97%) present in mucus.[6,7] The mucus layer also acts as a barrier to hinder diffusion of molecules derived from food or bacteria and their metabolites, and traps molecules such as secretory IgA (sIgA) and anti-bacterial peptides secreted by intestine.[8]

In vitro intestinal epithelium models provide a valuable tool to study the highly complicated intestinal epithelium system under a controlled manner. Adenocarcinoma cell lines including Caco-2 and HT-29 are widely used as in vitro models of the intestinal epithelium, but they do not produce dense mucus layers.[9] HT29-MTX, a stable homogenous subpopulation of HT-20 derived after treatment with methotrexate, is often used as a mucus-secreting cell model.[10] However, these tumor cells do not possess normal signaling pathways, physiologic mucus secretion, or appropriate responses to external stimuli. In recent years, breakthroughs in intestinal stem cell biology permit building in vitro models based on primary intestinal epithelial stem cells.[11] The organoid culture model, for the first time, realized the in vitro expansion and lineage manipulation of adult intestinal epithelial stem cells, and the generated "mini-gut" organoids possess the diversity of cell lineages found in in vivo epithelium, including mucus-secreting goblet cells.[11-14] The cells are polarized so that their apical surface faces to the enclosed lumen and their basal sides are attached to Matrigel® or other ECM components.[15] Mucus, however, is secreted into and accumulated within the organoids' lumen which is surrounded by a layer of cells as well as a dense hydrogel such as Matrigel® or collagen. This mucus secretion is not readily quantified or manipulated nor does the mucus act as a barrier to external stimuli.

In attempts to expose the luminal surface, monolayer models have been built by culturing the intestinal epithelial stem cells (e.g. from isolated crypts, or dissociated organoid fragments) on porous membranes coated with either a thick or thin layer of extracellular matrix.[16-23] The cells proliferated in the presence of growth factors (Wnt-3A, R-spondin and noggin), and differentiated in the absence of growth factors to form continuous monolayers possessing a physiologic transepithelial electrical resistance (TEER). Monolayers possess a unique advantage over organoids with their open luminal surface, which allows easy access to the apical epithelium to assay the impact, absorption or metabolism of food components, microorganisms, bioactive metabolites, drugs, and toxic compounds. The monolayer model has been used to study IgA transcytosis,[16] co-culture with bacteria,[17,18] iron transport,[19] hormone secretion,[19] co-culture with macrophages,[20] co-culture with myofibroblasts and enteric neurons,[21] and cytokine secretion.[20,21] In all of the above reported monolayer models of primary cells, the cells were in a submerged culture system, i.e. aqueous medium was placed into the basal and luminal reservoirs. Traces of mucus were identified by staining with Muc2 antibody.[18] The mucus thickness was measured by overlaying the cells with fluorescent microbeads and measuring the distance between the cells and beads which are too large to penetrate the mucus.[16] However, the mucus layer was not continuous,[18] nor thick enough to separate the microbeads from the epithelium.[16] Thus the beads appear to be in contact with the apical epithelial surface within the resolution of the microscopic images. However, Muc2 was detected in the supernatant above the cells suggesting that some amount of Muc2 was synthesized and secreted but not in sufficient quantities or densities to recreate a mucus layer.[24]

Thus, a dense mucus layer that is substantially microbead or bacterial-impenetrable with a controllable thickness has not yet been achieved in any in vitro intestinal epithelium models constructed from primary intestinal epithelial cells. Such an in vitro model is needed to reflect in vivo conditions.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are methods of producing a live cell construct comprising a cell monolayer comprising mucus producing cells and a mucus layer, comprising culturing stem cells that are capable of differentiating into mucus producing cells (e.g., intestinal epithelial stem cells, basal stem cells, induced pluripotent stem cells and the like) on an upper surface of a cell support structure having both an upper surface and a lower surface until at least a portion of the upper surface of the cell support structure is covered by the stem cells, and culturing the stem cells further to produce a cell monolayer comprising mucus producing cells (e.g., goblet cells GC) and other cell types (OC, including enterocytes, enteroendocrine cells, Paneth cells, stem cells, etc.), the cell monolayer having a basal side and a luminal (apical) side, wherein the mucus producing cells of the cell monolayer establish a mucus layer on the luminal side of the cell monolayer, thereby producing a live cell construct comprising a cell monolayer comprising mucus producing cells and a mucus layer. The mucus layer can be substantially or completely impenetrable to micro-objects. In some aspects, the thickness of the mucus layer can be about 1 micron to about 1 cm. In some embodiments, the thickness of the mucus layer can be about 30 microns to about 1 cm. The ratio of GC to OC can in some embodiments range from about 0.1% to about 99.9%.

In some embodiments, a basal reservoir is present below the basal side of the cell monolayer comprising mucus producing cells and a luminal reservoir is present above the luminal side of the cell monolayer comprising mucus producing cells, and the basal reservoir and the luminal reservoir each comprise a liquid medium; the method further comprising: removing the liquid medium in the luminal reservoir to produce an air-liquid interface at the luminal side of the cell monolayer that comprises mucus producing cells, and/or adjusting the volume of the liquid medium in the luminal reservoir to a depth in a range of about 0.001 mm to about 10 mm, optionally about 0.001 mm to about 1 mm, above the luminal side of the cell monolayer (wherein the mucus layer is (or develops) between the liquid medium and the cell monolayer). In some embodiments, the methods can further comprise positioning an impermeable physical barrier and/or a partially permeable physical barrier on or above the luminal side of the cell monolayer comprising mucus producing cells. In some aspects, the impermeable physical barrier and/or the partially permeable physical barrier is in direct contact with the luminal side of the cell monolayer comprising mucus producing cells and/or the mucus layer produced by the mucus producing cells of the cell monolayer. The liquid medium can be between the impermeable physical barrier and/or the partially permeable physical barrier and the luminal side of the cell monolayer comprising mucus producing cells and/or the mucus layer and the depth of the liquid medium is in a range of about 0.001 mm to about 10 mm, optionally about 0.001 mm to about 1 mm. In some embodiments, the liquid medium comprises a hormone, a chemical additive, a food additive, bacterial metabolite, and/or a hypertonic salt solution, wherein the hormone, the chemical additive, the food additive, the bacterial metabolite, and/or the hypertonic salt solution. In some embodiments, the stem cells are epithelial stem cells, intestinal epithelial stem cells, basal stem cells, induced pluripotent stem cells, respiratory stem cells, gastric stem cells, nasal stem cells, reproductive tract cells (cervix, vagina, uterus), urethra cells, olfactory cells, mouth cells, tongue cells, and/or conjunctiva cells. In some embodiments, the stem cells are intestinal epithelial stem cells. The mucus layer can be substantially impenetrable to beads or microorganisms in a size range from about 1 to about 100 microns.

In some embodiments, a force is applied parallel to the surface of the cell monolayer. In some embodiments, the force comprises application of a surface tension force or application of a mechanical force. In some embodiments, the mechanical force is a stir bar, a semi-solid material moving parallel to the cell surface, and/or circulation of a slurry on the top of cell surface.

In some embodiments, provided herein is a live cell construct comprising a cell monolayer comprising mucus producing cells and a mucus layer produced by the methods disclosed herein. In some embodiments, the mucus layer comprises a basal side and a luminal side, wherein the basal side is below and adjacent to the mucus producing cells.

In some embodiments, provided herein are live cell constructs comprising a cell monolayer comprising mucus producing cells and a mucus layer, wherein the mucus layer is substantially impenetrable to micro-objectives. The mucus layer can comprise a thickness of about 1 micron to about 1 cm. The mucus layer can be impenetrable to micro-objects in a size range from about 1 micron to about 100 microns. In some embodiments, the mucus layer can comprise a basal side and a luminal side, wherein the basal side is below and adjacent to the mucus producing cells.

In some embodiments, provided herein are methods of determining the ability of an organism, a drug, or a particle to traverse (penetrate) a mucus layer of a cell monolayer, the method comprising contacting the luminal side of the mucus layer of the live cell construct disclosed herein with the organism, drug, or particle, and measuring the distance that the organism, drug, or particle moves into the mucus layer, thereby determining the ability of the organism, drug or particle to traverse (penetrate) the mucus layer of the cell monolayer of the live cell construct.

In some embodiments, provided herein are methods of studying and evaluating an organism's ability to infect a cell monolayer comprising a mucus layer, comprising contacting the luminal side of the mucus layer of the live cell construct disclosed herein with the organism, and determining if the organism traverses the mucus layer and contacts the cell monolayer of the live cell construct, wherein when the organism is determined to traverse the mucus layer and contact the cell monolayer, the organism is determined to be able to infect the cell monolayer comprising a mucus layer.

In some embodiments, provided herein are methods of evaluating the effectiveness of a drug to prevent or reduce infection by an organism, comprising contacting the luminal side of the mucus layer of the live cell construct disclosed herein with the organism, contacting the luminal side of the mucus layer of the live cell construct with the drug, and determining whether the organism penetrates the mucus layer of the cell monolayer and/or infects one or more the cells of the cell monolayer of the live cell construct, wherein the drug is determined to be effective for preventing or reducing infection if the organism does not penetrate the mucus layer and/or infect one or more cells of the cell monolayer of the live cell construct and is determined to not be effective if the organism penetrates the mucus layer and/or infect one or more cells of the cell monolayer of the live cell construct as compared to a control (i.e., contacted with the organism but no drug). Contacting the organism with the luminal side of the mucus layer of the live cell construct can be prior to, concurrent with, or after contacting the drug with the luminal side of the mucus layer of the live cell construct.

In some embodiments, provided herein are methods of evaluating an immunological response of a cell comprising a mucus layer to invasion by an organism, contact by a particle, and or contact by a chemical/compound, comprising contacting the luminal side of the mucus layer of the live cell construct disclosed herein with the organism, particle and or chemical/compound, and assaying cells of the cell monolayer of the live cell construct for the production of a marker associated with an immune response (e.g., a cytokine, a chemokine, a hormone, a neurotransmitter, and/or a antimicrobial peptide), thereby evaluating the immunological response of the cell monolayer of the live cell construct to contact by the organism, particle and or chemical/compound. The organism can be a bacterium, a virus, a fungus, protozoan, and/or a helminth.

In some embodiments, disclosed herein are methods of evaluating mucus misregulation in an in vitro cell system, comprising studying the mucus layer of the live cell construct disclosed herein, wherein the stem cells that are cultured are from a subject having a disease associated with mucus misregulation and/or the stem cells that are cultured are from a healthy subject and are gene edited to recapitulate stem cells from a disease associated with mucus misregulation; and studying comprises evaluating the mucus layer of the live cell construct for thickness, composition, viscosity, degree of penetration by micro-objects, ability of microorganisms to infect, and/or responsiveness to drugs; thereby evaluating mucus misregulation in an in vitro cell system. In some embodiments, a disease associated with mucus misregulation is inflammatory bowel disease, constipation, cystic fibrosis irritable bowel syndrome, leaky gut syndrome, bacterial overgrowth syndromes, celiac disease, lactose intolerance, excessive gas syndromes, diarrheal diseases, and/or polyps appendicitis.

The foregoing and other objects and aspects of the present disclosure are explained in detail in the specification set forth below.

Embodiments of the presently disclosed subject matter having been stated hereinabove, and which are achieved in whole or in part by the presently disclosed subject matter, other embodiments will become evident as the description proceeds when taken in combination with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIG. 1A provides an air-liquid interface (ALI) culture. The apical side is exposed to air and the liquid or medium has been removed allowing mucus to accumulate in a compacted form. FIG. 1B illustrates a modified ALI culture. The volume of liquid is controlled at the apical side allowing mucus to accumulate in a compacted form and having increased hydration. FIG. 1C illustrates an example of use of a scaffold in place of a porous membrane. FIG. 1D provides an example of use of a partially permeable physical barrier (separator) to confine accumulated mucus. FIG. 1E illustrates an example of use of an impermeable physical barrier (blocker) to control mucus accumulation.

FIG. 2A is a schematic showing the submerged and ALI culture formats, including stem cells (SC), mucus producing goblet cells (GC), other non-mucus producing cells (OC), and mucins (or diluted mucins) (M). FIG. 2B shows immunofluorescence staining of cross sections through paraffin-embedded monolayers (Muc2 and nuclei labelled). Arrows demarcate goblet cells. A: apical side; B: basal side. The lower panels (i, ii and iii) show higher magnification regions as marked by the corresponding dotted line boxes in the upper two panels. FIG. 2C shows apical surface topography of human colonic monolayers inspected by SEM. Top panel: submerged culture. Bottom panel: ALI culture. In FIGS. 2D and 2E the mucus layer was overlaid with 1 μm red fluorescent beads (FIG. 2D) or GFP-expressing $E.\ coli$ (FIG. 2E) for visualization by confocal microscopy. The nuclei of intestinal cells were stained with Hoechst 33342. The dashed line shows the boundary between the mucus and microbeads or $E.\ coli$.

FIGS. 3A through 3G show that a hydrated mucus layer separates bacteria or microbeads from epithelium incubated with vasoactive intestinal peptide (VIP). FIG. 3A is a schematic showing the culture format. VIP facilitates the water movement into the lumen or luminal side LS which hydrates the mucus layer. FIG. 3B is a graphical depiction of data showing the concentration-dependent water secretion by VIP after 24 h of incubation. FIG. 3C is an image of the hydrated mucus layer lifted off the epithelium by forceps. FIG. 3D includes representative side-view confocal micrographs showing tissues with bacteria-separating mucus accumulation at 0, 2, 4 and 6 days, respectively. GFP-expressing $E\ coli$ and nuclei are labelled. FIG. 3E is a plot of mucus thickness versus duration of ALI. FIG. 3F is a representative side-view confocal micrograph showing the mucus layer separated 1 μm red fluorescent beads from epithelium. FIG. 3G shows images of apical surface topography of the epithelium inspected by SEM. The mucus layer was partially removed to reveal the epithelium (dashed line). The upper right panel shows bacteria (rod-shaped structures) above the mucus layer and absent from the epithelial surface.

FIG. 4A is a schematic illustration showing the cell culture systems. FIGS. 4B and 4C show permeability (FIG. 4B) and IL-8 secretion (FIG. 4C) of epithelium after 4-h exposure to toxin A. FIG. 4D shows confocal microscopic images showing F-actin architecture in the apical membrane (top panel) and ZO-1 staining tight junctions (bottom panel). FIGS. 4E and 4F show permeability (FIG. 4E) and IL-8 secretion (FIG. 4F) of epithelium after 8-h exposure to toxin A. Unpaired t test: * P<0.05; ** P<0.005; # not statistically significant. N=3 samples per condition. Scale bar=20 µm.

FIG. 5A is a schematic illustration showing the co-culture setup. The graphical depictions of FIGS. 5B through 5E show the production of cytokines at the basal side for 24 h: (FIG. 5B) IL-8, (FIG. 5C) TNF-α, (FIG. 5D) IL-6 and (FIG. 5E) IL-1β. Unpaired t test: ** P<0.005; # not statistically significant. N=3 samples per condition.

DETAILED DESCRIPTION

Figure 1A:
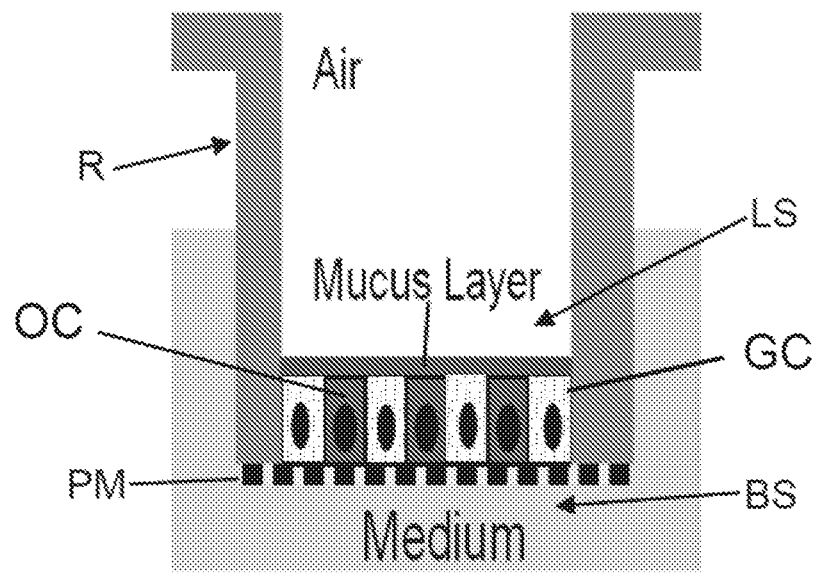
FIGS. 1A through 1E provide schematics of systems and methods according to the present disclosure for generating an in vitro mucus layer.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

Unless otherwise defined, all technical and scientific terms used herein have the same meaning as commonly understood by one of ordinary skill in the art to which this presently disclosed subject matter belongs. The terminology used in the description of the presently disclosed subject matter herein is for the purpose of describing particular embodiments only and is not intended to be limiting of the presently disclosed subject matter.

All publications, patent applications, patents and other references cited herein are incorporated by reference in their entireties for the teachings relevant to the sentence and/or paragraph in which the reference is presented.

Unless the context indicates otherwise, it is specifically intended that the various features of the presently disclosed subject matter described herein can be used in any combination. Moreover, the presently disclosed subject matter also contemplates that in some embodiments of the presently disclosed subject matter, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Like numbers refer to like elements throughout. In the figures, the thickness of certain lines, layers, components, elements or features can be exaggerated for clarity. Where used, broken lines illustrate optional features or operations unless specified otherwise.

As used in the description of the presently disclosed subject matter and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value can include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, can be used herein for ease of description to describe an element's or feature's relationship to another element(s) or feature(s) as illustrated in the figures.

It will be understood that, although the terms first, second, etc., can be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the presently disclosed subject matter. The sequence of operations (or steps) is not limited to the order presented in the claims or figures unless specifically indicated otherwise.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

As used herein, the term "micro-objects" means an object having a dimension of about 0.1-100 μm, which can be used to determine the penetrability of a mucus layer. Examples of micro-objects include, but are not limited to, microorganisms (e.g., bacteria) and micro-particles (e.g., beads).

The instant disclosure describes the discovery of methods of generating live cell constructs comprising cell monolayers comprising mucus producing cells and a mucus layer that recapitulates the in vivo mucus layer present in, for example, the intestinal tract and/or the reproductive tract of human and animal subjects. A thick, in vivo-like mucus barrier can be important for successful recreation of the gut environment for microbiota, as well as can serve as an in vitro tool to investigate mucosal drug and particle delivery. While mucus production has been observed previously in in vitro cell systems, these systems have not been able to produce mucus in sufficient quantities or densities to recreate a mucus layer that mimics the mucus layer found in in vivo settings. Without being limited to any particular theory, it is postulated herein that the mucus in these previous in vitro cell systems can be rapidly diluted after it is secreted from goblet cells in submerged culture systems, and therefore is unable to accumulate and form a dense layer (substantially impenetrable to microorganisms and micro-particles). As described herein, the presently disclosed subject matter overcomes these limitations.

In some embodiments, and as shown in FIGS. 1A through 1E, the present disclosure provides a live cell construct in a reservoir R comprising a cell layer that contains a combination or mixture of mucus-secreting goblet cells GC and other non-mucus producing cells OC, e.g. enterocytes, enteroendocrine cells, Paneth cells, stem cells, etc., the cells having a luminal side LS or apical side, as well as a basal side BS to the cells with a porous matrix (PM)/scaffold/base below the cells; and methods that facilitate mucus accumulation above the apical/luminal side LS of the cells to form a dense, in vivo-like mucus layer. The ratio of GC to OC can in some embodiments range from about 0.1% to about 99.9%. Thus, a cell monolayer in a live cell construct as disclosed herein can in some aspects comprise a mixture of mucus producing cells and non-mucus producing cells.

To generate a cell layer that contains mucus-secreting cells, epithelial stem cells are expanded on the surface of a porous membrane. The membrane can be coated with a thin (e.g., about 1 to 1,000 nanometers) extracellular matrix (ECM) or other chemical or with a thick (e.g., about 1 to about 100,000 micrometers) hydrogel scaffolding material (ECM or synthetic hydrogel) to support the cells. The cells are grown in media until a portion of the surface is covered with the cells. The stem cells SC can be allowed to spontaneously differentiate as they begin to cover the surface and/or consume nutrients in the adjacent medium. Alternatively, the cells can be switched to a different media that encourages the formation of mucus producing cells (e.g., goblet cells (GC)) and other cell types (OC) or chemical additives can be incorporated into the media to induce differentiation (e.g., butyrate, bone morphogenetic protein (BMP), gamma secretase inhibitors (e.g. DAPT, LY411575, dibenzazepine), etc.

Figure 2A:
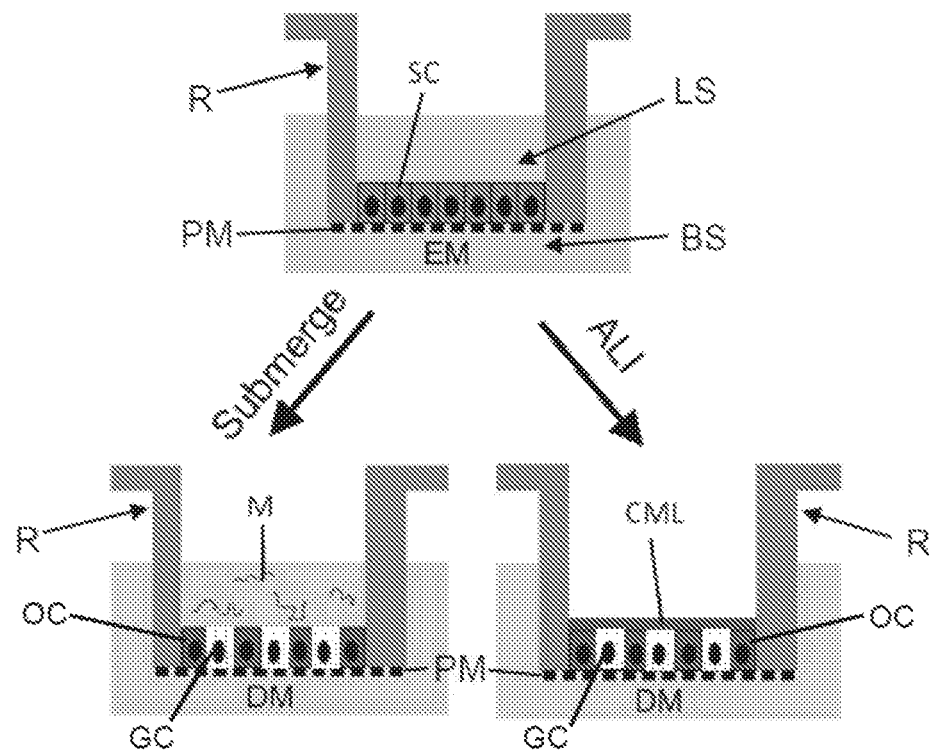
FIGS. 2A through 2E provide schematic illustrations of the creation of a compact mucus layer removal of liquid from the apical epithelial side (ALI culture), and resulting data.

A mucus layer can then be established on the apical cell side/luminal cell side LS using different methods as illustrated in FIGS. 2A through 2E. For example, as shown in FIG. 2A, an air-liquid interface (ALI) culture can be prepared in which liquid or medium is removed from the apical reservoir, or luminal side LS, or luminal reservoir. The ALI conditions permit mucus accumulation above the mucus producing goblet cells GC and/or OC (forming the epithelium) along the apical surface on the luminal side LS (as opposed to the basal side BS) in a dense compacted layer, or compacted mucus layer CML. In some embodiments, an ALI condition can allow the accumulation of a dense or concentrated mucus layer CML by (a) minimizing dilution of mucus that is secreted, (b) increasing forces on the cell surface due to surface tension or other effects (that promote mucus production and/or secretion), and/or (c) increasing local medium osmolality above the cells, etc. Movement of water through the mucus producing goblet cells GC) due to evaporation at their surface can also stimulate mucous production. See, Example 1.

Figure 1B:
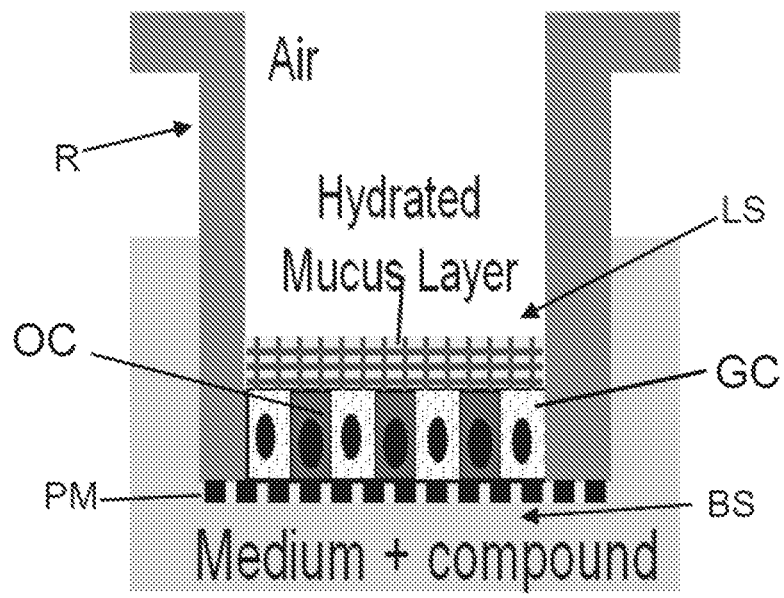

As another example, a modified ALI culture can be prepared as shown in FIG. 1B. This approach provides control of the height of the liquid medium on the apical/luminal side LS of the mucus producing cell monolayer, so that the mucus accumulated above the cell monolayer is dense, hydrated, and in vivo-like, i.e. a hydrated mucus layer. A liquid or medium depth in the range of about 0.001 mm to about 10 mm can be provided and maintained above the apical or luminal cell side LS so that the mucus, which accumulates over time is in a more hydrated state relative to that of ALI. The volume of liquid/medium in the luminal side LS of the reservoir R can be controlled to produce mucus with a range of mucus densities and compactness depending on the experimental needs.

In some embodiments, one or more materials or substances can be added to the apical surface or luminal side of the cells to assist in maintaining an aqueous film above the apical cell surface and can also be used to assist in programming or maintaining the desired liquid height over time. For example, a semi-liquid mass (e.g. hydrogels), a gas-impermeable membrane, a gas permeable membrane, and hygroscopic materials (honey, glycerin, sugar, nylon, ABS (acrylonitrile/butadiene/styrene), polycarbonate, cellulose, and poly(methyl methacrylate)) can be placed on the apical surface. Chemical reagents, hormones, food metabolites, bacterial products and other compounds can also be added to the culture system to assist in programming the desired fluid height and consequently also the mucus thickness and density. See, Example 2, where a hormone is added to the basal medium to promoting luminal water secretion.

Figure 1C:
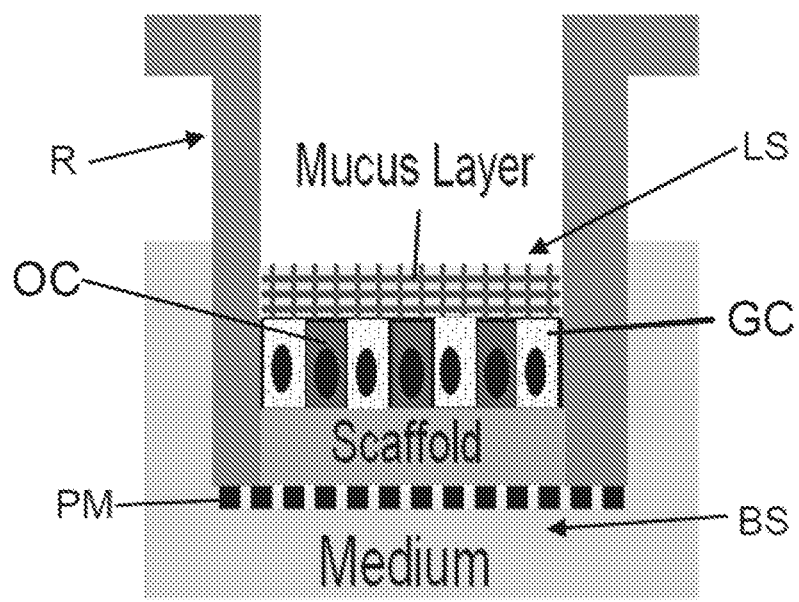

Turning now to FIG. 1C, in addition to the use of a porous membrane PM upon which a cell monolayer, e.g. differentiated epithelial cells, can be cultured, in some aspects such cells can be cultured or supported on a porous or nonporous scaffold. Examples of scaffolds that support a cell monolayer include, but are not limited to, hydrogel (natural and synthetic), porous material, nonporous material, plastic, ceramics, etc. Other examples include inorganic materials or a composite of organic and inorganic materials. Examples of inorganic materials suitable for supports include, but are not limited to, glass, hydroxyapatite, Bioglass such as 45S5 Bioglass, calcium phosphate, silicon, silicon oxide, titanium oxide, gold, aluminum oxide, etc. Where not inherently porous, these materials can be made porous by a variety of methods, including but not limited to, sintering, etching, leaching, lithography, etc. For example, a porous mesh of silicon and gold can be fabricated by lithography/etching. Such scaffolds can be supported on or placed adjacent to porous membrane PM.

Figure 1D:
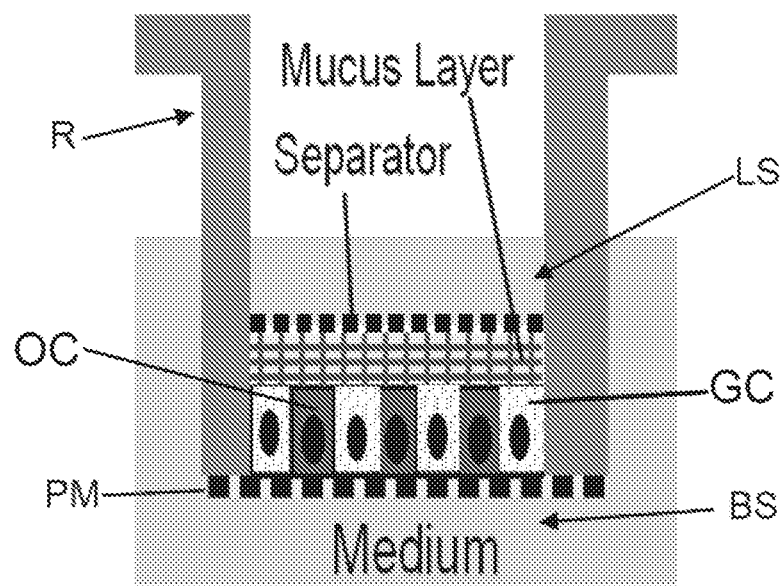

FIG. 1D shows the use of a separator (a semi-permeable/partially permeable physical barrier) that is positioned on the top of a cell monolayer on the luminal side LS within the reservoir R to prevent mucus dilution and assist in the formation of a dense layer of mucus. A separator can be impermeable to mucin but permeable to, for example, water. Examples of these separators include, but are not limited to, porous membrane, hydrogels (e.g. agarose, gelatin, collagen, Matrigel®, etc.), porous materials, semi-liquid masses, oils (e.g. mineral oils, perfluorocarbons, etc.), solid floaters (e.g. waxes, plastics, etc.), and meshes (nylon, photoresists, polydimethylsiloxane and other synthetic polymers, etc.). A separator can act as a diffusion barrier to the aqueous media/medium or to the mucus constituents.

Figure 1E:
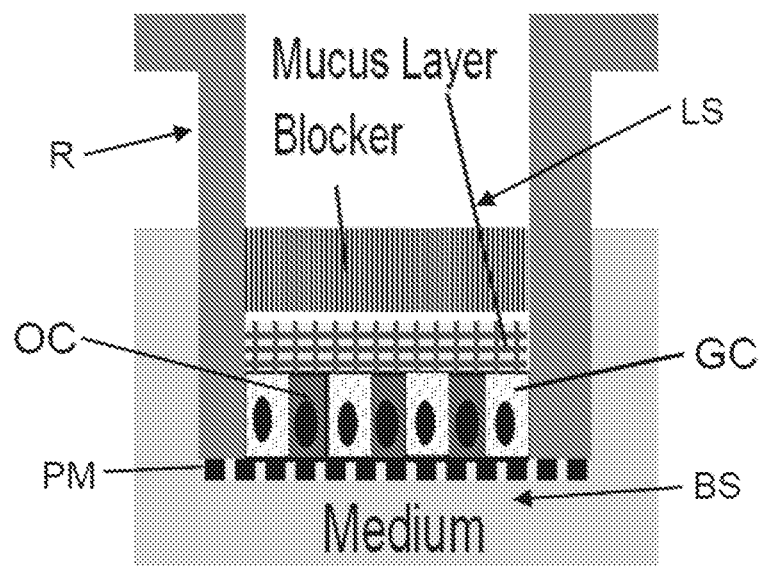

Alternatively, in some embodiments, an impermeable physical barrier (a blocker) can also be used, as shown in FIG. 1E, to facilitate the accumulation of a dense mucus layer. The impermeable physical barrier can be positioned on top of (above), i.e. on the luminal side LS, the mucus producing cell monolayer within the reservoir R. The impermeable physical barrier or blocker can be impermeable to mucins and to water so that it confines the mucus accumulation. Examples of blockers include, but are not limited to, hydrogels (e.g. agarose, gelatin, collagen, Matrigel®, etc.), porous materials, oils (e.g. mineral oils, perfluorocarbons, etc.), solid floaters (e.g. waxes, plastics, etc.), and meshes (nylon, photoresists, polydimethylsiloxane and other synthetic polymers, etc.).

Additional methods for generating dense mucus layers on the surface of mucus producing cell monolayers can be used to further enhance the density of the mucus layer. For example, in some embodiments, surface forces or mechanical stimulation can be applied to the surface of the cell monolayer comprising the mucus producing cells to mimic the impact of surface tension forces (without diluting the mucus) that can be present during meniscus formation generated by ALI. Mechanisms for exerting shear forces in a non-dilutive manner can include, but are not limited to, stir bars, mechanical rotation of a layer or material above the cells, back and forth movements parallel to the surface induced by a viscous layer overlaid on the cell surface (this can include providing a rocking motion such as with a mechanical rocker). Mechanical stimulation also can be applied to the cell surface, e.g. within reservoir R on the luminal side LS, to facilitate mucus production and accumulation. Mechanical stimulation can include, but is not limited to, shear stress applied on the apical surface by fluid flow, mechanical scrape of the apical mucus layer, and/or cyclic deformation of cells to mimic peristalsis, etc.

Any combination of the methods described herein can be used to facilitate the formation of a mucus layer above a cell monolayer comprising mucus producing cells. By adjusting the methods and combinations of methods as described herein mucus layers can be generated having different properties including different thicknesses, different densities and regions of different densities/thicknesses.

Accordingly, in some embodiments, the presently disclosed subject matter can provide methods of producing live cell constructs comprising a cell monolayer comprising mucus producing cells and a mucus layer, the method comprising: (a) culturing stem cells that are capable of differentiating into mucus producing cells (e.g., intestinal epithelial stem cells, basal stem cells, induced pluripotent stem cells and the like) on an upper surface of a cell support structure having both an upper surface and a lower surface until at least a portion of the upper surface of the cell support structure is covered by the stem cells; and (b) culturing the stem cells further to produce a cell monolayer comprising mucus producing cells (e.g., goblet cells), the cell monolayer having a basal side and a luminal (apical) side, wherein the mucus producing cells of the cell monolayer establish a mucus layer on the luminal side of the cell monolayer, and wherein the mucus layer is substantially impenetrable to micro-objects, thereby producing a live cell construct comprising a cell monolayer comprising mucus producing cells and a mucus layer. In some embodiments, the mucus layer can have a thickness of about 1 micron to about 1 cm.

In some embodiments, the presently disclosed subject matter can provides methods of producing live cell constructs comprising a cell monolayer comprising mucus producing cells and a mucus layer, the method comprising: (a) culturing stem cells that are capable of differentiating into mucus producing cells (e.g., intestinal epithelial stem cells, basal stem cells, induced pluripotent stem cells and the like) on an upper surface of a cell support structure having both an upper surface and a lower surface until at least a portion of the upper surface of the cell support structure is covered by the stem cells; and (b) culturing the stem cells further to produce a cell monolayer comprising mucus producing cells (e.g., goblet cells), the cell monolayer having a basal side and a luminal (apical) side, wherein the mucus producing cells of the cell monolayer establish a mucus layer on the luminal side of the cell monolayer, the mucus layer having a thickness of about 1 microns to 1 cm, thereby producing a live cell construct comprising a cell monolayer comprising mucus producing cells and a mucus layer. In some embodiments, the mucus layer can be impenetrable or substantially impenetrable to micro-objects.

In some embodiments, the presently disclosed subject matter can provide methods of producing live cell constructs comprising a cell monolayer comprising mucus producing cells and a mucus layer, the method comprising: (a) culturing stem cells that are capable of differentiating into mucus producing cells (e.g., intestinal epithelial stem cells, basal stem cells, induced pluripotent stem cells and the like) on an upper surface of a cell support structure having both an upper surface and a lower surface until at least a portion of the upper surface of the cell support structure is covered by the stem cells; and (b) culturing the stem cells further to produce a cell monolayer comprising mucus producing cells (e.g., goblet cells), the cell monolayer having a basal side and a luminal (apical) side, wherein the mucus producing cells of the cell monolayer establish a first mucus layer and a second mucus layer on the luminal side of the cell monolayer, wherein the first mucus layer is adjacent to and above the second mucus layer and the second mucus layer is adjacent to and above the cell monolayer and the second mucus layer is impenetrable or substantially impenetrable to micro-objects, thereby producing a live cell construct comprising a cell monolayer comprising mucus producing cells and a mucus layer. In some embodiments, the thickness of the second mucus layer can be about 1 micron to about 1 cm, as described further herein.

In some embodiments, a method of producing a live cell construct comprising a cell monolayer comprising mucus producing cells and a mucus layer is provided, the method comprising: (a) culturing stem cells that are capable of differentiating into mucus producing cells (e.g., intestinal epithelial stem cells, basal stem cells, induced pluripotent stem cells and the like) on an upper surface of a cell support structure having both an upper surface and a lower surface until at least a portion of the upper surface of the cell support structure is covered by the stem cells; and (b) culturing the stem cells further to produce a cell monolayer comprising mucus producing cells (e.g., goblet cells), the cell monolayer having a basal side and a luminal (apical) side, wherein the mucus producing cells of the cell monolayer establish a first mucus layer and a second mucus layer on the luminal side of the cell monolayer, wherein the first mucus layer is adjacent to and above the second mucus layer and the second mucus layer is adjacent to and above the cell monolayer and the second mucus layer comprises a thickness of about 1 microns to 1 cm, thereby producing a live cell construct comprising a cell monolayer comprising mucus producing cells and a mucus layer. In some embodiments, the second mucus layer can be impenetrable or substantially impenetrable to micro-objects.

In some embodiments, in the methods of the presently disclosed subject matter a basal reservoir can be defined below the basal side of the cell layer of mucus producing cells and a luminal reservoir can be defined above the luminal side of the cell monolayer comprising mucus producing cells, and the basal reservoir and the luminal reservoir can each comprise a liquid medium; the method further comprising: (a) removing the liquid medium in the luminal reservoir to produce an air-liquid interface at the luminal side of the cell layer that comprises mucus producing cells; and/or (b) adjusting the volume of the liquid medium in the luminal (apical) reservoir to a depth in a range of about 0.001 mm to about 10 mm, optionally about 0.001 mm to about 1 mm, above the luminal side of the cell monolayer. In some embodiments, the mucus layer is present or develops between the liquid medium and the cell monolayer. Thus, in some embodiments, the volume of liquid can be adjusted prior to, during, or after the production of mucus by the mucus producing cells. Once mucus producing cells are present in the live cell construct, at least a thin mucus film can be constitutively produced by the mucus producing cells (e.g., goblet cells). A thick layer of mucus can then accumulate after the adjustment of the volume of liquid in the luminal reservoir. In some embodiments, the mucus layer can be continuous or it can be discontinuous across the surface of the cell monolayer.

In some embodiments, stem cells useful with the present disclosure can include, but are not limited to, epithelial stem cells, intestinal epithelial stem cells, basal stem cells, induced pluripotent stem cells, respiratory stem cells, gastric stem cells, nasal stem cells, reproductive tract cells (cervix, vagina, uterus), urethra cells, olfactory cells, mouth cells, tongue cells, and/or conjunctiva cells. In some embodiments, the stem cells are intestinal epithelial stem cells.

In some embodiments, a live cell construct comprising a cell monolayer comprising mucus producing cells can comprise one or more different cell types (e.g., 1, 2, 3, 4, 5, or more) in addition to mucus producing cells (e.g., goblet cells). A "cell type" as used herein refers to morphologically or phenotypically distinct cell forms within a species. In some embodiments, the cells positioned on a cell support structure can be from healthy, inflamed, or diseased human or animal tissue. In some embodiments, cells useful for making a live cell construct of the presently disclosed subject matter can be from human or animal tissue having a disease comprising mucus misregulation, including but not limited to, inflammatory bowel disease, constipation, cystic fibrosis irritable bowel syndrome, leaky gut syndrome, bacterial overgrowth syndromes, celiac disease, lactose intolerance, excessive gas syndromes, diarrheal diseases, and/or polyps appendicitis.

In some embodiments, a cell layer of the presently disclosed subject matter can be flat, 2-dimensional as illustrated, for example, in FIGS. 1A through 1E. In some embodiments, a cell monolayer of the presently disclosed subject matter can also be folded in a 3-dimensional shape or structure to mimic, for example, the crypt structure or crypt-villus structure of in vivo intestines.

In some embodiments, the methods of the present presently disclosed subject matter can further comprise positioning an impermeable physical barrier and/or a partially permeable (i.e., semi-permeable) physical barrier on or over the luminal side of the cell monolayer comprising mucus producing cells (and on or over/above the mucus layer). In some embodiments, water transit can be regulated by controlling liquid/water movement or water vapor movement.

In some embodiments, the impermeable and/or partially permeable physical barrier can be positioned directly on the luminal side of the cell monolayer comprising mucus producing cells or directly on the mucus layer (if already present). That is, the impermeable and/or partially impermeable physical barrier can be positioned to be in direct contact with the mucus producing cells and/or the mucus layer. Alternatively, liquid medium can be present between the physical barrier and the mucus producing cells and/or the mucus layer when the physical barrier is positioned. In some embodiments, when present between the physical barrier and the mucus producing cells and/or mucus layer, the liquid medium can be present at a depth in a range of about 0.001 mm to about 10 mm, optionally about 0.001 mm to about 1 mm, above the luminal side of the cell monolayer (and/or above the luminal side of the mucus layer) and below the physical barrier.

In some embodiments, the volume of the liquid medium in the luminal (apical) reservoir (with or without a physical barrier), or on the luminal side of the cells, can be a depth in a range of about 0.001 mm to about 10 mm above the luminal side of the cell monolayer (e.g., about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 10 mm, or any value or range therein) (e.g., about 0.005 mm to about 10 mm, 0.01 mm to about 10 mm, about 0.05 mm to about 10 mm, 0.1 mm to about 10 mm, about 0.5 mm to about 10 mm, 1 mm to about 10 mm, about 5 mm to about 10 mm, about 0.001 mm to about 1 mm, about 0.005 to about 1 mm, 0.01 mm to about 1 mm, about 0.05 mm to about 1 mm, 0.1 mm to about 1 mm, about 0.5 mm to about 1 mm, about 0.001 mm to about 0.1 mm, about 0.005 to about 0.1 mm, 0.01 mm to about 0.1 mm, about 0.05 mm to about 0.1 mm, 0.1 mm to about 0.1 mm, about 0.5 mm to about 0.1 mm, or any value or range therein).

As used herein, a "partially permeable physical barrier" is impermeable or substantially impermeable to mucin, but water can pass through the barrier. Thus, in some embodiments, a partially permeable physical barrier can have a molecular weight cut-off (MWCO) of about 100 kDa, i.e., the barrier is impermeable to molecules greater than (>) about 100 kDa. In some embodiments, the partially permeable barrier can have a MWCO of about 100 to about 150 kDa). Mucin has molecular weight of about 200 kDa-200 MDa.

As used herein an "impermeable physical barrier" is at least substantially, and preferably completely, impermeable to the liquid medium (e.g., water) and to mucin.

Thus, in some embodiments, an impermeable physical barrier or a partially permeable physical barrier can be used to confine mucins on or near the surface of a mucin producing cell monolayer. In some embodiments, an impermeable physical barrier and/or a partially permeable physical barrier can be used to prevent or reduce the dilution by the liquid medium of the mucin as it is produced by the cell monolayer.

Non-limiting examples of physical barriers include a semi-liquid mass (e.g. hydrogels), a gas-impermeable membrane, a gas permeable membrane, and hygroscopic materials (honey, glycerin, sugar, nylon, ABS (acrylonitrile/butadiene/styrene), polycarbonate, cellulose, and poly (methyl methacrylate)). In some embodiments, partially permeable (e.g., molecular weight cutoff of about 100 kDa) physical barriers can include but are not limited to porous materials including porous membranes, some synthetic polymers, hydrogels (e.g., agarose, gelatin, collagen, Matrigel®, etc.), some oils, and/or meshes (e.g., nylon, photoresists, polydimethylsiloxane and other synthetic polymers, etc.). In some embodiments, a vapor permeable (mucus impermeable) physical barrier can be used. Nonlimiting examples of vapor permeable membranes useful with the presently disclosed subject matter include polydimethylsiloxane (PDMS) without coatings/fillers, some synthetic polymers, and/or meshes. Non-limiting examples of impermeable membranes (impermeable to water and to mucin) include solid floaters (e.g., waxes, plastics, etc.), meshes (nylon, photoresists, polydimethylsiloxane and other synthetic polymers, etc.), oils (e.g., mineral oils, perfluorocarbons, natural oils etc.), and/or synthetic polymers.

In some embodiments, the thickness of a mucus layer of a live cell construct of the presently disclosed subject matter can be about 1 micron to about 1 cm (10,000 microns) (e.g., about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 335, 940, 945, 950, 955, 960, 965, 970, 975, 980, 985, 990, 995, 1000, 1100, 1200, 1300, 1400, 1500, 1600, 1700, 1800, 1900, 2000, 2100, 2200, 2300, 2400, 2500, 3000, 3500, 4000, 4500, 5000, 5500, 6000, 6500, 7000, 7500, 8000, 8500, 9000, 9500, 10,000 microns, or any value or range therein). Thus, in some embodiments, the thickness of the mucus layer can be about 2 microns to about 1 cm, about 3 microns to about 1 cm, about 4 microns to about 1 cm, about 5 microns to about 1 cm, about 6 microns to about 1 cm, about 7 microns to about 1 cm, about 8 microns to about 1 cm, about 9 microns to about 1 cm, about 10 microns to about 1 cm, about 20 microns to about 1 cm, about 30 microns to about 1 cm, about 40 microns to about 1 cm, about 50 microns to about 1 cm, about 60 microns to about 1 cm, about 70 microns to about 1 cm, about 80 microns to about 1 cm, about 90 microns to about 1 cm, about 100 microns to about 1 cm, about 200 microns to about 1 cm, about 300 microns to about 1 cm, about 400 microns to about 1 cm, about 500 microns to about 1 cm, about 1000 microns to about 1 cm, about 1500 microns to about 1 cm, about 30 microns to about 7500 microns, about 40 microns to about 7500 microns, about 50 microns to about 7500 microns, about 60 microns to about 7500 microns, about 70 microns to about 7500 microns, about 80 microns to about 7500 microns, about 90 microns to about 7500 microns, about 100 microns to about 7500 microns, about 500 microns to about 7500 microns, about 1000 microns to about 7500 microns, about 30 microns to about 5000 microns, about 40 microns to about 5000 microns, about 50 microns to about 5000 microns, about 60 microns to about 5000 microns, about 70 microns to about 5000 microns, about 80 microns to about 5000 microns, about 90 microns to about 5000 microns, about 100 microns to about 5000 microns, about 500 microns to about 5000 microns, about 1000 microns to about 5000 microns, about 30 microns to about 2500 microns, about 40 microns to about 2500 microns, about 50 microns to about 2500 microns, about 60 microns to about 2500 microns, about 70 microns to about 2500 microns, about 80 microns to about 2500 microns, about 90 microns to about 2500 microns, about 100 microns to about 2500 microns, about 200 microns to about 2500 microns, about 300 microns to about 2500 microns, about 500 microns to about 2500 microns, about 10 microns to about 1000 microns, about 20 microns to about 1000 microns, about 30 microns to about 1000 microns, about 40 microns to about 1000 microns, about 50 microns to about 1000 microns, about 60 microns to about 1000 microns, about 70 microns to about 1000 microns, about 80 microns to about 1000 microns, about 90 microns to about 1000 microns, about 100 microns to about 1000 microns, about 200 microns to about 1000 microns, about 300 microns to about 1000 microns, about 500 microns to about 1000 microns, about 30 microns to about 500 microns, about 40 microns to about 500 microns, about 50 microns to about 500 microns, about 60 microns to about 500 microns, about 70 microns to about 500 microns, about 80 microns to about 500 microns, about 90 microns to about 500 microns, about 100 microns to about 500 microns, about 200 microns to about 500 microns, about 30 microns to about 400 microns, about 50 microns to about 400 microns, about 70 microns to about 400 microns, about 100 microns to about 400 microns, about 50 microns to about 350 microns, about 70 microns to about 350 microns, about 100 microns to about 350 microns, about 50 microns to about 300 microns, about 70 microns to about 300 microns, about 100 microns to about 300 microns, about 30 microns to about 250 microns, about 50 microns to about 250 microns, about 30 microns to about 200 microns, about 50 microns to about 200 microns, about 100 microns to about 200 microns, about 30 microns to about 150 microns, about 50 microns to about 150 microns, about 1 microns to about 100 microns, about 5 microns to about 100 microns, about 10 microns to about 100 microns, about 20 microns to about 100 microns about 30 microns to about 100 microns, about 50 microns to about 100 microns, or any range or value therein.

In some embodiments, a mucus layer produced by mucus producing cells of a live cell construct of the presently disclosed subject matter can be impenetrable or substantially impenetrable to (a population of) micro-objects (e.g., microorganisms or micro-particles (e.g., beads) in a size range from about 0.1 micron to about 100 microns (e.g., about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 microns (µm)) (e.g., about 0.1 to about 5 µm, about 0.1 to about 10 µm, about 0.1 to about 2 µm, about 0.1 to about 30 µm, about 0.1 to about 40 µm, about 0.1 to about 50 µm, about 0.1 to about 60 µm, about 0.1 to about 70 µm, about 0.5 to about 5 µm, about 0.5 to about 10 µm, about 0.5 to about 2 µm, about 0.5 to about 30 µm, about 0.5 to about 40 µm, about 0.5 to about 50 µm, about 0.5 to about 60 µm, about 0.5 to about 70 µm, about 0.5 to about 80 µm, about 0.5 to about 90 µm, about 0.5 to about 100 µm, about 1 to about 5 µm, about 1 to about 10 µm, about 1 to about 2 µm, about 1 to about 30 µm, about 1 to about 40 µm, about 1 to about 50 µm, about 1 to about 60 µm, about 1 to about 70 µm, about 1 to about 80 µm, about 1 to about 90 µm, about 1 to about 100 µm, about 2 to about 5 µm, about 2 to about 10 µm, about 2 to about 20 µm, about 2 to about 50 µm, about 2 to about 70 µm, about 2 to about 80 µm, about 2 to about 90 µm, about 2 to about 100 µm, about 5 to about 20 µm, about 5 to about 50 µm, about 5 to about 70 µm, about 5 to about 80 µm, about 5 to about 90 µm, about 5 to about 100 µm, about 10 to about 20 µm, about 10 to about 50 nm, about 10 to about 70 µm, about 10 to about 80 µm, about 10 to about 90 µm, about 10 to about 100 µm or any amount or range therein). A microorganism useful for measuring penetrability of mucus can be, for example, a bacterium. Non-limiting examples of bacteria that can be used to ascertain the permeability of a mucus layer as is known in the art and can include, for example, *Finnicutes, Bacteroidetes, Actinobacteria, Proteobacteria, Bacteroides, Clostridium, Faecalibacterium, Eubacterium, Ruminococcus, Peptococcus, Peptostreptococcus*, and *Bifidobacterium*. In some embodiments, the bacterium can be in the genus *Escherichia* spp. or *Lactobacillus* spp.). In addition, a micro-objective useful for determining penetrability/impenetrability of a mucus layer can be a micro-particle (e.g., bead) having a size of about 0.1 micron to about 100 microns. In general, micro-particles useful for measuring permeability are round and are comprised of one or more polymers (e.g., beads).

As used herein, "substantially impenetrable" means more than about 70% of a population of micro-objects are unable to penetrate the mucus layer (e.g., more than about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, and any range or value therein; e.g., about 70% to about 99%, about 75% to about 99%, about 80% to about 99%, about 85% to about 99%, about 90% to about 99%, about 95% to about 99%, and any range or value therein, of the population of micro-objects are unable to penetrate the mucus layer) and/or the micro-objects that penetrate can travel a distance of less than about 30% into the thickness of the mucus layer (or less than 30% of the distance from the luminal side of the mucus layer to the basal side of the mucus layer) (e.g., about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30%; e.g., about 0.5% to about 30%, about 1% to about 30%, about 5% to about 30%, about 10% to about 30%, about 15% to about 30%, about 20% to about 30%, about 0.5% to about 20%, about 1% to about 20%, about 5% to about 20%, about 10% to about 20%, about 15% to about 20%, about 20% to about 25%, about 0.5% to about 15%, about 1% to about 15%, about 5% to about 15%, about 10% to about 15%, about 0.5% to about 10%, about 1% to about 10%, about 5% to about 10%, about 0.5% to about 5%, about 1% to about 5%, about 2.5% to about 5%, about 0.5% to about 1%, and any range or value therein). In some embodiments, a mucus layer that is substantially impenetrable can be impenetrable to more than 90% (e.g., about 90, 91, 92, 93, 94, 95, 96, 97, 98, 99%, and any range or value therein; e.g., about 90% to about 99%) of a population of micro-objects. In some embodiments, in a mucus layer that is substantially impenetrable can be impenetrable to more than 90%, the micro-objects that penetrate travel less than 10% (e.g., less than 0.5, 0.6, 0.7, 0.8, 0.9, 1, 2, 3, 4, 5, 6, 7, 8, 9, 10%) of the distance from the luminal side of the mucus layer to the basal side of the mucus layer.

As used herein "impenetrable" means more than about 99% (e.g., about 99, 99.1, 99.2, 99.3, 99.4, 99.5, 99.6, 99.7, 99.8, 99.9, 100%, and any range or value therein; e.g., 99-100%) of a population of micro-objects are unable to penetrate the mucus layer and/or the micro-objects that penetrate travel a distance of less than about 10% into the thickness of the mucus layer (e.g., less than 10% of the distance from the luminal side of the mucus layer to the basal side of the mucus layer) (e.g., less than 0.5, 0.6, 0.7, 0.8, 0.9, 1, 2, 3, 4, 5, 6, 7, 8, 9, 10%).

As used herein, a "cell support structure" can be any structure upon which the one or more cells and/or tissue can be positioned and can be organic, inorganic, or a composite thereof including, for example, any porous or mesh membrane.

In some embodiments, a cell support structure can comprise an organic polymer such as collagen, typically in combination with other ingredients as discussed below. In some embodiments, the supports are porous. A support can be provided or mounted on a porous carrier (e.g., a porous membrane, a mesh, an inorganic grid, a hydrogel, or a combination thereof) to lend structural support thereto, as also discussed below. A support can be in any suitable shape or configuration, including flat, tubular, curved, spherical, ellipsoid, etc., including composites there (e.g., to emulate macroanatomical structures).

Thus, a cell support structure useful with the presently disclosed subject matter can include, but is not limited to, a membrane, ECM (extracellular matrix), hydrogel, natural or synthetic polymers, and/or a two- or three-dimensional scaffold and/or any combination thereof. In some embodiments, for example, the bottom wall of a luminal reservoir can be a cell support structure (e.g., a membrane). In some embodiments, a cell support structure can comprise microstructures (e.g., features having a size of less than about 1 mm (e.g., about 100, 200 or 300 microns deep, up to 800 or 1000 microns deep or more, and/or from about 10 or 50 microns wide, up to 100 or 200 microns wide or more; e.g., a microwell, a post, and/or a groove). In some embodiments, a cell support structure can be comprised of, for example, polytetrafluoroethylene (PTFE), polyethylene terephthalate (PET), polycarbonate (PC), polyvinylidiene fluoride (PVDF), polyethersulfone (PES), cellulose acetate, regenerated cellulose, cellulose nitride, nylon, carbon grid, graphene films, glass, Bioglass (e.g., 45S5 Bioglass), hydroxyapatite, calcium phosphate, silicon, silicon oxide, silicon nitride, titanium oxide, aluminum oxide, gold, nickel, and/or stainless steel, or any combination thereof.

In some embodiments, a material useful as a cell support structure of the presently disclosed subject matter that is not naturally porous, can be made porous by methods that include, but are not limited to, sintering, etching, leaching, lithography, laser micromachining, etc. For example, a porous mesh of silicon and gold can be fabricated by lithography/etching. In some embodiments, photoreactive polymers such as photoresist that are fabricated into a film with micro or nanopores or micro or nanomesh by photolithography can be used for a cell support structure. In some embodiments, elastomeric films such as polydimethylsiloxane (PDMS) or EcoFlex that are fabricated into porous film or micro/nanomesh by soft lithography or molding can also be used as cell support structure. In some embodiments, a cell support structure can also be a dehydrated or flexible yet strong matrix such as a collagen or fibrin film or a composite.

Cells and/or tissues can be placed on a cell support structure or scaffold with or without additional adhesion proteins or extracellular matrices. In some embodiments, a scaffold can comprise extracellular matrix (ECM) materials including, but not limited to, collagen, gelatin, laminin, elastin, fibronectin, vitronectin, heparin sulfate, chondroitin sulfate, keratin sulfate, hyaluronic acid, gelatinous protein mixture secreted by Engelbreth-Holm-Swarm mouse sarcoma cells (e.g. Matrigel®, Geltrex®, MaxGel™, etc.), and/or commercially available cell substrates (e.g., CELLstart™ CTS™) and any combination thereof (e.g., a collagen/Matrigel® mixture). In some embodiments, hydrogel from natural polymers, synthetic polymers and hybrid hydrogel can be used to build a scaffold in two dimensions or three dimensions. Examples of natural polymers and synthetic polymers include, but are not limited to, chitosan, agarose, alginate (e.g., AlgiMatrix®), fibrin, silk, polyvinyl alcohol, sodium polyacrylate, acrylate polymers, polyethylene glycol (PEG), synthetic peptides, poly N-isopropylacrylamide, and/or any combination thereof. In some embodiments, the surface of a scaffold can be engineered to promote cell adhesion with any one or a combination of ECM molecules, natural or synthetic polymers or synthetic peptides including, but not limited to, poly-1-lysine, RGD-peptide and other integrin recognizing peptide segments. In some embodiments, a cell support structure useful with this presently disclosed subject matter can be mixed with cellular materials (immune cells or other cell types, tissues, blood), or non-cellular materials (drugs, polymer beads, magnetic particles, etc.). In some embodiments, a cell support structure can comprise a two or three dimensional micropatterns or microstructures.

In some embodiments, the cells of the live cell construct can be cultured in liquid medium comprising, for example, an additive, a compound, and/or a solution that can contribute to water balance across the cell layer, thereby assisting in formation of the mucus layer. In some embodiments, the additive, compound, and/or solution can include, but is not limited to, a hormone, a chemical additive, a food additive, a bacterial metabolite, and/or a hypertonic salt solution. In some embodiments, the additive, compound, and/or solution can be present in/introduced into a luminal reservoir (luminal side of the cell monolayer) and/or into a basal reservoir (basal side of the cell monolayer). Thus, for example, a hormone that stimulates secretion of water and electrolytes to the intestinal lumen can be added to the basal side of the cell monolayer (basal reservoir) to assist in the balance of fluid movement across the cell monolayer. In contrast, food additives and bacterial metabolites can be added to the luminal side of the cell monolayer (luminal reservoir).

In some embodiments, a hormone useful with this presently disclosed subject matter can include, but is not limited to, a vasoactive intestinal peptide (VIP), 5-hydroxytryptamine (serotonin, 5-HT), substance P, bone morphogenetic protein (BMP), gastrin, cholecystokinin, secretin, ghrelin, motilin, gastric inhibitory polypeptide, leptin, glucagon-like peptides, somatostatin, and/or neurotensin.

Non-limiting examples of useful chemical additives include, but are not limited to, butyrate, dibenzazepine, gamma secretase inhibitor (DAPT, LY411575), forskolin, guaifenesin, carbachol, prostaglandins, phorbal ester (phorbol 12-myristate 13-acetate), histamine, and/or N-(1-oxobutyl)-cyclic 3', 5'-(hydrogen phosphate) 2'-butanoate-adenosine, monosodium salt (i.e., dibutyryl-cAMP, sodium salt) (CAS 16980-89-5).

Exemplary food additives include N-nitrosoanabasine, matairesimol and/or caffeine.

In some embodiments, a bacterial metabolite can include, but is not limited to, a short chain fatty acid.

In some embodiments, a salt in a hypertonic salt solution that is useful with the presently disclosed subject matter can include, but is not limited to, to sodium, chlorine, potassium, magnesium, phosphate, carbonate, and/or lithium. In some embodiments, the concentration of the salt in the hypertonic solution can be about 1 mM to about 1000 mM (e.g., about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 335, 940, 945, 950, 955, 960, 965, 970, 975, 980, 985, 990, 995, 1000 mM, and any value or range therein). Thus, in some embodiments, the concentration of the salt in the solution can be about 5 mM to about 50 mM, about 5 mM to about 100 mM, about 10 mM to about 100 mM, about 10 mM to about 250 mM, about 10 mM to about 500 mM, about 10 mM to about 1000 mM, about 50 mM to about 100 mM, about 50 mM to about 500 mM, about 50 mM to about 1000 mM, about 100 mM to about 250 mM, about 100 mM to about 500 mM, about 100 mM to about 1000 mM, about 200 mM to about 500 mM, about 200 mM to about 1000 mM, about 300 mM to about 500 mM, about 300 mM to about 800 mM, about 300 mM to about 1000 mM, about 400 mM to about 500 mM, about 400 mM to about 800 mM, about 400 mM to about 1000 mM, about 500 mM to about 750 mM, about 500 mM to about 1000 mM, about 600 mM to about 1000 mM, about 700 mM to about 1000 mM, about 800 mM to about 1000 mM, and any value or range therein.

Any substance useful for the growth/maintenance of a cell and/or tissue can be introduced into a basal reservoir or luminal reservoir. In some embodiments, a substance can include, but is not limited to, fibronectin; laminin; epidermal growth factor (EGF); R-spondin; noggin; cytokines (e.g., interleukin (e.g., IL-6, IL-17, IL-22), tumor necrosis factor (TNF)); ephrin receptors (e.g., EphrinB, EphBs); bone morphogenetic proteins (BM's, BMP-2, BMP-7); Wnt (wingless-related integration site) (e.g., Wnt3, Wnt3A, and other Wnts); notch signaling factors (notch receptors); Dll1/4; Noggin; Grem1; Grem2; acetate; butyrate; proprionate, desaminotyrosine, catecholamine (e.g., dopamine, norepinephrine) cytokines, and/or short chain fatty acids.

In some embodiments, to assist in establishing a mucus layer, a force can be applied, e.g., parallel to the surface of the cell layer. In some embodiments, the force can be, for example, application of a surface tension force (e.g., air liquid interface (ALI) or it can be by application of a mechanical force. Non-limiting examples of application of a mechanical force include movement generated by a stir bar, moving a semi-solid material (e.g., hydrogel) parallel to the cell surface, and/or circulating a slurry on the top of the cell surface.

The presently disclosed subject matter further provides a live cell construct comprising a cell monolayer comprising mucus producing cells and a mucus layer, wherein the mucus layer is impenetrable or substantially impenetrable to micro-objects (e.g., microorganisms (e.g., bacteria) or micro-particles (e.g., beads)). In some embodiments, the mucus layer can be impenetrable or substantially impenetrable to micro-objects in a size range from about 0.1 to about 100 microns. In some embodiments, the mucus layer can be about 1 micron to about 1 cm in thickness (depth). In some embodiments, the mucus layer of a live cell construct of the presently disclosed subject matter can comprise a basal side and a luminal side, wherein the basal side is below the mucus layer and adjacent to (directly above) the mucus producing cells and the luminal side is above the mucus and the mucus producing cells and adjacent to (directly below) liquid medium or the air in the luminal reservoir.

The presently disclosed subject matter further provides methods of using the live cell construct of the presently disclosed subject matter, including but not limited to, studying (a) the ability of an organism, a drug, or a particle to traverse (penetrate) a mucus layer of a cell; (b) an immunological response of a cell comprising a mucus layer to invasion by an organism or contact with a particle and or chemical/compound; (c) the ability of an organism to infect a cell comprising a mucus layer; (d) the effectiveness of a drug to prevent infection by an organism or reduce the ability of an organism to infect; (e) misregulation of mucus in diseases including, but not limited to, inflammatory bowel disease, constipation, cystic fibrosis, irritable bowel syndrome, leaky gut syndrome, bacterial overgrowth syndromes, celiac disease, lactose intolerance, excessive gas syndromes, diarrheal diseases, and/or polyps appendicitis.

Thus, in some embodiments, the presently disclosed subject matter provides a method of determining the ability of an organism, a drug, or a particle to traverse (penetrate) a mucus layer of a cell monolayer, comprising: contacting the luminal side of the mucus layer of the live cell construct of the presently disclosed subject matter with the organism, drug, or particle; and measuring the distance that the organism, drug, or particle moves into/across the mucus layer (e.g., from the luminal side of the mucus layer to the basal side of the mucus layer), thereby determining the ability of the organism, drug or particle to traverse (penetrate) the mucus layer of the cell monolayer of the live cell construct. In some embodiments, the distance that the organism, the drug or the particle moves into the mucus layer can be measured over time, thereby determining the rate of movement of the organism, drug or particle into/across the mucus layer of the cell monolayer of the live cell construct.

In some embodiments, a method of studying and evaluating the ability of an organism to infect a cell monolayer comprising a mucus layer is provided, the method, comprising: contacting the luminal side of the mucus layer of the live cell construct of the presently disclosed subject matter with the organism; and determining if the organism traverses the mucus layer and contacts the cell monolayer of the live cell construct, wherein when the organism is determined to traverse the mucus layer and contact the cell monolayer, the organism is determined to be able to infect the cell monolayer comprising a mucus layer.

In some embodiments, a method of evaluating the effectiveness of a drug to prevent infection by an organism or to reduce the ability of an organism to infect is provided, comprising: contacting the luminal side of the mucus layer of the live cell construct of the presently disclosed subject matter with the organism; contacting the luminal side of the mucus layer of the live cell construct with the drug, and determining whether the organism penetrates the mucus layer and/or infects one or more cells of the cell monolayer of the live cell construct, wherein the drug is determined to be effective in preventing infection or reducing the ability of an organism to infect if the organism does not penetrate the mucus layer and/or does not infect one or more cells of the cell monolayer of the live cell construct as compared to a control (i.e., contacted with the organism but no drug). In some embodiments, wherein contacting the luminal side of the mucus layer of the live cell construct with the organism is prior to, concurrent with, or after contacting the luminal side of the mucus layer of the live cell construct with the drug. In some embodiments, a drug can be determined to be effective when about 25% to about 100% of the organisms are prevented from penetrating the mucus layer and/or are killed (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% are prevented from penetrating the mucus layer and/or are killed, and any range or value therein.

In some embodiments, the presently disclosed subject matter provides a method of evaluating an immunological response of a cell monolayer comprising a mucus layer to invasion by an organism, contact by a particle, and or contact by a chemical/compound, comprising: contacting the luminal side of the mucus layer of the live cell construct of the presently disclosed subject matter with the organism, particle and or chemical/compound; and assaying cells of the cell monolayer of the live cell construct for the production of a marker associated with an immune response (e.g., a cytokine, a chemokine, a hormone, a neurotransmitter, and/or a antimicrobial peptide), thereby evaluating the immunological response of the cell monolayer of the live cell construct to contact by the organism, particle and or chemical/compound.

In some embodiments, a chemical and/or compound can include, but is not limited to, a dietary metabolite and/or a bacteria metabolite such as vitamins or short chain fatty acids.

An organism that can be studied using the methods and live cell constructs of the present presently disclosed subject matter can be any organism and includes, for example, a bacterium, a virus, a fungus, protozoan, and/or a helminth. Thus, for example, any bacterium, virus, fungus, protozoan, or helminth can be studied for its ability to penetrate a cell's mucus layer, to evaluate the effectiveness of a drug to prevent infection by the organism/reduce the ability of an organism to infect, and/or to evaluate an immunological response of the cells of the live cell construct in response to contact by the organism.

In some embodiments, the organism can be a bacterium. Non-limiting examples of bacteria include those from the genus *Escherichia* spp., *Yersinia* spp., *Salmonella* spp., *Campylobacter* spp., *Clostridium* spp., *Helicobacter* spp., *Bacteroides* spp., *Peptostreptococcus* spp., *Vibrio* spp., *Shigella* spp., *Salmonella* spp., *Listeria* spp. and *Staphylococcus* spp. In some embodiments, a bacterium can include, but is not limited to, *Acinetobacter baumannii*, *Actinomyces israelii*, *Bacillus anthracia*, *Bacteroides fragilis*, *Bartonella henselae*, *Bordetella pertussis*, *Borrelia burgdorferi*, *Borrelia garinii*, *Borrelia afzelil*, *Borrelia recurrentis*, *Brucella*

*abortus, Brucella canis, Brucella melitensis, Brucella suis, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium amycolatum, Corynebacterium diphtheriae, Coxiella burnetii, Ehrlichia canis, Ehrlichia chaffeensis, Enterococcus faecalis, Enterococcus faecium, Escherichia coli,* Enterotoxigenic *Escherichia coli,* Enteropathogenic *Escherichia coli,* Enteroinvasive *Escherichia coli,* enterohemorrhagic *Escherichia coli, Francisella tularensis, Haemophilus influenzae, Helicobacter pylori, Klebsiella pneumoniae, Legionella pneumophila, Leptospira species, Listeria monocytogenes, Mycobacterium leprae, Mycobacterium tuberculosis, Mycoplasma pneumoniae, Neisseria gonorrhoeae, Neisseria meningitidus, Parachlamydia, Pseudomonas aeruginosa, Nocardia asteroides, Rickettsia rickettsii, Salmonella bongori, Salmonella enterica, Staphylococcus aureus, Staphylococcus epidermidis, Staphylococcus saprophyticus, Streptococcus agalactiae, Streptococcus pneumoniae Streptococcus pyogenes, Streptococcus viridans, Treponema pallidum, Vibrio cholerae, Vibrio vulnificus, Vibrio parahaemolyticus,* and/or *Yersinia pestis.*

In some embodiments, the organism can be a protozoan. Non-limiting examples of protozoa include those from the phylum of Amoebozoa, Excavata, and/or Chromalveolata. In some embodiments, a protozoan can include, but is not limited to, those from the genus Amoeba spp., *Entamoeba* spp., *Plasmodium* spp., *Giardia* spp., and/or *Trypanosoma* spp. In some embodiments, a protozoan can include, but is not limited to, *Entamoeba histolytica, Cryptosporidium parvum, Cryptosporidium hominis, Cyclospora cayetanensis,* and/or *Giardia lamblia*

In some embodiments, the organism can be a virus. Non-limiting examples of viruses include Simplexvirus, Varicellovirus, Cytomegalovirus, Roseolovirus, Lymphocryptovirus, Rhadinovirus, Adenovirus, Astrovirus, Calicivirus, Mastadenovirus, Alphapapillomavirus, Betapapillomavirus, Gammapapillomavirus, Mupapillomavirus, Nupapillomavirus, Polyomavirus, Molluscipoxvirus, Orthopoxvirus, Parapoxvirus, Alphatorquevirus, Betatorquevirus, Gammatorquevirus, Gemycircularviruses, Erythrovirus, Dependovirus, Bocavirus, Coltivirus, Rotavirus, Seadornavirus, Hepevirus, Alphacoronavirus, Betacoronavirus, Torovirus, Mamastrovirus, Norovirus, Sapovirus, Flavivirus, Hepacivirus, Pegivirus, Cardiovirus, Cosavirus, Enterovirus, Hepatovirus (e.g., hepatitis A), Kobuvirus, Parechovirus, Rosavirus, Salivirus, Alphavirus, Rubivirus, Deltavirus, Lyssavirus, Vesiculovirus, Filoviridae, Ebolavirus, Marburgvirus, Paramyxoviridae, Henipavirus, Morbilivirus, Respirovirus, Rubulavirus, Metapneumovirus, Pneumovirus, Arenavirus, Peribunyaviridae, Orthobunyavirus, Hantavirus, Nairovirus, Phenuiviridae, Phlebovirus, Influenzavirus A Influenzavirus B, Influenzavirus C, Thogotovirus, Gammaretrovirus Deltaretrovirus, Lentivirus, Spumavirus, and/or Orthohepadnavirus, In some embodiments, the organism can be a helminth including, but not limited to, intestinal flukes, round worms, pin worms, and/or tape worms. In some embodiments, the helminth can include, but is not limited to, a helminth from the genus of *Ascaris* spp., *Ancylostoma* spp., *Trichuris* spp, *Strongyloides* spp., *Necator* spp., *Schistosoma* spp., and/or *Trichinella* spp. Further non-limiting examples of helminths include *Ascaris lumbricoides* (roundworm), *Ancylostoma duodenale* (hookworm), *Necator americanus* (hookworm), *Strongyloides stercoralis, Trichinella spiralis* and/or *Trichuris trichiura* (whipworm).

In some embodiments, the organism can be a fungus. Non-limiting examples of fungi include those from the genus *Candida* spp., *Aspergillus* spp., *Mucor* spp., *Fusarium* spp., *Blastomyces* spp., *Coccidioides* spp., *Cryptococcus* spp., *Histoplasma* spp., *Rhizopus* spp., *Lichtheimia* spp., *Pneumocystis* spp., *Sporothrix* spp. and/or *Cunninghamella* spp. Further non-limiting examples of fungi include *Candida albicans, Candida tropicalis, Aspergillus flavus, Aspergillus fumigatus, Aspergillus niger, Cryptococcus neoformans, Cryptococcus gattii, Pneumocystis jirovecii,* and/or *Torulopsis, glabrata.*

The presently disclosed subject matter further provides a method of evaluating mucus misregulation in an in vitro cell system. In some embodiments, the method of evaluating mucus misregulation in an in vitro cell system comprises generating a live cell construct of the presently disclosed subject matter from stem cells from subjects having diseases associated with mucus misregulation. In some embodiments, a live cell construct of the present presently disclosed subject matter can be generated from stem cells from a healthy subject that are modified to recapitulate cells from diseases associated with mucus misregulation via genome editing (e.g. CRISPR-Cas9, TALEN, meganuclease). The mucus layers from the in vitro cell systems so generated can then be studied for characteristics including, but not limited to, thickness, composition, viscosity, degree of penetration by micro-objects, ability of microorganisms to infect, and/or responsiveness to drugs as described herein. Diseases associated with mucus misregulation include, but are not limited to, inflammatory bowel disease, constipation, cystic fibrosis irritable bowel syndrome, leaky gut syndrome, bacterial overgrowth syndromes, celiac disease, lactose intolerance, excessive gas syndromes, diarrheal diseases, and/or polyps appendicitis.

The presently disclosed subject matter will now be described with reference to the following examples. It should be appreciated that these examples are not intended to limit the scope of the claims to the presently disclosed subject matter, but are rather intended to be exemplary of certain embodiments. Any variations in the exemplified methods that occur to the skilled artisan are intended to fall within the scope of the presently disclosed subject matter.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods for Examples 1-4

In Vitro Expansion of Human Colonic Epithelial Stem Cells on a Collagen Hydrogel.

To expand human-derived intestinal epithelial stem cells, a monolayer culture technique was used according to a previously published protocol.[27, 30] Briefly, colonic crypts were isolated from transverse colon tissue specimens of a cadaveric donor (male, 23 years old), and plated directly on collagen hydrogel at a density of 1,000 crypts/well of a standard 6-well culture plate (possessing a 1 mm-thick collagen hydrogel) and overlaid with 4 mL stem medium (SM-Table 1). The medium was changed every 48 hours.

When the cell confluency reached 80% (typically 5-7 days), the monolayers were passaged and sub-cultured on fresh collagen hydrogel at a passage ratio of 1:3.[27, 30] The cells were karyotyped at P11 and 10 out of 10 spreads displayed normal karyotype. All experiments herein used cells at passage numbers less than P15.

Generation of a Mucus Layer on a Monolayer of Human Colonic Epithelium.

Transwell inserts possessing a porous membrane (0.4 μm pore size, Corning, #3460) were coated with 1 vol % Matrigel in phosphate-buffered saline (PBS) at 37° C. overnight. The inserts were rinsed with PBS×1 prior to cell plating. Intestinal epithelial cells were passaged according to the procedure described above except that the cells were suspended in expansion medium (EM-Table 1) and plated directly onto the top compartment of Transwell inserts. Cells from 1 well of the 6-well plate were dispersed into 6 separate 12-well Transwell inserts (1 mL in the upper [apical] reservoir, and 2 mL in the lower [basal] reservoir). The medium was exchanged every 48 h. To induce cell differentiation and mucus production, the medium was switched to differentiation medium (DM-Table 1) after 5 days. In the submerged culture, 1 mL DM was added in the apical reservoir and 2 mL in the basal reservoir. The medium was exchanged every 48 h thereafter. In the ALI culture, the medium in the apical reservoir was completely aspirated, 1 mL DM or DM-VIP (DM containing 330 ng/mL VIP [AnaSpec, #AS-22872]) was added to the basal reservoir, and medium was exchanged every 24 h thereafter. By day 10, the system was suitable for characterization and cytokine assay.

stained with anti-Muc2 antibody (Santa Cruz, #sc-15334) to reveal the mucus layer (Muc2 is the major structural component in colonic mucus layer), and DNA in the nuclei of the cells was stained with Hoechst 33342 (ThermoFisher, #62249).[30] To reveal the mucus layer and apical features of the cells, the tissues were fixed by either Carnoy's solution (for submerge and ALI culture) or glyoxal (for ALI culture with DM-VIP) at 4° C. for 2 h, dehydrated in a graded ethanol (25%, 50%, 75% and 100%), dried with a critical point dryer (Tousimis Semidri PVT-3), coated with 10-nm metal by a sputter coater (Cressington 108), and inspected by SEM (FEI Quanta 200 ESEM, FEI Company).

To demonstrate the bacterial separating capability of mucus layer, the live epithelial cells were first stained with Hoechst 33342 by adding 1 mL medium containing 2 μg/mL of Hoechst 33342 to the basal reservoir for 1 h, and then 0.5 mL of a suspension of GFP EC (ATCC, #25922GFP) at a density of 200 million colony-forming units (cfu)/mL, or 1 μm red fluorescent beads (ThermoFisher, #F13083) at a density of $10^8$ beads/mL was added to the apical reservoir. After seeding for 20 min, the Transwell insert was placed on a cover glass and the tissue was imaged with an Olympus FluoView FV3000 confocal laser scanning microscope.

Toxin A Experiment.

20 μL of a mixture of natural *C. difficile* toxin A protein (Abcam, #ab123999) at 0 or 12 μg/mL and FITC-dextran (Sigma, #FD40S) at 5 mg/mL was added to the apical side of the human colonic epithelial monolayers (±mucus) which spread to form a 180 μm liquid layer. 1 mL Hanks' balanced salt solution (with calcium/magnesium, supplemented 10%

TABLE 1

Formulation of culture media for human colonic epithelial cells

| | SM | EM | DM | DM-VIP |
|---|---|---|---|---|
| WRN-conditioned medium | 50 vol % | 50 vol % | | |
| Advanced DMEM/F12 | 50 vol % | 50 vol % | 100 vol % | 100 vol % |
| GlutaMax | 1× | 1× | 1× | 1× |
| HEPES | 10 mM | 10 mM | 10 mM | 10 mM |
| Murine EGF | 50 ng/mL | 50 ng/mL | 50 ng/mL | 50 ng/mL |
| N-acetyl cysteine | 1.25 mM | 1.25 mM | 1.25 mM | 1.25 mM |
| Primocin | 50 μg/mL | 50 μg/mL | 50 μg/mL | 50 μg/mL |
| B27 | 1× | 1× | | |
| Gastrin | 10 nM | 10 nM | | |
| A83-01 | 500 nM | | 500 nM | 500 nM |
| SB202190 | 3 μM | 3 μM | | |
| Y-27632 | 10 μM* | 10 μM* | | |
| Nicotinamide | | 10 mM | | |
| PGE2 | | 10 nM | | |
| VIP | | | | 330 ng/mL |

*Used in the first 48 hours after cell plating to prevent dissociation-induced cell apoptosis.

Abbreviations:
  WRN: Wnt-3A, R-spondin 3, Noggin
  DMEM/F12: 1:1 mixture of Dulbecco's Modified Essential Medium (DMEM) and Ham's F-12 Medium
  HEPES: 4-(2-hydroxyethyl)-1-piperazineethanesulfonic acid
  EGF: epidermal growth factor
  PGE2: prostaglandin E2
  VIP: vasoactive intestinal peptide Characterization of Human Colonic Epithelium and Mucus Layer.

The cells and mucus layer were fixed with Carnoy's solution (ethanol 6:acetic acid 3:chloroform 1, v/v/v) at 4° C. for 2 h. The tissues were dehydrated with ethanol, and embedded in paraffin for sectioning. The sections were fetal bovine serum and 10 mM HEPES) was added to the basal compartment. 150 μL samples were collected from the basal compartment at 2, 4, 8 and 24 h. The fluorescence intensity of the collected samples was measured in a microplate reader and the percent permeability was calculated as: % permeability=100×(sample-blank)/(transwell-blank), where "transwell" indicates the liquid collected from inserts without cells. The cells were fixed by ethanol and stained with phalloidin (ThermoFisher, #R37110) and ZO-1 antibody (ProtenTech, #21773-1-AP) to reveal the F-actin and tight junctions.

Co-Culture with *E. coli* and PBMCs.

Fresh normal human PBMCs were purchased from Physician's Plasma Alliance (Johnson City, TN). PBMCs were suspended in RPMI medium containing 10% fetal bovine serum (FBS) and 100 mg/ml gentamicin at 2.86 million cells/mL. GFP EC was cultured in a nutrient broth with 100 μg/mL ampicillin. A suspension of GFP EC at a density of 200 million cfu/mL was prepared in 10 mL phosphate-buffered saline (PBS), centrifuged at 2300 g and washed twice with PBS. GFP EC were re-suspended in 0.2 mL RPMI medium containing 10% FBS. Gentamicin (100 mg/ml) was added to the medium to avoid uncontrolled bacterial growth.[54] For the colonic monolayers under submerged culture in DM for 5 days, the medium was aspirated from both top and bottom reservoirs. For those under ALI culture in DM-VIP for 5 days, the medium was aspirated from the bottom reservoir only. 20 μL GFP EC suspension (20 million cfu) was added to the apical side of the epithelium. 500 μL PBMCs suspension (1.43 million) was added to the basal reservoir. After 24 h of co-culture, the media from the basal reservoirs were collected, centrifuged at 5000 rpm for 6 min, aliquoted and stored at −20° C.

Quantification of Cytokines.

The concentrations of cytokines (IL-8, IL-6, IL-1β and TNF-α) were determined using ELISA kits (ThermoFisher) according to the manufacturer's instructions. The samples were diluted 40× (for IL-8), 10× (for IL-6) or 5× (for IL-1β and TNF-α) so that the measurements fell within the linear range for a given kit. Three samples were used for each condition. The change of cytokine concentration compared to untreated control was analyzed statistically by two-tailed unpaired t-test. In all figures, '**' denotes p<0.005, '*' p<0.05, and '#' not statistically significant.

Example 1

Figure 2B:
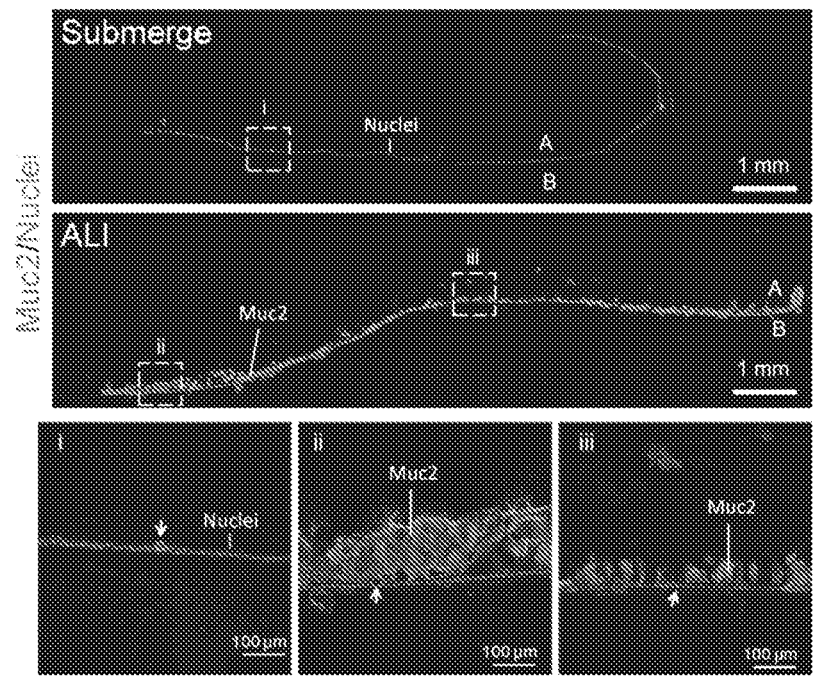
Figure 2C:
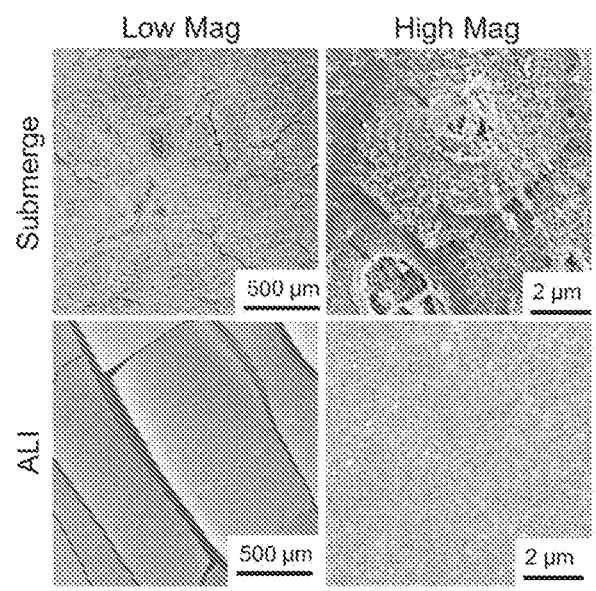

An Air-Liquid Interface (ALI) Culture Enables a Compact Mucus Layer to Accumulate on the Apical Colonic Epithelium Initially, an air-liquid interface (ALI) culture was tested to aid in generation of a mucus layer as it was hypothesized that the overlying media under standard submerged culture might be diluting the mucus as it was secreted preventing a dense mucus layer from forming. Human epithelial stem cells obtained from the transverse colon were plated on a Matrigel-coated Transwell (porous membrane) and cultured under expansion medium (EM) for 5 days to enable cells to proliferate and form a confluent monolayer. At day 5, the medium was switched to differentiation medium (DM), and the cells were cultured for an additional 5 days as either a submerged culture (medium in both apical and basal reservoirs) or as an ALI culture (medium in basal reservoir only) (FIG. 2A). Due to the absence of growth factors in DM, the cells lost their proliferative capacity and spontaneously differentiated to mature cell lineages composed of a mixture of colonocytes, goblet cells and enteroendocrine cells.[29] At day 10 of culture, the mucus layer was absent in the submerged culture (FIG. 2B). As shown in FIG. 2C, when viewed by scanning electron microscopy (SEM), no mucus layer was visible over these monolayers and the epithelium and its apical features (secretory granules of goblet cells, arrows) were readily apparent (FIG. 1C, top panel). As described previously, dissolved mucins were detectable in the luminal medium by enzyme-linked immunosorbent assay (ELISA),[30] thus it was possible that the mucins secreted by the goblet cells were rapidly diluted in the medium and thus unable to build a dense, physiologic hydrogel.

In the ALI culture, a continuous mucus layer (Muc2⁺) was observed by immunofluorescence along the entire apical surface of the epithelium (FIG. 2B). The thickness of this mucus layer was heterogeneous and ranged from 76 to 154 μm. The mucus was sometimes associated with goblet cells (indicated with arrows in FIG. 2B). When viewed by SEM, the mucus demonstrated continuous coverage of the epithelium (FIG. 2C, bottom panel) with interspersed fractures due to the dehydration process required for SEM imaging. Cells could not be visualized under the dense mucus layer (high magnification image in the right panel). In addition to the potential for dilution, a variety of mechanisms which impact mucus production can be operational to enhance mucus secretion as seen here. ALI culture has been shown to increase mucus production in the respiratory system and some tissue-cultured tumor cell lines derived from the stomach and intestine,[31-37] although this effect has not been demonstrated previously using primary intestinal tissue. Mechanical forces in combination with ALI have been shown to enhance mucus production by a bed of tumor cells, so surface tension forces exerted by a thin fluid layer can be a contributing factor.[37] Evaporation can also provide an additional stimulus due to an increase in the osmolality of the thin residual water film, since hyperosmolar solutions have been shown to cause mucus hypersecretion in human bronchial epithelial cells.[38, 39] Lastly, changes in osmolality are also known to stimulate production of trefoil factor 3 by colonic epithelial cells, which acts to improve mucus quality and density.[8, 40]

Figure 2D:
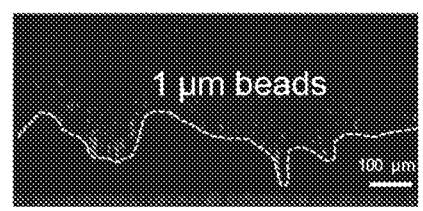
Figure 2E:
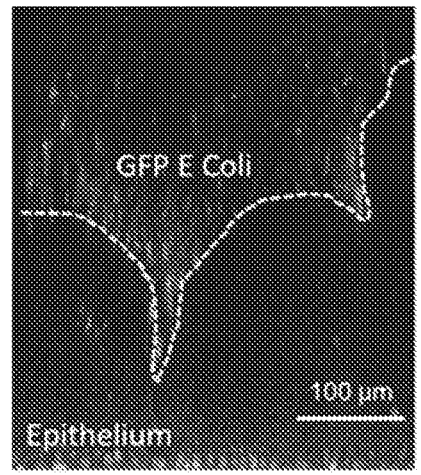

To determine whether the compact mucus layer served as a barrier to effectively separate microbeads or bacteria from the epithelium, a suspension of 1 μm red fluorescent beads (FIG. 2D) or green fluorescent protein (GFP)-expressing *E. coli* (GFP EC) (FIG. 2E) was added to the luminal reservoir after ALI culture of an epithelium stained with Hoechst 33342. The thickness of the mucus layer was then evaluated by confocal microscopy (FIGS. 2D and 2E). The distance of the beads and bacteria from the epithelial cells ranged from 71 to 381 μm in the representative images shown in FIGS. 2D and 2E, with an average of 138±62 μm (N=3 locations). While this mucus layer effectively acted as a barrier to separate microbeads or bacteria, it formed mucus clumps with a heterogeneous thickness.

Example 2

A Hydrated, Thick Mucus Layer can be Created by Promoting Luminal Water Secretion in a Modified ALI Culture Gas originating from bacterial metabolism is present within the lumen of the large intestine; however, the luminal surface in vivo is predominantly in contact with indigestible materials and waste products possessing a high water content. Thus, in some embodiments the ALI culture described above does not fully reflect the in vivo intestinal luminal environment due to the absence of water at the apical surface. Indeed, water and electrolyte homeostasis of the colonic mucosa are balanced with water moving into and out of the lumen. For healthy adults, the rate of movement of water out of the lumen is 17.8 mL/min and that into the lumen is 16 mL/min, resulting in a net water efflux of 1.85 mL/min causing solidification of the feces.[41] Intestinal hormones, such as 5-hydroxytryptamine (serotonin; 5-HT), vasoactive intestinal peptide (VIP) and substance P play major roles in regulating the fluid balance or water content of the luminal content of the large intestine.[42] To develop a strategy to produce a thick, highly hydrated, uninterrupted mucus layer of uniform thickness, exposure of the basal epithelial surface to the hormone VIP, using VIP containing DM (DM-VIP), was used to assist in the balance of fluid movement across the epithelium (FIG. 3A). VIP is an endogenous hormone with a plasma concentration in healthy adults ranging from 14 to 76 pg/mL.[43] Its role in the intestine is to stimulate secretion of water and electrolytes into the intestinal lumen.[44] VIP also can act to increase mucus secretion and production by goblet cells as well as enhance lineage allocation towards goblet cells.[45]

Figure 3B:
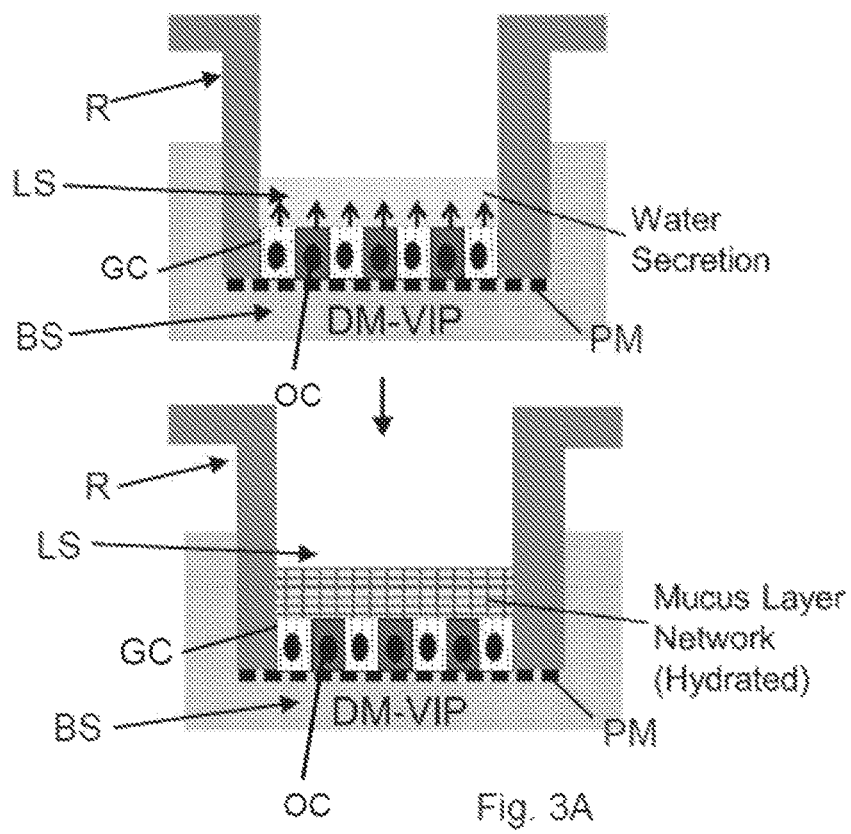
Figure 3B:
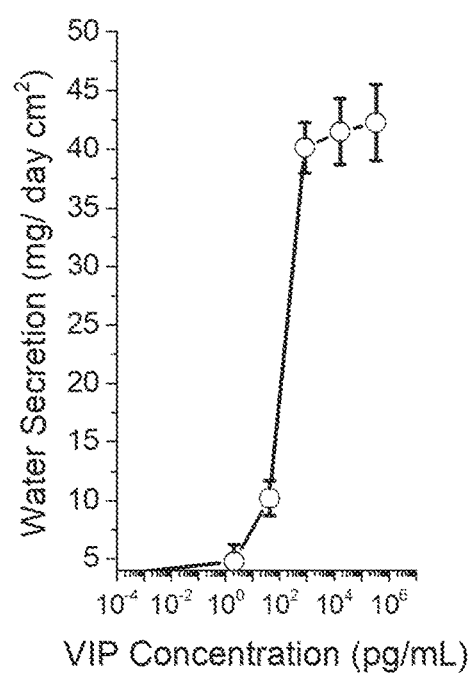

To verify the function of VIP to stimulate water secretion, human colonic stem cells were cultured under EM for 5 days. At day 5, the basal medium was switched to DM with varying VIP concentration and the cells placed under the ALI culture conditions. After 24 h, the water accumulated in the apical reservoir was collected and weighed with an analytical balance. In the absence of VIP, the accumulation of water in the apical reservoir was not measurable. In the presence of VIP, the secretion of water was VIP concentration dependent with an effective dose 50 ($ED_{50}$) of 210 pg/mL (FIG. 3B). A plateau was reached when VIP concentration was >1 ng/mL. At this saturating concentration, approximately 42 mg/cm$^2$ water accumulated after a 24 h incubation with VIP, corresponding to a water depth in the reservoir of 420 μm.

Figure 3C:
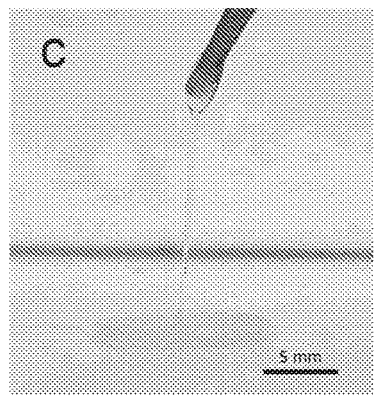
Figure 3D:
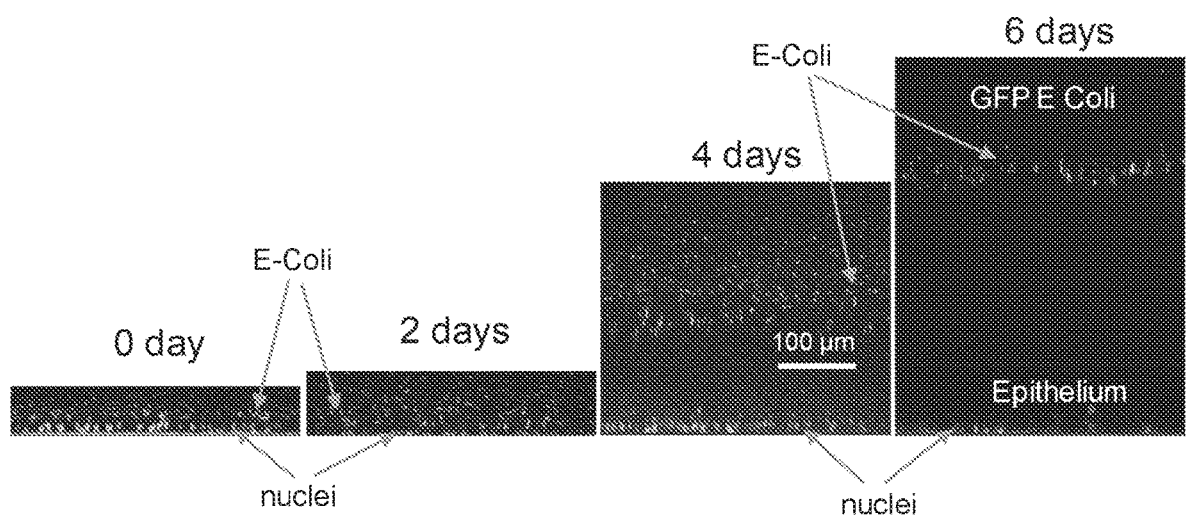
Figure 3E:
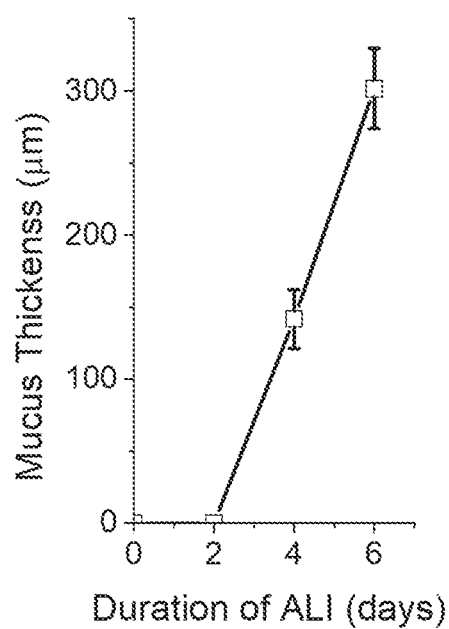
Figure 3F:
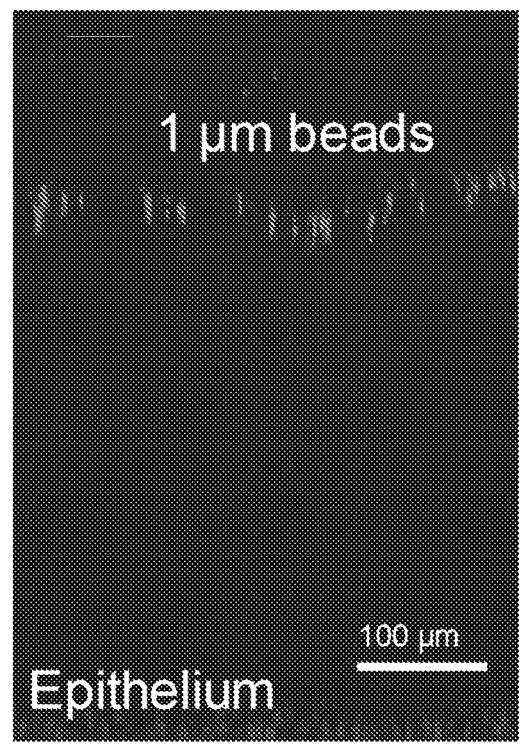
Figure 3G:
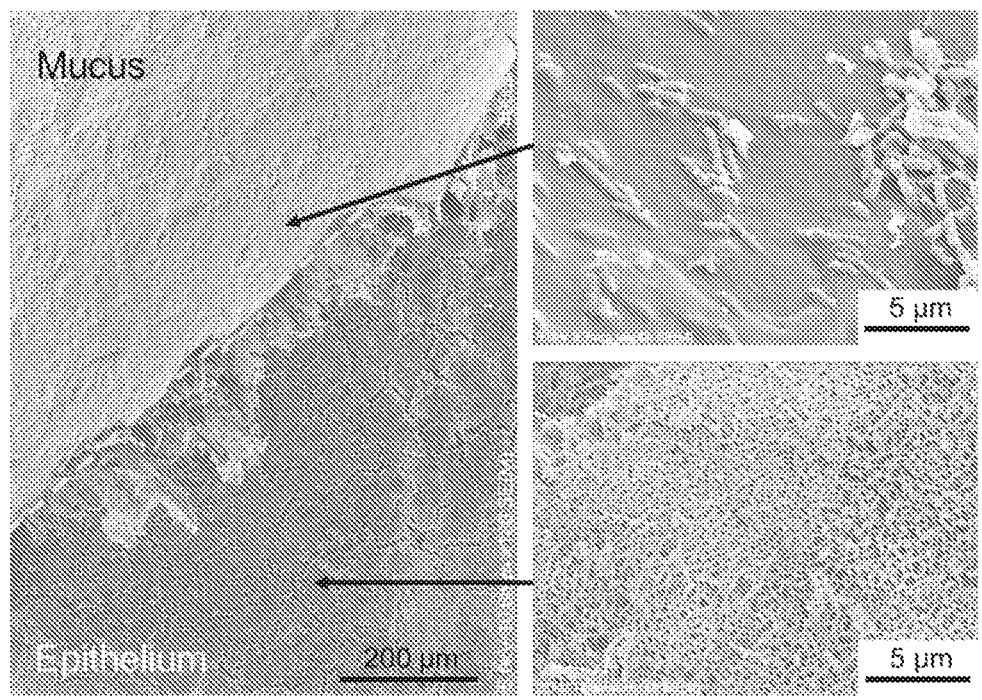

Under ALI culture with DM-VIP (DM containing a saturating concentration of VIP), a layer of liquid accumulated on the apical side within 24 h, and this liquid layer was maintained during the 5-6 days of differentiation culture conditions. The apical liquid layer became more and more viscous, and at 5 days a slippery mucus hydrogel was generated which could be lifted off the epithelium by forceps for visualization (FIG. 3C). Under these conditions, the mucus thickness was dependent on the duration of mucus accumulation (i.e., time under ALI plus DM-VIP). To demonstrate the accumulation of the mucus layer over time, human colonic epithelial cells were maintained in a submerged culture in EM for 5 days, followed by culture in DM-VIP for 6 days under the ALI conditions described above. Confocal imaging was performed at 0, 2, 4 and 6 days. Cell nuclei in the monolayer were stained with Hoechst 33342. A suspension of GFP-EC was overlaid onto the mucus layer as described and the distance between the bacteria and epithelial cells measured as described for the micro-beads. The distance between the E. coli (labelled with arrows) and the nuclei (labelled with arrows) show the mucus layer component effectively separated the bacteria from the epithelium (FIG. 3D) over time. At 0 and 2 days, the bacteria were in contact with the apical surface of the epithelium. After 4 days, the bacteria-separating mucus layer was 142±21 μm (N=3 samples) in thickness. After 6 days, the thickness of the mucus layer had increased to 302±28 μm as shown by the separation between the bacteria and the epithelial monolayer. See FIG. 3D. These results demonstrate that the mucus thickness can be readily adjusted by the duration of ALI (FIG. 3E). The thickness of the mucus was consistent across the surface (302±28 μm), possibly due to its ability to flow and re-distribute as a result of its water content. A similar result was observed by overlaying 1 μm red fluorescent beads onto the mucus layer (FIG. 3F). This in vitro generated mucus layer resembles the characteristic of in vivo inner colon mucus layer by forming a barrier competent to segregate the epithelium from luminal microbes and microbeads.[46] To visualize both the mucus and epithelium, the sample was dehydrated and the mucus was partially removed from the epithelium (dashed line is the boundary in FIG. 3G). E. coli were found only on the surface of the mucus layer and were not seen in contact with the epithelium. This result again demonstrates that the hydrated mucus layer formed a barrier to segregate epithelium and microbes (FIG. 3G).

The ALI culture method has been used for bronchial epithelial cells,[47] keratinocytes,[48] adenocarcinoma intestinal cell lines,[37] and intestinal organoids.[49] ALI has also been used to culture primary small intestinal epithelial cells on porous membrane inserts in a commercial product (MatTek's 3D tissue model from MatTek Corporation). However, MatTek's 3D tissue model has not been shown to support a dense, continuous, microbead or bacterial-separating mucus layer with controllable thickness. Applicant has tested primary human small intestinal (jejunum) epithelial cells using the above ALI strategies (DM or DM-VIP), but a dense and thick mucus layer was not generated. The disclosed methods are applicable to primary human colonic cells, and these data show for the first time the creation of an in vitro colonic mucus system possessing in-vivo-like mucus characteristics.

Example 3

Figure 4A:
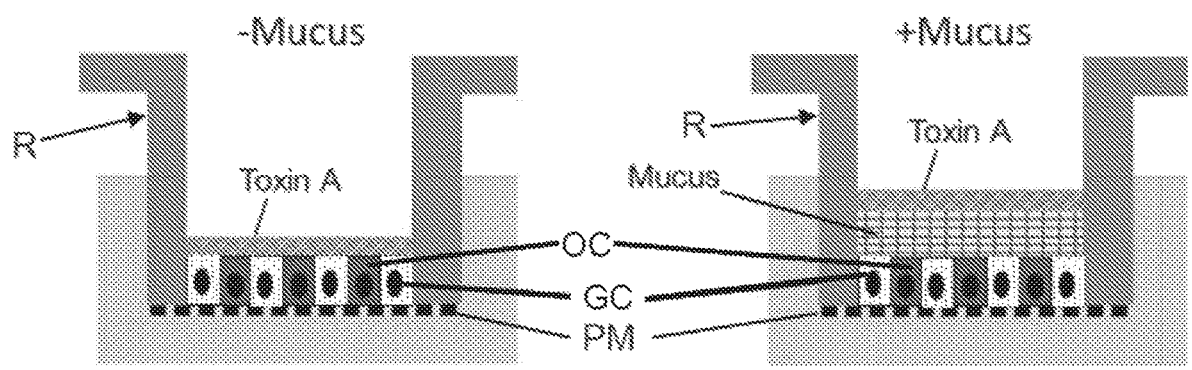
FIGS. 4A through 4F show the effect of $C.\ difficile$ toxin A on human colonic epithelium in the absence or presence of the VIP-enhanced mucus layer.
Figure 4B:
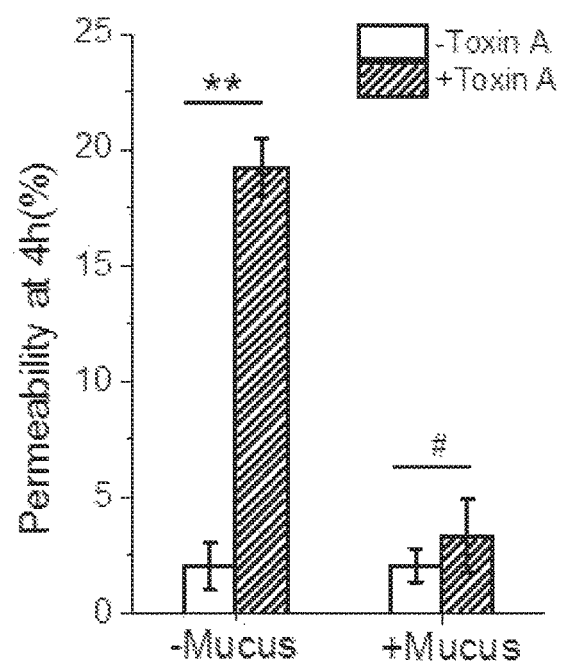
Figure 4C:
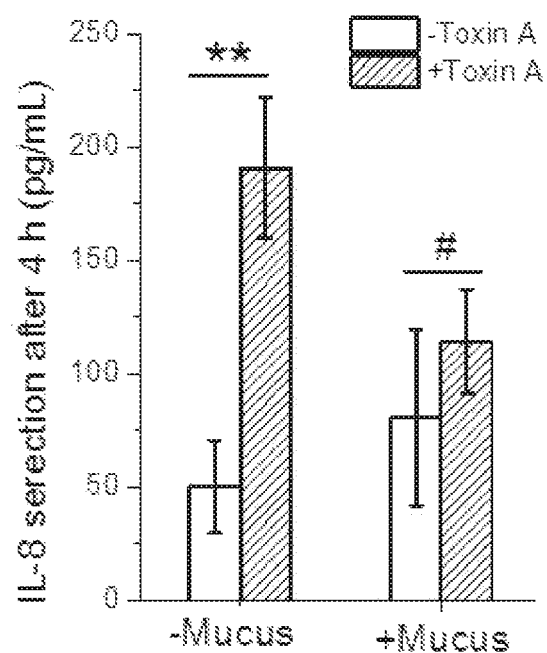
Figure 4D:
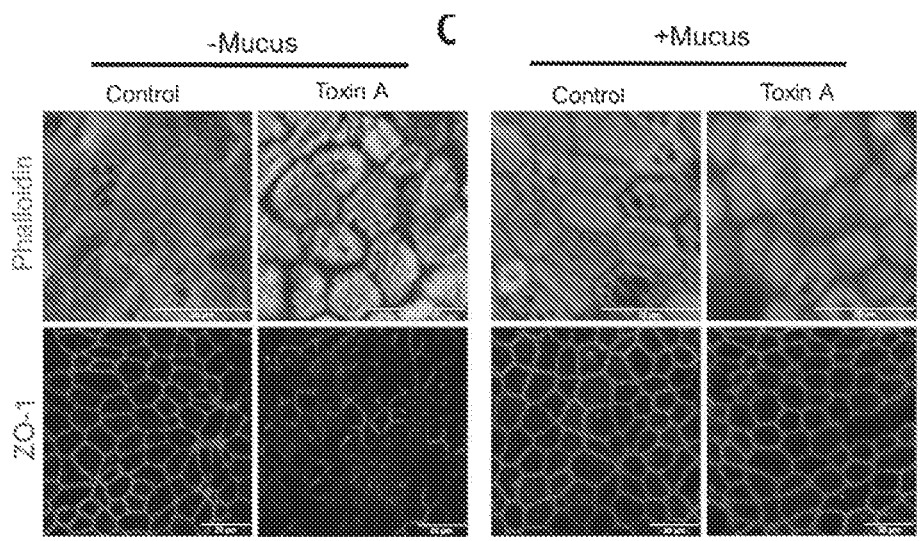

A Mucus Layer Hinders the Effect of C. difficile Toxin on Primary Human Colonic Epithelium To demonstrate that the mucus layer improves the physiological relevance of an in vitro colonic epithelial model, primary human colonic epithelium (GC and/or OC) was exposed to C. difficile toxin in the absence or presence of a mucus layer (FIG. 4A). C. difficile produces two potent toxins, A and B, capable of inactivating host GTPases (including Rho, Rac, and Cdc42), leading to alteration of the epithelial barrier, damage to human intestinal mucosa and inflammation of the colon.[50] In the absence of a mucus layer in the submerged culture method, toxin A quickly induced cell damage, and the earliest change was observed within 2 h of toxin incubation. At 4 h, paracellular permeability was significantly increased in toxin-treated epithelial monolayers (FIG. 4B), and IL-8 secretion was also significantly enhanced (FIG. 4C). Both apical F-actin structures and ZO-1 tight junctions were markedly altered by toxin treatment. While control epithelial monolayers had organized F-actin in the apical brush border and the continuous "chicken wire" pattern of ZO-1, the toxin A treated monolayers exhibited cell rounding, disorganization and disruption of normal F-actin, and disassembly of ZO-1 architecture (FIG. 4D). This trend was observed at 8 h (FIGS. 4E and 4F) and 24 h. These results demonstrate that toxin A disrupts epithelial barrier function and elicits an immunological response, which is consistent with previous studies on other intestinal epithelium models.[15, 51, 52]

Figure 4E:
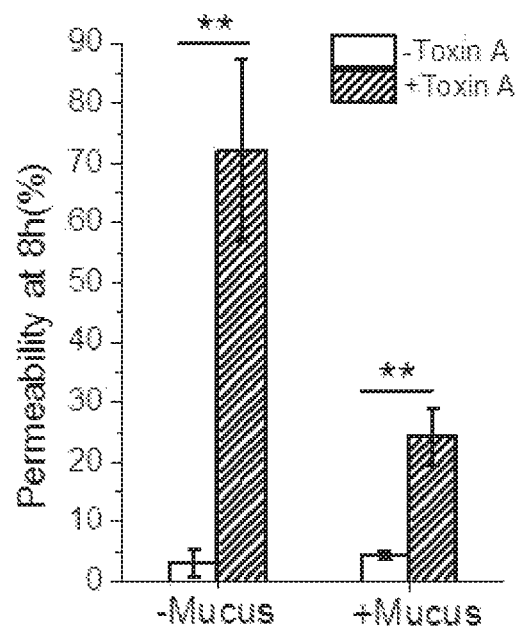
Figure 4F:
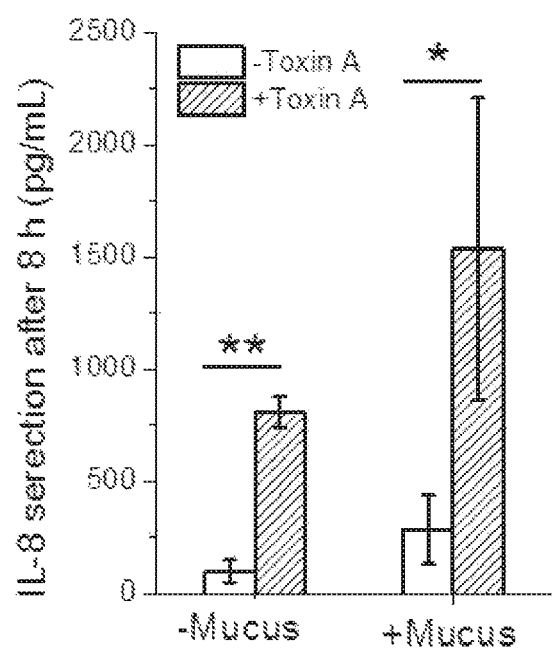

In the presence of a mucus layer generated by ALI plus DM-VIP, cell responses to toxin treatment were not observed at 4 h in terms of change in permeability and IL-8 production (FIGS. 4B and 4C), as well as cell morphology, F-actin and ZO-1 architecture (FIG. 4D). However, changes in permeability and IL-8 production were observed at 8 h (FIGS. 4E and 4F). These results suggest that the mucus layer served as physical barrier or trap for toxins such that they reached the epithelium through pure diffusion (with or without mucus binding sites) and with convective mixing no longer able to accelerate toxin travel to the epithelium. These findings suggest our intestinal mucus-epithelium is an improved physiologically relevant model to study the host and pathogen factors for C. difficile infection.

Example 4

Figure 5A:
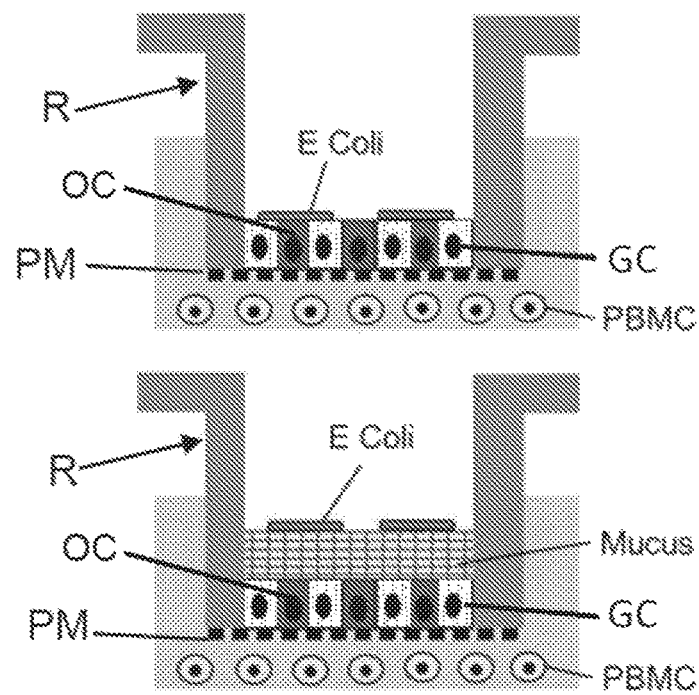
FIGS. 5A through 5E show cytokine production after a 24 h co-culture of GFP-expressing *E. coli* (GFP EC), epithelium and PBMCs in the absence or presence of the VIP-enhanced mucus layer.
Figure 5B:
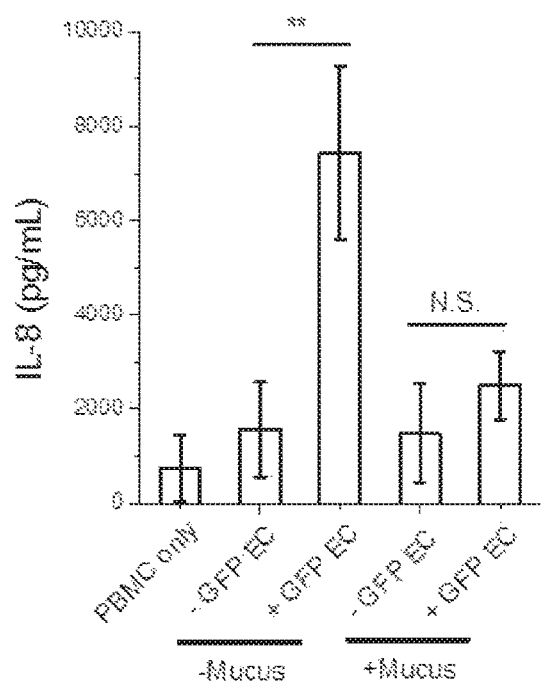
Figure 5C:
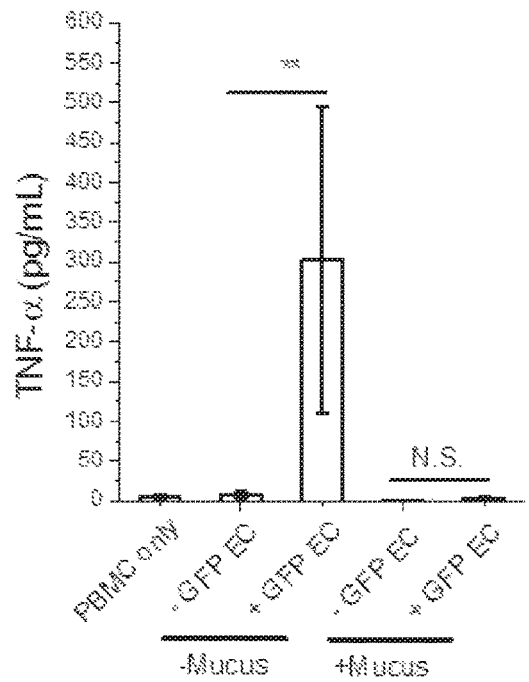
Figure 5D:
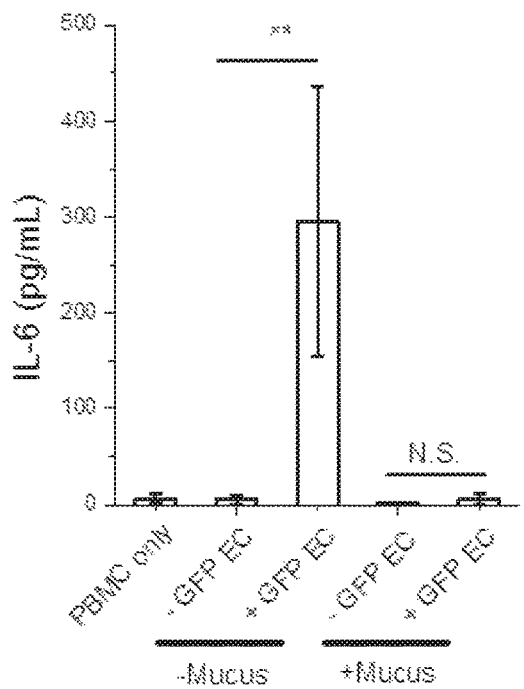
Figure 5E:
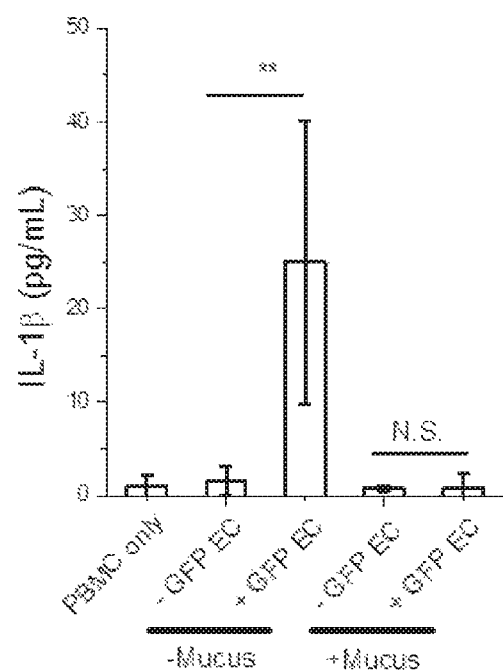

The Mucus Layer Serves as a Physical Barrier and Eliminates Bacteria-Induced Immune Response In vivo, the mucus layer acts as a vital component of the mucosal immune system by serving as a physical barrier to segregate commensal microbes from the host epithelium. Due to this physical segregation, commensal microbes coexist with epithelium without initiating a host inflammatory response.[6] To demonstrate that the in vitro mucus layer could serve the same protective function, the epithelial monolayer was co-cultured with E. coli (luminal side) and peripheral blood mononuclear cells (PBMCs, basal side) for 24 h in the absence (cultured under the submerged method) or presence (generated by ALI plus DM-VIP method) of the mucus layer (FIG. 5A). Inflammatory cytokines secreted from the basal epithelial side were quantified (FIGS. 5B through 5E). Without exposure to E. coli, the PBMCs produced relatively low levels of cytokines. The co-culture of PBMCs and epithelium produced a similar level of cytokines. However, after the epithelium was exposed to the bacteria in the absence of the mucus layer, a significant increase in cytokine production was observed relative to that of the control without bacteria. These results are similar to that obtained when the non-mucus producing Caco-2 cells are grown in the presence of non-pathogenic E. coli.[53, 54]

In contrast, the cytokine response to co-cultured E. coli was eliminated in the presence of the mucus layer. Without challenge by E. coli, the co-culture of PBMCs, epithelium and mucus layer produced a relatively low level of cytokines. After a 24 h co-culture with E. coli, cytokine production were not statistically different from that without bacteria. These data demonstrate that the mucus layer successfully served to functionally segregate the microbes from the epithelium, thus eliminating the immune response and emulating the in vivo condition.

It will be understood that various details of the presently disclosed subject matter may be changed without departing from the scope of the presently disclosed subject matter. Furthermore, the foregoing description is for the purpose of illustration only, and not for the purpose of limitation.

REFERENCES

All references listed herein including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

1. Allen A, Carroll N J H. Adherent and Soluble Mucus in the Stomach and Duodenum. Digestive Diseases and Sciences 1985; 30:55S.
2. Pelaseyed T, Bergstrom J H, Gustafsson J K, Ermund A, Birchenough G M H, Schütte A, van der Post S, Svensson F, Rodriguez-Piñeiro A M, Nyström E E L, Wising C, Johansson M E V, Hansson G C. The mucus and mucins of the goblet cells and enterocytes provide the first defense line of the gastrointestinal tract and interact with the immune system. Immunological reviews 2014; 260: 8-20.
3. Murgia X, Loretz B, Hartwig O, Hittinger M, Lehr C M. The role of mucus on drug transport and its potential to affect therapeutic outcomes. Adv Drug Deliv Rev 2018; 124:82-97.
4. Lehr C M, Poelma F G J, Junginger H E, Tukker J J. An estimate of turnover time of intestinal mucus gel layer in the rat in situ loop. International Journal of Pharmaceutics 1991; 70:235-240.
5. Wei X C, Yang Z, Rey F E, Ridaura V K, Davidson N O, Gordon J I, Semenkovich C F. Fatty Acid Synthase Modulates Intestinal Barrier Function through Palmitoylation of Mucin 2. Cell Host & Microbe 2012; 11:140-152.
6. Johansson M E V, Phillipson M, Petersson J, Velcich A, Holm L, Hansson G C. The inner of the two Muc2 mucin-dependent mucus layers in colon is devoid of bacteria. Proceedings of the National Academy of Sciences of the United States of America 2008; 105:15064-15069.
7. Hansson G C. Role of mucus layers in gut infection and inflammation. Current Opinion in Microbiology 2012; 15:57-62.
8. Carlson T L, Lock J Y, Carrier R L. Engineering the Mucus Barrier. Annual Review of Biomedical Engineering 2018; 20:197-220.
9. Werlang C, Cárcarmo-Oyarce G, Ribbeck K. Engineering mucus to study and influence the microbiome. Nature Reviews Materials 2019; 4:134-145.
10. Rogier E W, Frantz A L, Bruno M E C, Kaetzel C S. Secretory IgA is Concentrated in the Outer Layer of Colonic Mucus along with Gut Bacteria. Pathogens 2014; 3:390-403.
11. Gunasekara D B, Speer J, Wang Y, Nguyen D L, Reed M I, Smiddy N M, Parker J S, Fallon J K, Smith P C, Sims C E, Magness S T, Allbritton N L. A Monolayer of Primary Colonic Epithelium Generated on a Scaffold with a Gradient of Stiffness for Drug Transport Studies. Analytical Chemistry 2018; 90:13331-13340.
12. Quigley E M M. Gut bacteria in health and disease. Gastroenterology & hepatology 2013; 9:560-569.
13. Gagnon M, Berner A Z, Chervet N, Chassard C, Lacroix C. Comparison of the Caco-2, H T-29 and the mucus-secreting HT29-MTX intestinal cell models to investigate Salmonella adhesion and invasion. Journal of Microbiological Methods 2013; 94:274-279.
14. Lesuffleur T, Barbat A, Dussaulx E, Zweibaum A. Growth adaptation to methotrexate of HT-29 human colon carcinoma cells is associated with their ability to differentiate into columnar absorptive and mucus-secreting cells. Cancer Research 1990; 50:6334-6343.
15. Nusrat A, von Eichel-Streiber C, Turner J R, Verkade P, Madara J L, Parkos C A. Clostridium difficile Toxins Disrupt Epithelial Barrier Function by Altering Membrane Microdomain Localization of Tight Junction Proteins. Infection and Immunity 2001; 69:1329-1336.
16. Sato T, Vries R G, Snippert H J, van de Wetering M, Barker N, Stange D E, van Es J H, Abo A, Kujala P, Peters P J, Clevers H. Single Lgr5 stem cells build crypt-villus structures in vitro without a mesenchymal niche. Nature 2009; 459:262-U147.
17. Date S, Sato T. Mini-Gut Organoids: Reconstitution of Stem Cell Niche. In: Schekman R, ed. Annual Review of Cell and Developmental Biology, Vol 31. Volume 31, 2015:269-289.
18. Sato T, Stange D E, Ferrante M, Vries R G J, van Es J H, van den Brink S, van Houdt W J, Pronk A, van Gorp J, Siersema P D, Clevers H. Long-term Expansion of Epithelial Organoids From Human Colon, Adenoma, Adenocarcinoma, and Barrett's Epithelium. Gastroenterology 2011; 141:1762-1772.
19. Yin X L, Farin H F, van Es J H, Clevers H, Langer R, Karp J M. Niche-independent high-purity cultures of Lgr5(+) intestinal stem cells and their progeny. Nature Methods 2014; 11:106-112.
20. Fatehullah A, Appleton P L, Nathke I S. Cell and tissue polarity in the intestinal tract during tumourigenesis: cells still know the right way up, but tissue organization is lost.

Philosophical Transactions of the Royal Society B-Biological Sciences 2013; 368:20130014.

21. Moon C, VanDussen K L, Miyoshi H, Stappenbeck T S. Development of a primary mouse intestinal epithelial cell monolayer culture system to evaluate factors that modulate IgA transcytosis. Mucosal Immunology 2014; 7:818-828.

22. VanDussen K L, Marinshaw J M, Shaikh N, Miyoshi H, Moon C, Tarr P I, Ciorba M A, Stappenbeck T S. Development of an enhanced human gastrointestinal epithelial culture system to facilitate patient-based assays. Gut 2015; 64:911-920.

23. In J, Foulke-Abel J, Zachos N C, Hansen A-M, Kaper J B, Bernstein H D, Halushka M, Bluff S, Estes M K, Donowitz M, Kovbasnjuk O. Enterohemorrhagic *Escherichia coli* Reduces Mucus and Intermicrovillar Bridges in Human Stem Cell-Derived Colonoids. Cellular and Molecular Gastroenterology and Hepatology 2016; 2:48-62.e3.

24. Kozuka K, He Y, Koo-Mccoy S, Kumaraswamy P, Nie B, Shaw K, Chan P, Leadbetter M, He L, Lewis J G, Zhong Z, Charmot D, Balaa M, King A J, Caldwell J S, Siegel M. Development and Characterization of a Human and Mouse Intestinal Epithelial Cell Monolayer Platform. Stem Cell Reports 2017; 9:1976-1990.

25. Noel G, Baetz N W, Staab J F, Donowitz M, Kovbasnjuk O, Pasetti M F, Zachos N C. A primary human macrophage-enteroid co-culture model to investigate mucosal gut physiology and host-pathogen interactions. Scientific Reports 2017; 7:45270.

26. Puzan M, Hosic S, Ghio C, Koppes A. Enteric Nervous System Regulation of Intestinal Stem Cell Differentiation and Epithelial Monolayer Function. Scientific Reports 2018; 8:6313.

27. Wang Y L, DiSalvo M, Gunasekara D B, Dutton J, Proctor A, Lebhar M S, Williamson I A, Speer J, Howard R L, Smiddy N M, Bultman S J, Sims C E, Magness S T, Allbritton N L. Self-renewing Monolayer of Primary Colonic or Rectal Epithelial Cells. Cellular and Molecular Gastroenterology and Hepatology 2017; 4:165-+.

28. Madden L R, Nguyen T V, Garcia-Mojica S, Shah V, Le A V, Peier A, Visconti R, Parker E M, Presnell S C, Nguyen D G, Retting K N. Bioprinted 3D Primary Human Intestinal Tissues Model Aspects of Native Physiology and ADME/Tox Functions. iScience 2018; 2:156-167.

29. Wang Y, Kim R, Hwang S-H J, Dutton J, Sims C E, Allbritton N L. Analysis of Interleukin 8 Secretion by a Stem-Cell-Derived Human-Intestinal-Epithelial-Monolayer Platform. Analytical Chemistry 2018; 90:11523-11530.

30. Wang Y L, Kim R, Gunasekara D B, Reed M I, DiSalvo M, Nguyen D L, Bultman S J, Sims C E, Magness S T, Allbritton N L. Formation of Human Colonic Crypt Array by Application of Chemical Gradients Across a Shaped Epithelial Monolayer. Cellular and Molecular Gastroenterology and Hepatology 2018; 5:113-130.

31. Whitcutt M J, Adler K B, Wu R. A biphasic chamber system for maintaining polarity of differentiation of cultured respiratory tract epithelial cells. In Vitro Cellular & Developmental Biology 1988; 24:420-428.

32. Gray T E, Guzman K, Davis C W, Abdullah L H, Nettesheim P. Mucociliary differentiation of serially passaged normal human tracheobronchial epithelial cells. American Journal of Respiratory Cell and Molecular Biology 1996; 14:104-112.

33. Raredon M S B, Ghaedi M, Calle E A, Niklason L E. A Rotating Bioreactor for Scalable Culture and Differentiation of Respiratory Epithelium. Cell Medicine 2015; 7:109-121.

34. O'Boyle N, Sutherland E, Berry C C, Davies R L. Temporal dynamics of ovine airway epithelial cell differentiation at an air-liquid interface. Plos One 2017; 12.

35. Ootani A, Toda S, Fujimoto K, Sugihara H. An air-liquid interface promotes the differentiation of gastric surface mucous cells (GSM06) in culture. Biochemical and Biophysical Research Communications 2000; 271:741-746.

36. Yokoyama F, Sakata Y, Ootani A, Fujise T, Kakimoto T, Amemori S, Shiraishi R, Kuroki T, Tsunada S, Iwakiri R, Fujimoto K. Differentiation of gastric surface mucous cells (GSM06) induced by air-liquid interface is regulated partly through mitogen-activated protein kinase pathway. Journal of Gastroenterology and Hepatology 2007; 22:2310-2315.

37. Navabi N, McGuckin M A, Linden S K. Gastrointestinal Cell Lines Form Polarized Epithelia with an Adherent Mucus Layer when Cultured in Semi-Wet Interfaces with Mechanical Stimulation. Plos One 2013; 8.

38. Elkins M R, Bye P T P. Mechanisms and applications of hypertonic saline. Journal of the Royal Society of Medicine 2011; 104:S2-S5.

39. J. T, J. M. P, V. P. K, X. D. Z. Effect of osmotic response element binding protein on mucus secretion with hypertonicity in human airway epithelial cells. Zhonghua Yi Xue Za Zhi 2011; 91:549-553.

40. Ludeking A, Fegert P, Blin N, Gott P. Osmotic changes and ethanol modify TFF gene expression in gastrointestinal cell lines. Febs Letters 1998; 439:180-184.

41. Shields R, Miles J B, Gilbertson C. Absorption and secretion of water and electrolytes by the intact colon in a patient with primary aldosteronism. British Medical Journal 1968; 1:93-96.

42. Wapnir R A, Teichberg S. Regulation mechanisms of intestinal secretion: implications in nutrient absorption. The Journal of Nutritional Biochemistry 2002; 13:190-199.

43. Koch T R, Michener S R, Go V L W. Plasma vasoactive intestinal polypeptide concentration determination in patients with diarrhea. Gastroenterology 1991; 100:99-106.

44. Schwartz C J, Kimberg D V, Sheerin H E, Field M, Said S I. Vasoactive intestinal peptide stimulation of adenylate cyclase and active electrolyte secretion in intestinal mucosa. Journal of Clinical Investigation 1974; 54:536-544.

45. Wu X, Conlin V S, Morampudi V, Ryz N R, Nasser Y, Bhinder G, Bergstrom K S, Yu H B, Waterhouse C C M, Buchan A M J, Popescu O E, Gibson W T, Waschek J A, Vallance B A, Jacobson K. Vasoactive Intestinal Polypeptide Promotes Intestinal Barrier Homeostasis and Protection Against Colitis in Mice. Plos One 2015; 10: e0125225.

46. Johansson M E V, Gustafsson J K, Holmén-Larsson J, Jabbar K S, Xia L, Xu H, Ghishan F K, Carvalho F A, Gewirtz A T, Sjovall H, Hansson G C. Bacteria penetrate the normally impenetrable inner colon mucus layer in both murine colitis models and patients with ulcerative colitis. Gut 2014; 63:281-291.

47. Lin H X, Li H, Cho H J, Bian S, Roh H J, Lee M K, Kim J S, Chung S J, Shim C K, Kim D D. Air-liquid interface (ALI) culture of human bronchial epithelial cell mono- 48. Bernstam L I, Vaughan F L, Bernstein I A. Keratinocytes grown at the air-liquid interface. In Vitro Cellular & Developmental Biology 1986; 22:695-705.
49. Ootani A, Li X N, Sangiorgi E, Ho Q T, Ueno H, Toda S, Sugihara H, Fujimoto K, Weissman I L, Capecchi M R, Kuo C J. Sustained in vitro intestinal epithelial culture within a Wnt-dependent stem cell niche. Nature Medicine 2009; 15:1-U140.
50. Voth D E, Ballard J D. *Clostridium difficile* toxins: mechanism of action and role in disease. Clinical microbiology reviews 2005; 18:247-263.
51. He D, Sougioultzis S, Hagen S, Liu J, Keates S, Keates A C, Pothoulakis C, LaMont J T. *Clostridium difficile* toxin A triggers human colonocyte IL-8 release via mitochondrial oxygen radical generation. Gastroenterology 2002; 122:1048-1057.
52. Mahida Y R, Makh S, Hyde S, Gray T, Borriello S P. Effect of *Clostridium difficile* toxin A on human intestinal epithelial cells: induction of interleukin 8 production and apoptosis after cell detachment. Gut 1996; 38:337-347.
53. Haller D, Bode C, Hammes W P, Pfeifer A M A, Schiffrin E J, Blum S. Non-pathogenic bacteria elicit a differential cytokine response by intestinal epithelial cell/leucocyte co-cultures. Gut 2000; 47:79-87.
54. Parlesak A, Haller D, Brinz S, Baeuerlein A, Bode C. Modulation of Cytokine Release by Differentiated CACO-2 Cells in a Compartmentalized Coculture Model with Mononuclear Leucocytes and Nonpathogenic Bacteria. Scandinavian Journal of Immunology 2004; 60:477-485.

What is claimed is:

1. A method of producing a live cell construct comprising a constitutively-produced and continuous mucus layer, the method comprising:
   (a) culturing stem cells that are capable of differentiating into mucus producing cells on a first surface of a porous membrane under a liquid-liquid interface to form a confluent cell monolayer, the liquid-liquid interface comprising:
      (i) a first liquid medium that is in contact with a luminal surface of the cell monolayer, and
      (ii) a second liquid medium that is in contact with a basal surface of the cell monolayer;
   (b) removing the first liquid medium;
   (c) adding vasoactive intestinal peptide (VIP) to the second liquid medium; and
   (d) culturing the cell monolayer to generate the constitutively-produced and continuous mucus layer across the luminal surface of the cell monolayer, wherein the constitutively-produced and continuous mucus layer is substantially impenetrable to micro-objects in a size range from about 1 micron to about 100 microns.

2. The method of claim 1, wherein the constitutively-produced and continuous mucus layer comprises a thickness of about 1 micron to about 1 cm.

3. The method of claim 2, wherein the thickness of the constitutively-produced and continuous mucus layer is about 30 microns to about 1 cm.

4. The method of claim 1, wherein a basal reservoir is present below the basal surface of the cell monolayer and a luminal reservoir is present above the luminal surface of the cell monolayer, and removing the first liquid medium produces an air-liquid interface at the luminal surface of the cell monolayer.

5. The method of claim 1, further comprising positioning a physical barrier on or above the luminal surface of the cell monolayer, wherein the physical barrier is (i) completely or substantially impermeable to liquid and mucin, or (ii) permeable to water but impermeable or substantially impermeable to mucin.

6. The method of claim 5, wherein the physical barrier is in direct contact with the luminal surface of the cell monolayer and/or the constitutively-produced and continuous mucus layer.

7. The method of claim 5, wherein the depth of the first liquid medium is in a range of about 0.001 mm to about 10 mm, and the first liquid medium is between the physical barrier and the luminal surface of the cell monolayer.

8. The method of claim 4, wherein the first and/or second liquid medium further comprises a hormone, a chemical additive, a food additive, a bacterial metabolite, and/or a physiologically hypertonic salt solution, wherein the chemical additive is selected from the group consisting of: butyrate, bone morphogenetic protein (BMP), dibenzazepine, DAPT, LY411575, forskolin, guaifenesin, carbachol, prostaglandins, phorbol 12-myristate 13-acetate, histamine, and N-(1-oxobutyl)-cyclic 3', 5'-(hydrogen phosphate) 2'-butanoate-adenosine monosodium salt.

9. The method of claim 1, wherein the stem cells are epithelial stem cells, intestinal epithelial stem cells, basal stem cells, induced pluripotent stem cells, respiratory stem cells, gastric stem cells, nasal stem cells, cervix stem cells, vaginal stem cells, uterine stem cells, urethral stem cells, olfactory stem cells, mouth stem cells, tongue stem cells, and/or conjunctival stem cells.

10. The method of claim 1, wherein the stem cells are intestinal epithelial stem cells.

11. The method of claim 1, wherein a force is applied parallel to the luminal surface of the cell monolayer during the culturing step.

12. The method of claim 11, wherein the force comprises application of a surface tension force or application of a mechanical force.

13. The method of claim 12, wherein the mechanical force is a movement generated by a stir bar, a semi-solid material moving parallel to the luminal surface of the cell monolayer, and/or circulation of a slurry on the top of the luminal surface of the cell monolayer.

14. The method of claim 1, wherein a basal reservoir is present below the basal surface of the cell monolayer and a luminal reservoir is present above the luminal surface of the cell monolayer, and wherein the volume of a liquid medium in the luminal reservoir is adjusted to a depth in a range of about 0.001 mm to about 10 mm above the luminal surface of the cell monolayer.

* * * * *